United States Patent
Kuhne et al.

(10) Patent No.: US 11,312,777 B2
(45) Date of Patent: *Apr. 26, 2022

(54) HUMAN MONOCLONAL ANTIBODIES THAT BIND CXCR4 AND USES THEREOF

(71) Applicant: E. R. SQUIBB & SONS, L.L.C., Princeton, NJ (US)

(72) Inventors: Michelle R. Kuhne, San Francisco, CA (US); Peter Brams, Sacramento, CA (US); Dawn M. Tanamachi, San Carlos, CA (US); Alan J. Korman, Piedmont, CA (US); Josephine M. Cardarelli, San Carlos, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 316 days.

This patent is subject to a terminal disclaimer.

(21) Appl. No.: 16/159,306

(22) Filed: Oct. 12, 2018

(65) Prior Publication Data
US 2019/0031763 A1  Jan. 31, 2019

Related U.S. Application Data

(62) Division of application No. 13/900,791, filed on May 23, 2013, now Pat. No. 10,106,615, which is a division of application No. 12/444,130, filed as application No. PCT/US2007/021152 on Oct. 1, 2007, now Pat. No. 8,450,464.

(60) Provisional application No. 60/827,851, filed on Oct. 2, 2006.

(51) Int. Cl.
*C07K 16/28* (2006.01)
*A61K 47/68* (2017.01)
*A61K 39/00* (2006.01)

(52) U.S. Cl.
CPC ...... *C07K 16/2866* (2013.01); *A61K 47/6803* (2017.08); *A61K 47/6849* (2017.08); *A61K 2039/505* (2013.01); *C07K 2317/21* (2013.01); *C07K 2317/73* (2013.01); *C07K 2317/76* (2013.01)

(58) Field of Classification Search
CPC ............ C07K 16/2866; C07K 2317/73; C07K 2317/76; A61K 47/6803; A61K 47/6849; A61K 2039/505
See application file for complete search history.

(56) References Cited

U.S. PATENT DOCUMENTS

| | | | | |
|---|---|---|---|---|
| 10,233,248 B2 * | 3/2019 | Ghobrial | ............ | C12Q 1/6886 |
| 10,428,151 B2 * | 10/2019 | Kuhne | ............ | A61K 31/4184 |
| 2002/0086014 A1 | 7/2002 | Korman et al. | | |
| 2003/0206909 A1 | 11/2003 | Hua et al. | | |
| 2004/0001822 A1 | 1/2004 | Levanon et al. | | |
| 2004/0110941 A2 | 6/2004 | Winter et al. | | |
| 2005/0013809 A1 | 1/2005 | Owens et al. | | |
| 2005/0054019 A1 | 3/2005 | Michaud et al. | | |
| 2005/0180983 A1 | 8/2005 | Keler et al. | | |
| 2005/0287149 A1 | 12/2005 | Keler et al. | | |
| 2006/0110383 A1 | 5/2006 | Honjo et al. | | |

FOREIGN PATENT DOCUMENTS

| | | |
|---|---|---|
| CL | 2249-2005 | 3/2006 |
| CL | 3322-2006 | 6/2007 |
| EP | 1 316 801 | 6/2003 |
| WO | WO 2004/035607 | 4/2004 |
| WO | WO 2004/059285 | 7/2004 |
| WO | WO 2006/089141 | 8/2006 |
| WO | WO 2006/089231 | 8/2006 |
| WO | WO 2006/096461 | 9/2006 |

OTHER PUBLICATIONS

Baribaud, F. et al. (2001) Antigenically distinct conformations of CXCR4. J. Virol. 75(19): 8957-8967.
Davies, J. et al. (1996) Affinity improvement of single antibody VH domains: residues in all three hypervariable regions affect antigen binding. Immunotechnol. 2: 169-179.
Endres, M.J. et al. (1996) CD4-independent infection by HIV-2 is mediated by fusin/CXCR4. Cell 87: 745-756.
Ghobrial, I.M. et al. (2004) The role of CXCR4 inhibitors as novel anti-angiogenesis agents in cancer Therapy. Blood 104(11): 365a, Abstract No. 1296, Poster Board #-Session 450-1.
Guleng, B. et al. (2005) Blockade of the stromal cell-derived Factor-1/CXCR4 axis attenuates in vivo tumor growth by inhibiting angiogenesis in a vascular endothelial growth factor-independent manner. Cancer Res. 65(13): 5864-5871.
Holt, L.J. et al. (2003) Domain antibodies: proteins for therapy, Trends Biotechnol. 21(11): 484-490.
Maynard, J. et al. (2000) Antibody engineering. Annu. Rev. Biomed. Eng. 2: 339-376.
Pini, A. et al. (1998) Design and Use of a Phage Display Library, J. Biol. Chem. 273(34): 21769-21776.
Vaday, G.G. et al. (2004) CXCR4 and CXCL12 (SDF-1) in prostate cancer: inhibitory effects of human single chain Fv antibodies, Clin. Cancer Res. 10: 5630-5639.
International Search Report for Application No. PCT/US2007/021152, dated Aug. 22, 2008.

(Continued)

*Primary Examiner* — Sharon X Wen
(74) *Attorney, Agent, or Firm* — Ashton J. Delauney

(57) ABSTRACT

The present disclosure provides isolated monoclonal antibodies that specifically bind to CXCR4 with high affinity, particularly human monoclonal antibodies. Nucleic acid molecules encoding the antibodies of this disclosure, expression vectors, host cells and methods for expressing the antibodies of this disclosure are also provided. Immunoconjugates, bispecific molecules and pharmaceutical compositions comprising the antibodies of this disclosure are also provided. This disclosure also provides methods for detecting CXCR4, as well as methods for treating various cancers, inflammatory disorders and HIV infection using an anti-CXCR4 antibody of this disclosure.

24 Claims, 24 Drawing Sheets
Specification includes a Sequence Listing.

(56) References Cited

OTHER PUBLICATIONS

Written Opinion for Application No. PCT/US2007/021152, dated Aug. 22, 2008.

Rudikoff, S. et al. (1982) Single amino acid substitution altering antigen-binding specificity, Proc. Natl. Acad. Sci. USA 79: 1979-1983.

MacCallum, R.M. et al. (1996) Antibody-antigen interactions: contact analysis and binding site topography, J. Mol. Biol. 26: 732-745.

De Pascalis, R. et al. (2002) Grafting of "abbreviated" complementarity-determining regions containing specificity-determining residues essential for ligand contact to engineer a less immunogenic humanized monoclonal antibody. J. Immunol. 169: 3076-3084.

Casset, F. et al. (2003) A peptide mimetic of an anti-CD4 monoclonal antibody by rational design. Biochem. Biophys. Res. Commun. 307: 198-205.

Vajdos, F.F. et al. (2002) Comprehensive functional maps of the antigen-binding site of an anti-ErbB2 antibody obtained with shotgun scanning mutagenesis. J. Mol. Biol. 320: 415-428.

Chen, Y. et al. (1999) Selection and analysis of an optimized anti-VEGF antibody: crystal structure of an affinity-matured Fab in complex with antigen. J. Mol. Biol. 293: 865-881.

Wu, H. et al. (1999) Humanization of a murine monoclonal antibody by simultaneous optimization of framework and CDR residues. J. Mol. Biol. 294: 151-162.

Padlan, E.A., et al. (1989) Structure of an antibody-antigen complex: crystal structure of the HyHEL-10 Fab-lysozyme complex. Proc Natl Acad Sci 86: 5938-5942.

Lamminmaki, U. et al. (2001) Crystal structure of a recombinant anti-estradiol Fab fragment in complex with $^{17}$beta-estradiol, J. Biol. Chem. 276: 36687-36694.

Carter, P.J. (2006) Potent antibody therapeutic by design. Nat. Rev. Immunol. 6: 343-357.

\* cited by examiner

```
Anti-CXCR4 Fab F7 VH

V segment:     3-48
D segment:     4-23
J segment:     JH6b

Q   V   Q   L   V   Q   S   G   G   G   L   V   Q   P   G   G   S   L
  1 CAG GTG CAG CTG GTG CAG TCT GGG GGA GGC TTG GTA CAG CCT GGG GGG TCC CTG

CDR1
                                                            ~~~~~~~~~~~~~~~~~~~
      R   L   S   C   A   A   A   G   F   T   F   S   S   Y   S   M   N   W
 55 AGA CTC TCC TGT GCA GCC GCT GGA TTC ACC TTC AGT AGC TAT AGC ATG AAC TGG

CDR2
                                                            ~~~~~~~~~~~~~~~~~~~
      V   R   Q   A   P   G   K   G   L   E   W   V   S   Y   I   S   S   R
109 GTC CGC CAG GCT CCA GGG AAG GGG CTG GAG TGG GTT TCA TAC ATT AGT AGT AGA

CDR2
   ~~~~~~~~~~~~~~~~~~~~~~~~~~~~~~~~~~~~~~~~~~~~~~~~~~~~~
      S   R   T   I   Y   Y   A   D   S   V   K   G   R   F   T   I   S   R
163 AGT AGA ACC ATA TAC TAC GCA GAC TCT GTG AAG GGC CGA TTC ACC ATC TCC AGA

D   N   A   K   N   S   L   Y   L   Q   M   N   S   L   R   D   E   D
217 GAC AAT GCC AAG AAC TCA CTG TAT CTG CAA ATG AAC AGC CTG AGA GAC GAG GAC

CDR3
                                              ~~~~~~~~~~~~~~~~~~~~~~~~~~~~~~~~~~~~~~~~~
      T   A   V   Y   Y   C   A   R   D   Y   G   G   Q   P   P   Y   Y   Y
271 ACG GCT GTG TAT TAC TGT GCG AGA GAT TAC GGT GGT CAA CCC CCT TAC TAC TAC

CDR3
   ~~~~~~~~~~~~~~~~~~~~~~~~~
      Y   Y   G   M   D   V   W   G   Q   G   T   T   V   T   V   S   S
325 TAC TAC GGT ATG GAC GTC TGG GGC CAA GGG ACC ACG GTC ACC GTC TCC TCA
```

FIGURE 1A

Anti-CXCR4 Fab F7 VK

```
V segment:      L15
J segment:      JK1

A   I   R   M   T   Q   S   P   S   S   L   S   A   S   V   G   D   R
  1  GCC ATC CGG ATG ACC CAG TCT CCA TCC TCA CTG TCT GCA TCT GTA GGA GAC AGA

CDR1
                                        ~~~~~~~~~~~~~~~~~~~~~~~~~~~~~~~~~~~~
      V   T   I   T   C   R   A   S   Q   G   I   S   S   W   L   A   W   Y
 55  GTC ACC ATC ACT TGT CGG GCG AGT CAG GGT ATT AGC AGC TGG TTA GCC TGG TAT

CDR2
                                                    ~~~~~~~~~~~~~~~~~~~~~~~
      Q   Q   K   P   E   K   A   P   K   S   L   I   Y   A   A   S   S   L
109  CAG CAG AAA CCA GAG AAA GCC CCT AAG TCC CTG ATC TAT GCT GCA TCC AGT TTG

CDR2
      ~~~~~~~
      Q   S   G   V   P   S   R   F   S   G   S   G   S   G   T   D   F   T
163  CAA AGT GGG GTC CCA TCA AGG TTC AGC GGC AGT GGA TCT GGG ACA GAT TTC ACT

CDR3
                                                                    ~~~~~~~
      L   T   I   S   S   L   Q   P   E   D   F   V   T   Y   Y   C   Q   Q
217  CTC ACC ATC AGC AGC CTG CAG CCT GAA GAT TTT GTA ACT TAT TAC TGC CAA CAG

CDR3
      ~~~~~~~~~~~~~~~~~~~~~~~~~~
      Y   N   S   Y   P   R   T   F   G   Q   G   T   K   V   E   I   K
271  TAT AAT AGT TAC CCT CGG ACG TTC GGC CAA GGG ACC AAG GTG GAA ATC AAA
```

FIGURE 1B

Anti-CXCR4 Fab F9 VH

```
V segment:      3-48
D segment:      4-23
J segment:      JH6b
```

```
      Q   V   Q   L   V   Q   S   G   G   G   L   V   Q   P   G   G   S   L
  1 CAG GTG CAG CTG GTG CAG TCT GGG GGA GGC TTG GTA CAG CCT GGG GGG TCC CTG
                                                                    CDR1
                                                                    ~~~~~~~~~~~~~~~~~~~~
      R   L   S   C   A   A   A   G   F   T   F   S   S   Y   S   M   N   W
 55 AGA CTC TCC TGT GCA GCC GCT GGA TTC ACC TTC AGT AGC TAT AGC ATG AAC TGG
                                                                    CDR2
                                                                    ~~~~~~~~~~~~~~~~~~~~
      V   R   Q   A   P   G   K   G   L   E   W   V   S   Y   I   S   S   R
109 GTC CGC CAG GCT CCA GGG AAG GGG CTG GAG TGG GTT TCA TAC ATT AGT AGT AGA
                CDR2
    ~~~~~~~~~~~~~~~~~~~~~~~~~~~~~~~~~~~~~~~~~~~~~~
      S   R   S   I   Y   Y   A   D   S   V   K   G   R   F   T   I   S   R
163 AGT AGA AGC ATA TAC TAC GCA GAC TCT GTG AAG GGC CGA TTC ACC ATC TCC AGA

D   N   A   K   N   S   L   Y   L   Q   M   N   S   L   R   D   E   D
217 GAC AAT GCC AAG AAC TCA CTG TAC CTG CAA ATG AAC AGC CTG AGA GAC GAG GAC
                                                                CDR3
                                                                ~~~~~~~~~~~~~~~~~~~~~~~~~~~~~~~~~~~~
      T   A   V   Y   Y   C   A   R   D   Y   G   G   Q   P   P   Y   Y   Y
271 ACG GCT GTG TAT TAC TGT GCG AGA GAT TAC GGT GGT CAA CCC CCT TAC TAC TAC
           CDR3
    ~~~~~~~~~~~~~~~~~~~~~~~
      Y   Y   G   M   D   V   W   G   Q   G   T   T   V   T   V   S   S
325 TAC TAC GGT ATG GAC GTC TGG GGC CAA GGG ACC ACG GTC ACC GTC TCC TCA
```

FIGURE 2A

```
Anti-CXCR4 Fab F9 VK

V segment:      L15
J segment:      JK1

E   I   V   L   T   Q   S   P   S   S   L   S   A   S   V   G   D   R
  1 GAA ATT GTG CTC ACC CAG TCT CCA TCC TCA CTG TCT GCA TCT GTA GGA GAC AGA

CDR1
                            ~~~~~~~~~~~~~~~~~~~~~~~~~~~~~~~~~~~~~~~~~~~~~
      V   T   I   T   C   R   A   S   Q   G   I   S   S   W   L   A   W   Y
 55 GTC ACC ATC ACT TGT CGG GCG AGT CAG GGT ATT AGC AGC TGG TTA GCC TGG TAT

CDR2
                                                ~~~~~~~~~~~~~~~~~~~~~~~~~
      Q   Q   K   P   E   K   A   P   K   S   L   I   Y   A   A   S   S   L
109 CAG CAG AAA CCA GAG AAA GCC CCT AAG TCC CTG ATC TAT GCT GCA TCC AGT TTG

CDR2
    ~~~~~~~~
      Q   S   G   V   P   P   R   F   S   G   S   G   S   G   T   D   F   T
163 CAA AGT GGG GTC CCA CCA AGG TTC AGC GGC AGT GGA TCT GGG ACA GAT TTC ACT

CDR3
                                                                    ~~~~~~~~
      L   T   I   S   S   L   Q   P   E   D   F   A   T   Y   Y   C   Q   Q
217 CTC ACC ATC AGC AGC CTG CAG CCT GAA GAT TTT GCA ACT TAT TAC TGC CAA CAG

CDR3
    ~~~~~~~~~~~~~~~~~~~~~~~~~~~
      Y   N   S   Y   P   R   T   F   G   Q   G   T   K   V   E   I   K
271 TAT AAT AGT TAC CCT CGG ACG TTC GGC CAA GGG ACC AAG GTG GAA ATC AAA
```

FIGURE 2B

Anti-CXCR4 Fab D1 VH

V segment:   3-48
D segment:   4-23
J segment:   JH6b

```
      E   V   Q   L   V   Q   S   G   G   G   L   V   Q   P   G   G   S   L
  1 GAG GTG CAG CTG GTG CAG TCT GGG GGA GGC TTG GTA CAG CCT GGG GGG TCC CTG

CDR1
                                                  ~~~~~~~~~~~~~~~~~~~~
      R   L   S   C   A   A   A   G   F   T   F   S   S   Y   S   M   N   W
 55 AGA CTC TCC TGT GCA GCC GCT GGA TTC ACC TTC AGT AGC TAT AGC ATG AAC TGG

CDR2
                                                  ~~~~~~~~~~~~~~~~~~~~
      V   R   Q   A   P   G   K   G   L   E   W   V   S   Y   I   S   S   R
109 GTC CGC CAG GCT CCA GGG AAG GGG CTG GAG TGG GTT TCA TAC ATT AGT AGT CGT

CDR2
    ~~~~~~~~~~~~~~~~~~~~~~~~~~~~~~~~~~~~~~~~~~~~~
      S   K   T   I   Y   Y   A   D   S   V   K   G   R   F   T   I   S   R
163 AGT AAA ACC ATA TAC TAC GCA GAC TCT GTG AAG GGC CGA TTC ACC ATC TCC AGA

D   N   A   R   N   S   L   Y   L   Q   M   N   S   L   R   D   E   D
217 GAC AAT GCC AGG AAC TCA CTG TAT CTG CAA ATG AAC AGC CTG AGA GAC GAG GAC

CDR3
                                    ~~~~~~~~~~~~~~~~~~~~~~~~~~~~~~~~~~~~~~
      T   A   V   Y   Y   C   A   R   D   Y   G   G   Q   P   P   Y   Y   Y
271 ACG GCT GTG TAT TAC TGT GCG AGA GAT TAC GGT GGT CAA CCC CCT TAC TAC TAC

CDR3
    ~~~~~~~~~~~~~~~~~~~~~~~
      Y   Y   G   M   D   V   W   G   Q   G   T   T   V   T   V   S   S
325 TAC TAC GGT ATG GAC GTC TGG GGC CAA GGG ACC ACG GTC ACC GTC TCC TCA
```

FIGURE 3A

Anti-CXCR4 Fab D1 VK

V segment:      L15
J segment:      JK1

```
      V   I   W   V   T   Q   S   P   S   S   L   S   A   S   V   G   D   R
  1 GTC ATC TGG GTG ACC CAG TCT CCA TCC TCA CTG TCT GCA TCT GTA GGA GAC AGA

CDR1
                                                  ~~~~~~~~~~~~~~~~~~~~~~~~~~~~~~~~
      V   T   I   T   C   R   T   S   Q   G   I   S   S   W   L   A   W   Y
 55 GTC ACC ATC ACT TGT CGG ACG AGT CAG GGT ATT AGC AGC TGG TTA GCC TGG TAT

CDR2
                                                                  ~~~~~~~~~~~~~~~~~~~~
      Q   Q   K   P   E   K   A   P   E   L   L   I   Y   A   A   S   S   L
109 CAG CAG AAA CCA GAG AAA GCC CCT GAG CTC CTG ATC TAT GCT GCA TCC AGT TTG

CDR2
    ~~~~~~~
      Q   S   G   V   P   S   R   F   S   G   S   G   S   G   T   D   F   T
163 CAA AGT GGG GTC CCA TCA AGG TTC AGC GGC AGT GGA TCT GGG ACA GAT TTC ACT

CDR3
                                                                     ~~~~~~~~
      L   T   I   S   S   L   Q   P   E   D   F   A   T   Y   Y   C   Q   Q
217 CTC ACC ATC AGC AGC CTG CAG CCT GAA GAT TTT GCA ACT TAT TAC TGC CAA CAG

CDR3
    ~~~~~~~~~~~~~~~~~~~~~~~~~~~~
      Y   N   S   Y   P   R   T   F   G   Q   G   T   K   V   E   I   K
271 TAT AAT AGT TAC CCT CGG ACG TTC GGC CAA GGG ACC AAG GTG AAA ATC AAA
```

FIGURE 3B

Anti-CXCR4 Fab E2 VH

V segment:    3-48
D segment:    4-23
J segment:    JH6b

```
      E   V   Q   L   V   Q   S   G   G   G   L   V   Q   P   G   G   S   L
  1   GAG GTG CAG CTG GTG CAG TCT GGG GGA GGC TTG GTA CAG CCT GGG GGG TCC CTG

CDR1
                                                              ~~~~~~~~~~~~~~~~~~~~
      R   L   S   C   A   A   A   G   F   T   F   S   S   Y   S   M   N   W
 55   AGA CTC TCC TGT GCA GCC GCT GGA TTC ACC TTC AGT AGC TAT AGC ATG AAC TGG

CDR2
                                                              ~~~~~~~~~~~~~~~~~~~~
      V   R   Q   A   P   G   K   G   L   E   W   V   S   Y   I   S   S   R
109   GTC CGC CAG GCT CCA GGG AAG GGG CTG GAG TGG GTT TCA TAC ATT AGT AGT AGA

CDR2
      ~~~~~~~~~~~~~~~~~~~~~~~~~~~~~~~~~~~~~~~~~~~~~~~~~~~~~
      S   R   T   I   Y   Y   A   D   S   V   K   G   R   F   T   I   S   R
163   AGT AGA ACC ATA TAC TAC GCA GAC TCT GTG AAG GGC CGA TTC ACC ATC TCC AGA

D   N   A   K   N   S   L   Y   L   Q   M   N   S   L   R   D   E   D
217   GAC AAT GCC AAG AAC TCA CTG TAT CTG CAA ATG AAC AGC CTG AGA GAC GAG GAC

CDR3
                                                        ~~~~~~~~~~~~~~~~~~~~~~~~~~~~
      T   A   V   Y   Y   C   A   R   D   Y   G   G   Q   P   P   Y   H   Y
271   ACG GCT GTG TAT TAC TGT GCG AGA GAT TAC GGT GGT CAA CCC CCT TAC CAC TAC

CDR3
      ~~~~~~~~~~~~~~~~~~~~~~~
      Y   Y   G   M   D   V   W   G   Q   G   T   T   V   T   V   S   S
325   TAC TAC GGT ATG GAC GTC TGG GGC CAA GGG ACC ACG GTC ACC GTC TCC TCA
```

FIGURE 4A

Anti-CXCR4 Fab E2 VK

V segment:     L15
J segment:     JK1

```
        E   I   V   L   T   Q   S   P   S   S   L   S   A   S   V   G   D   R
    1   GAA ATT GTG CTC ACC CAG TCT CCA TCC TCA CTG TCT GCA TCT GTA GGG GAC AGA

CDR1
                                        ~~~~~~~~~~~~~~~~~~~~~~~~~~~~~~~~~~~~~~~
        V   T   I   T   C   R   A   S   Q   G   I   S   N   W   L   A   W   Y
   55   GTC ACC ATC ACT TGT CGG GCG AGT CAG GGT ATT AGC AAC TGG TTA GCC TGG TAT

CDR2
                                                            ~~~~~~~~~~~~~~~~~~~~
        Q   Q   K   P   E   K   A   P   K   S   L   I   Y   A   A   S   S   L
  109   CAG CAG AAA CCA GAG AAA GCC CCT AAG TCC CTG ATC TAT GCT GCA TCC AGT TTG

CDR2
        ~~~~~~~~
        Q   S   G   V   P   S   R   F   S   G   S   G   S   G   T   D   F   T
  163   CAA AGT GGG GTC CCA TCA AGG TTC AGC GGC AGT GGA TCT GGG ACA GAT TTC ACT

CDR3
                                                                    ~~~~~~~~
        L   T   I   S   S   L   Q   P   E   D   F   A   T   Y   Y   C   Q   Q
  217   CTC ACC ATC AGC AGC CTG CAG CCT GAA GAT TTT GCG ACT TAT TAC TGC CAA CAG

CDR3
        ~~~~~~~~~~~~~~~~~~~~~~~~~~~~
        Y   N   S   Y   P   R   T   F   G   Q   G   T   K   V   E   I   K
  271   TAT AAT AGT TAC CCT CGG ACG TTC GGC CAA GGG ACC AAG GTG GAA ATC AAA
```

FIGURE 4B

Anti-CXCR4 Fab F7 VH region

```
                                                           CDR1
3-48 germline  E V Q L V E S G G G L V Q P G G S L R L S C A A S G F T F S S Y S M N W
F7 VH          Q - - - - - - - - - - - - - - - - - - - - - - - A - - - - - - - - - - -
F7GL VH        - - - - - - - - - - - - - - - - - - - - - - - A - - - - - - - - - - -

CDR2
3-48 germline  V R Q A P G K G L E W V S Y I S S S S T I Y Y A D S V K G R F T I S R
F7 VH          - - - - - - - - - - - - - - - - - - R - - - - - - - - - - - - - - -
F7GL VH        - - - - - - - - - - - - - - - - - - R - - - - - - - - - - - - - - -

CDR3
3-48 germline  D N A K N S L Y L Q M N S L R D E D T A V Y Y C A R
JH6b germline                                                      - - - - D Y G G Q P P   Y Y Y
F7 VH          - - - - - - - - - - - - - - - - - - - - - - - - -  - - - - D Y G G Q P P   - - -
F7GL VH        - - - - - - - - - - - - - - - - - - - - - - - - -  - - - - D Y G G Q P P   - - -

CDR3
JH6b germline  Y Y G M D V W G Q G T T V T V S S     (JH6b)
F7 VH          - - - - - - - - - - - - - - - -       (JH6b)
F7GL VH        - - - - - - - - - - - - - - - -
```

FIGURE 5A

```
Anti-CXCR4 Fab F7 VK region

CDR1
                                                 _____
L15 germline   D I Q M T Q S P S S L S A S V G D R V T I T C R A S Q G I S S
F7 VK          A - R - - - - - - - - - - - - - - - - - - - - - - - - - - -
F7GL VK        - - - - - - - - - - - - - - - - - - - - - - - - - - - - - -

CDR2
                                 _____
L15 germline   W L A W Y Q Q K P E K A P K S L I Y A A S S L Q S G V P S R F
F7 VK          - - - - - - - - - - - - - - - - - - - - - - - - - - - - - -
F7GL VK        - - - - - - - - - - - - - - - - - - - - - - - - - - - - - -

CDR3
                                                       _____
L15 germline   S G S G S G T D F T L T I S S L Q P E D F A T Y Y C Q Q Y N S
F7 VK          - - - - - - - - - - - - - - - - - - - - - - - V - - - - - -
F7GL VK        - - - - - - - - - - - - - - - - - - - - - - - V - - - - - -

L15 germline   Y P
JK1 germline         T F G Q G T K V E I K
F7 VK          - - R - - - - - - - - - - -   (JK1)
F7GL VK        - - R - - - - - - - - - - -   (JK1)
```

FIGURE 5B

Anti-CXCR4 Fab F9 VH region

```
                                                                    CDR1
3-48 germline   E V Q L V E S G G G L V Q P G G S L R L S C A A S G F T F S S Y S M N W
F9 VH           Q - - - - - - - - - Q - - - - - - - - - - - - A - - - - - - - - - - -
F9GL VH         - - - - - - - - - - - - - - - - - - - - - - A - - - - - - - - - - - -

CDR2
3-48 germline   V R Q A P G K G L E W V S Y I S S S S T I Y Y A D S V K G R F T I S R
F9 VH           - - - - - - - - - - - - - - - - - - R - R S - - - - - - - - - - - - -
F9GL VH         - - - - - - - - - - - - - - - - - - R - R S - - - - - - - - - - - - -

CDR3
3-48 germline   D N A K N S L Y L Q M N S L R D E D T A V Y Y C A R
JH6b germline                                                       Y Y Y
F9 VH           - - - - - - - - - - - - - - - - - - - - - - - - -   - D Y G G Q P P - -
F9GL VH         - - - - - - - - - - - - - - - - - - - - - - - - -   - D Y G G Q P P - -

CDR3
JH6b germline   Y Y G M D V W G Q G T T V T V S S   (JH6b)
F9 VH           - - - - - - - - - - - - - - - - -   (JH6b)
F9GL VH         - - - - - - - - - - - - - - - - -
```

FIGURE 6A

Anti-CXCR4 Fab F9 VK region

```
                                                  CDR1
L15 germline   D I Q M T Q S P S S L S A S V G D R V T I T C R A S Q G I S S
F9 VK          E - V L - - - - - - - - - - - - - - - - - - - - - - - - - - 
F9GL VK        - - - - - - - - - - - - - - - - - - - - - - - - - - - - - -

CDR2
L15 germline   W L A W Y Q Q K P E K A P K S L I Y A A S S L Q S G V P S R F
F9 VK          - - - - - - - - - - - - - - - - - - - - - - - - - - - P - - 
F9GL VK        - - - - - - - - - - - - - - - - - - - - - - - - - - - P - -

CDR3
L15 germline   S G S G S G T D F T L T I S S L Q P E D F A T Y Y C Q Q Y N S
F9 VK          - - - - - - - - - - - - - - - - - - - - - - - - - - - - - - 
F9GL VK        - - - - - - - - - - - - - - - - - - - - - - - - - - - - - -

L15 germline   Y P
JK1 germline           T F G Q G T K V E I K
F9 VK          - -     - R - - - - - - - - -    (JK1)
F9GL VK        - -     - R - - - - - - - - -    (JK1)
```

FIGURE 6B

Anti-CXCR4 Fab D1 VH region

```
                                                                    _____CDR1
3-48 germline    E V Q L V E S G G G L V Q P G G S L R L S C A A S G F T F S S Y S M N W
D1 VH            - - - Q - - - - - - - - - - - - - - - - - - A - - - - - - - - - - - -
D1GL VH          - - - - - - - - - - - - - - - - - - - - - - A - - - - - - - - - - - -

_____CDR2
3-48 germline    V R Q A P G K G L E W V S Y I S S S S S T I Y Y A D S V K G R F T I S R
D1 VH            - - - - - - - - - - - - - - - - R - K - - - - - - - - - - - - - - - -
D1GL VH          - - - - - - - - - - - - - - - - R - K - - - - - - - - - - - - - - - -

_____CDR3
3-48 germline    D N A K N S L Y L Q M N S L R D E D T A V Y Y C A R
JH6b germline                                                                        Y Y Y
D1 VH            - - - R - - - - - - - - - - - - - - - - - - - - - D Y G G Q P P - - -
D1GL VH          - - - R - - - - - - - - - - - - - - - - - - - - - D Y G G Q P P - - -

_____CDR3
JH6b germline    Y Y G M D V W G Q G T T V T V S S
D1 VH            - - - - - - - - - - - - - - - - - (JH6b)
D1GL VH          - - - - - - - - - - - - - - - - - (JH6b)
```

FIGURE 7A

Anti-CXCR4 Fab D1 VK region

```
L15 germline    D I Q M T Q S P S S L S A S V G D R V T I T C R A S Q G I S S
D1 VK           V - W V - - - - - - - - - - - - - - - - - - - T - - - - - -
D1GL VK         - - - - - - - - - - - - - - - - - - - - - - - T - - - - - -
                                                              CDR1

L15 germline    W L A W Y Q Q K P E K A P K S L I Y A A S S L Q S G V P S R F
D1 VK           - - - - - - - - - - - - - - E L - - - - - - - - - - - - - -
D1GL VK         - - - - - - - - - - - - - - E L - - - - - - - - - - - - - -
                                                    CDR2

L15 germline    S G S G S G T D F T L T I S S L Q P E D F A T Y Y C Q Q Y N S
D1 VK           - - - - - - - - - - - - - - - - - - - - - - - - - - - - - -
D1GL VK         - - - - - - - - - - - - - - - - - - - - - - - - - - - - - -
                                                                    CDR3

CDR3
L15 germline    Y P
JK1 germline        T F G Q G T K V E I K
D1 VK           - - R - - - - - - - - -      (JK1)
D1GL VK         - - R - - - - - - - - -      (JK1)
```

FIGURE 7B

Anti-CXCR4 Fab E2 VH region

```
                                                                    CDR1
3-48 germline   E V Q L V E S G G G L V Q P G G S L R L S C A A S G F T F S S Y S M N W
E2 VH           - - - - - - Q - - - - - - - - - - - - - - - - - - A - - - - - - - - -
E2GL VH         - - - - - - - - - - - - - - - - - - - - - - - - - A - - - - - - - - -

CDR2
3-48 germline   V R Q A P G K G L E W V S Y I S S S S T I Y Y A D S V K G R F T I S R
E2 VH           - - - - - - - - - - - - - - - - - R - R - - - - - - - - - - - - - -
E2GL VH         - - - - - - - - - - - - - - - - - R - R - - - - - - - - - - - - - -

CDR3
3-48 germline   D N A K N S L Y L Q M N S L R D E D T A V Y Y C A R
JH6b germline                                                                Y Y Y
E2 VH           - - - - - - - - - - - - - - - - - - - - - - - - - - D Y G G Q P P - H
E2GL VH         - - - - - - - - - - - - - - - - - - - - - - - - - - D Y G G Q P P - H CDR3
JH6b germline   Y Y G M D V W G Q G T T V T V S S
E2 VH           - - - - - - - - - - - - - - - - - (JH6b)
E2GL VH         - - - - - - - - - - - - - - - - - (JH6b)
```

FIGURE 8A

Anti-CXCR4 Fab E2 VK region

```
                                                    CDR1
L15 germline   D I Q M T Q S P S S L S A S V G D R V T I T C R A S Q G I S S
E2 VK          E - V L - - - - - - - - - - - - - - - - - - - - - - - - - N
E2GL VK        - - - - - - - - - - - - - - - - - - - - - - - - - - - - - N CDR2
L15 germline   W L A W Y Q Q K P E K A P K S L I Y A A S S L Q S G V P S R F
E2 VK          - - - - - - - - - - - - - - - - - - - - - - - - - - - - - -
E2GL VK        - - - - - - - - - - - - - - - - - - - - - - - - - - - - - -

CDR3
L15 germline   S G S G S G T D F T L T I S S L Q P E D F A T Y Y C Q Q Y N S
E2 VK          - - - - - - - - - - - - - - - - - - - - - - - - - - - - - -
E2GL VK        - - - - - - - - - - - - - - - - - - - - - - - - - - - - - -

CDR3
L15 germline   Y P
JK1 germline         T F G Q G T K V E I K
E2 VK          - - R - - - - - - - - - - -   (JK1)
E2GL VK        - - R - - - - - - - - - - -   (JK1)
```

FIGURE 8B

SEQUENCE LISTING

```
<160> NUMBER OF SEQ ID NOS: 53

<210> SEQ ID NO 1
<211> LENGTH: 5
<212> TYPE: PRT
<213> ORGANISM: Homo sapiens

<400> SEQUENCE: 1

Ser Tyr Ser Met Asn
1               5

<210> SEQ ID NO 2
<211> LENGTH: 5
<212> TYPE: PRT
<213> ORGANISM: Homo sapiens

<400> SEQUENCE: 2
```

Ser Tyr Ser Met Asn
1               5

<210> SEQ ID NO 3
<211> LENGTH: 5
<212> TYPE: PRT
<213> ORGANISM: Homo sapiens

<400> SEQUENCE: 3

Ser Tyr Ser Met Asn
1               5

<210> SEQ ID NO 4
<211> LENGTH: 5
<212> TYPE: PRT
<213> ORGANISM: Homo sapiens

<400> SEQUENCE: 4

Ser Tyr Ser Met Asn
1               5

<210> SEQ ID NO 5
<211> LENGTH: 17
<212> TYPE: PRT
<213> ORGANISM: Homo sapiens

<400> SEQUENCE: 5

Tyr Ile Ser Ser Arg Ser Arg Thr Ile Tyr Tyr Ala Asp Ser Val Lys
1               5                   10                  15

Gly

<210> SEQ ID NO 6
<211> LENGTH: 17
<212> TYPE: PRT
<213> ORGANISM: Homo sapiens

<400> SEQUENCE: 6

Tyr Ile Ser Ser Arg Ser Arg Ser Ile Tyr Tyr Ala Asp Ser Val Lys
1               5                   10                  15

Gly

<210> SEQ ID NO 7
<211> LENGTH: 17
<212> TYPE: PRT
<213> ORGANISM: Homo sapiens

<400> SEQUENCE: 7

Tyr Ile Ser Ser Arg Ser Lys Thr Ile Tyr Tyr Ala Asp Ser Val Lys
1               5                   10                  15

Gly

<210> SEQ ID NO 8
<211> LENGTH: 17
<212> TYPE: PRT
<213> ORGANISM: Homo sapiens

<400> SEQUENCE: 8

Tyr Ile Ser Ser Arg Ser Arg Thr Ile Tyr Tyr Ala Asp Ser Val Lys
1               5                   10                  15

Gly

<210> SEQ ID NO 9

```
<211> LENGTH: 16
<212> TYPE: PRT
<213> ORGANISM: Homo sapiens

<400> SEQUENCE: 9

Asp Tyr Gly Gly Gln Pro Pro Tyr Tyr Tyr Tyr Gly Met Asp Val
1               5                   10                  15

<210> SEQ ID NO 10
<211> LENGTH: 16
<212> TYPE: PRT
<213> ORGANISM: Homo sapiens

<400> SEQUENCE: 10

Asp Tyr Gly Gly Gln Pro Pro Tyr Tyr Tyr Tyr Gly Met Asp Val
1               5                   10                  15

<210> SEQ ID NO 11
<211> LENGTH: 16
<212> TYPE: PRT
<213> ORGANISM: Homo sapiens

<400> SEQUENCE: 11

Asp Tyr Gly Gly Gln Pro Pro Tyr Tyr Tyr Tyr Gly Met Asp Val
1               5                   10                  15

<210> SEQ ID NO 12
<211> LENGTH: 16
<212> TYPE: PRT
<213> ORGANISM: Homo sapiens

<400> SEQUENCE: 12

Asp Tyr Gly Gly Gln Pro Pro Tyr His Tyr Tyr Gly Met Asp Val
1               5                   10                  15

<210> SEQ ID NO 13
<211> LENGTH: 11
<212> TYPE: PRT
<213> ORGANISM: Homo sapiens

<400> SEQUENCE: 13

Arg Ala Ser Gln Gly Ile Ser Ser Trp Leu Ala
1               5                   10

<210> SEQ ID NO 14
<211> LENGTH: 11
<212> TYPE: PRT
<213> ORGANISM: Homo sapiens

<400> SEQUENCE: 14

Arg Ala Ser Gln Gly Ile Ser Ser Trp Leu Ala
1               5                   10

<210> SEQ ID NO 15
<211> LENGTH: 11
<212> TYPE: PRT
<213> ORGANISM: Homo sapiens

<400> SEQUENCE: 15

Arg Thr Ser Gln Gly Ile Ser Ser Trp Leu Ala
1               5                   10

<210> SEQ ID NO 16
<211> LENGTH: 11
<212> TYPE: PRT
```

<213> ORGANISM: Homo sapiens

<400> SEQUENCE: 16

Arg Ala Ser Gln Gly Ile Ser Asn Trp Leu Ala
1               5                   10

<210> SEQ ID NO 17
<211> LENGTH: 7
<212> TYPE: PRT
<213> ORGANISM: Homo sapiens

<400> SEQUENCE: 17

Ala Ala Ser Ser Leu Gln Ser
1               5

<210> SEQ ID NO 18
<211> LENGTH: 7
<212> TYPE: PRT
<213> ORGANISM: Homo sapiens

<400> SEQUENCE: 18

Ala Ala Ser Ser Leu Gln Ser
1               5

<210> SEQ ID NO 19
<211> LENGTH: 7
<212> TYPE: PRT
<213> ORGANISM: Homo sapiens

<400> SEQUENCE: 19

Ala Ala Ser Ser Leu Gln Ser
1               5

<210> SEQ ID NO 20
<211> LENGTH: 7
<212> TYPE: PRT
<213> ORGANISM: Homo sapiens

<400> SEQUENCE: 20

Ala Ala Ser Ser Leu Gln Ser
1               5

<210> SEQ ID NO 21
<211> LENGTH: 9
<212> TYPE: PRT
<213> ORGANISM: Homo sapiens

<400> SEQUENCE: 21

Gln Gln Tyr Asn Ser Tyr Pro Arg Thr
1               5

<210> SEQ ID NO 22
<211> LENGTH: 9
<212> TYPE: PRT
<213> ORGANISM: Homo sapiens

<400> SEQUENCE: 22

Gln Gln Tyr Asn Ser Tyr Pro Arg Thr
1               5

<210> SEQ ID NO 23
<211> LENGTH: 9
<212> TYPE: PRT
<213> ORGANISM: Homo sapiens

<400> SEQUENCE: 23

Gln Gln Tyr Asn Ser Tyr Pro Arg Thr
1               5

<210> SEQ ID NO 24
<211> LENGTH: 9
<212> TYPE: PRT
<213> ORGANISM: Homo sapiens

<400> SEQUENCE: 24

Gln Gln Tyr Asn Ser Tyr Pro Arg Thr
1               5

<210> SEQ ID NO 25
<211> LENGTH: 125
<212> TYPE: PRT
<213> ORGANISM: Homo sapiens

<400> SEQUENCE: 25

Gln Val Gln Leu Val Gln Ser Gly Gly Gly Leu Val Gln Pro Gly Gly
1               5                   10                  15

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
                100                 105                 110

Asp Val Trp Gly Gln Gly Thr Thr Val Thr Val Ser Ser
            115                 120                 125

<210> SEQ ID NO 26
<211> LENGTH: 125
<212> TYPE: PRT
<213> ORGANISM: Homo sapiens

<400> SEQUENCE: 26

Gln Val Gln Leu Val Gln Ser Gly Gly Gly Leu Val Gln Pro Gly Gly
1               5                   10                  15

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Ser Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
                100                 105                 110

Asp Val Trp Gly Gln Gly Thr Thr Val Thr Val Ser Ser
            115                 120                 125

<210> SEQ ID NO 27
<211> LENGTH: 125
<212> TYPE: PRT
<213> ORGANISM: Homo sapiens

<400> SEQUENCE: 27

Glu Val Gln Leu Val Gln Ser Gly Gly Gly Leu Val Gln Pro Gly Gly
1               5                   10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Lys Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
        115                 120                 125

<210> SEQ ID NO 28
<211> LENGTH: 125
<212> TYPE: PRT
<213> ORGANISM: Homo sapiens

<400> SEQUENCE: 28

Glu Val Gln Leu Val Gln Ser Gly Gly Gly Leu Val Gln Pro Gly Gly
1               5                   10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr His Tyr Tyr Gly Met
            100                 105                 110

Asp Val Trp Gly Gln Gly Thr Thr Val Thr Val Ser Ser
        115                 120                 125

<210> SEQ ID NO 29
<211> LENGTH: 107
<212> TYPE: PRT
<213> ORGANISM: Homo sapiens

<400> SEQUENCE: 29

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

-continued

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Val Thr Tyr Tyr Cys Gln Gln Tyr Asn Ser Tyr Pro Arg
                 85                  90                  95

Thr Phe Gly Gln Gly Thr Lys Val Glu Ile Lys
            100                 105

<210> SEQ ID NO 30
<211> LENGTH: 107
<212> TYPE: PRT
<213> ORGANISM: Homo sapiens

<400> SEQUENCE: 30

Glu Ile Val Leu Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Pro Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
            100                 105

<210> SEQ ID NO 31
<211> LENGTH: 107
<212> TYPE: PRT
<213> ORGANISM: Homo sapiens

<400> SEQUENCE: 31

Val Ile Trp Val Thr Gln Ser Pro Ser Ser Leu Ser Ala Ser Val Gly
 1               5                  10                  15

Asp Arg Val Thr Ile Thr Cys Arg Thr Ser Gln Gly Ile Ser Ser Trp
                 20                  25                  30

Leu Ala Trp Tyr Gln Gln Lys Pro Glu Lys Ala Pro Glu Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro Arg
                 85                  90                  95

Thr Phe Gly Gln Gly Thr Lys Val Glu Ile Lys
            100                 105

<210> SEQ ID NO 32
<211> LENGTH: 107
<212> TYPE: PRT
<213> ORGANISM: Homo sapiens

<400> SEQUENCE: 32

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 33
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 33

| cag gtg cag ctg gtg cag tct ggg gga ggc ttg gta cag cct ggg ggg | 48 |
| Gln Val Gln Leu Val Gln Ser Gly Gly Gly Leu Val Gln Pro Gly Gly | |
| 1               5                   10                  15     | |

| tcc ctg aga ctc tcc tgt gca gcc gct gga ttc acc ttc agt agc tat | 96 |
| Ser Leu Arg Leu Ser Cys Ala Ala Ala Gly Phe Thr Phe Ser Ser Tyr | |
|             20                  25                  30         | |

| agc atg aac tgg gtc cgc cag gct cca ggg aag ggg ctg gag tgg gtt | 144 |
| Ser Met Asn Trp Val Arg Gln Ala Pro Gly Lys Gly Leu Glu Trp Val | |
|         35                  40                  45             | |

| tca tac att agt agt aga agt aga acc ata tac tac gca gac tct gtg | 192 |
| Ser Tyr Ile Ser Ser Arg Ser Arg Thr Ile Tyr Tyr Ala Asp Ser Val | |
|     50                  55                  60                 | |

| aag ggc cga ttc acc atc tcc aga gac aat gcc aag aac tca ctg tat | 240 |
| Lys Gly Arg Phe Thr Ile Ser Arg Asp Asn Ala Lys Asn Ser Leu Tyr | |
| 65                  70                  75                  80 | |

| ctg caa atg aac agc ctg aga gac gag gac acg gct gtg tat tac tgt | 288 |
| Leu Gln Met Asn Ser Leu Arg Asp Glu Asp Thr Ala Val Tyr Tyr Cys | |
|                 85                  90                  95     | |

| gcg aga gat tac ggt ggt caa ccc cct tac tac tac tac ggt atg | 336 |
| Ala Arg Asp Tyr Gly Gly Gln Pro Pro Tyr Tyr Tyr Tyr Gly Met | |
|             100                 105                 110     | |

| gac gtc tgg ggc caa ggg acc acg gtc acc gtc tcc tca | 375 |
| Asp Val Trp Gly Gln Gly Thr Thr Val Thr Val Ser Ser | |
|         115                 120                 125 | |

<210> SEQ ID NO 34
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 34

| cag gtg cag ctg gtg cag tct ggg gga ggc ttg gta cag cct ggg ggg | 48 |
| Gln Val Gln Leu Val Gln Ser Gly Gly Gly Leu Val Gln Pro Gly Gly | |

```
                1               5                       10                      15
tcc ctg aga ctc tcc tgt gca gcc gct gga ttc acc ttc agt agc tat         96
Ser Leu Arg Leu Ser Cys Ala Ala Ala Gly Phe Thr Phe Ser Ser Tyr
                20                      25                      30 agc atg aac tgg gtc cgc cag gct cca ggg aag ggg ctg gag tgg gtt         144
Ser Met Asn Trp Val Arg Gln Ala Pro Gly Lys Gly Leu Glu Trp Val
        35                      40                      45 tca tac att agt agt aga agt aga agc ata tac tac gca gac tct gtg         192
Ser Tyr Ile Ser Ser Arg Ser Arg Ser Ile Tyr Tyr Ala Asp Ser Val
    50                      55                      60 aag ggc cga ttc acc atc tcc aga gac aat gcc aag aac tca ctg tac         240
Lys Gly Arg Phe Thr Ile Ser Arg Asp Asn Ala Lys Asn Ser Leu Tyr
65                      70                      75                      80 ctg caa atg aac agc ctg aga gac gag gac acg gct gtg tat tac tgt         288
Leu Gln Met Asn Ser Leu Arg Asp Glu Asp Thr Ala Val Tyr Tyr Cys
                85                      90                      95 gcg aga gat tac ggt ggt caa ccc cct tac tac tac tac ggt atg             336
Ala Arg Asp Tyr Gly Gly Gln Pro Pro Tyr Tyr Tyr Tyr Gly Met
                100                     105                     110 gac gtc tgg ggc caa ggg acc acg gtc acc gtc tcc tca                     375
Asp Val Trp Gly Gln Gly Thr Thr Val Thr Val Ser Ser
                115                     120                     125

<210> SEQ ID NO 35
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 35 gag gtg cag ctg gtg cag tct ggg gga ggc ttg gta cag cct ggg ggg         48
Glu Val Gln Leu Val Gln Ser Gly Gly Gly Leu Val Gln Pro Gly Gly
1               5                       10                      15 tcc ctg aga ctc tcc tgt gca gcc gct gga ttc acc ttc agt agc tat         96
Ser Leu Arg Leu Ser Cys Ala Ala Ala Gly Phe Thr Phe Ser Ser Tyr
                20                      25                      30 agc atg aac tgg gtc cgc cag gct cca ggg aag ggg ctg gag tgg gtt         144
Ser Met Asn Trp Val Arg Gln Ala Pro Gly Lys Gly Leu Glu Trp Val
        35                      40                      45 tca tac att agt agt cgt agt aaa acc ata tac tac gca gac tct gtg         192
Ser Tyr Ile Ser Ser Arg Ser Lys Thr Ile Tyr Tyr Ala Asp Ser Val
    50                      55                      60 aag ggc cga ttc acc atc tcc aga gac aat gcc agg aac tca ctg tat         240
Lys Gly Arg Phe Thr Ile Ser Arg Asp Asn Ala Arg Asn Ser Leu Tyr
65                      70                      75                      80 ctg caa atg aac agc ctg aga gac gag gac acg gct gtg tat tac tgt         288
Leu Gln Met Asn Ser Leu Arg Asp Glu Asp Thr Ala Val Tyr Tyr Cys
                85                      90                      95 gcg aga gat tac ggt ggt caa ccc cct tac tac tac tac ggt atg             336
Ala Arg Asp Tyr Gly Gly Gln Pro Pro Tyr Tyr Tyr Tyr Gly Met
                100                     105                     110 gac gtc tgg ggc caa ggg acc acg gtc acc gtc tcc tca                     375
Asp Val Trp Gly Gln Gly Thr Thr Val Thr Val Ser Ser
                115                     120                     125

<210> SEQ ID NO 36
<211> LENGTH: 375
<212> TYPE: DNA
<213> ORGANISM: Homo sapiens
<220> FEATURE:
```

<221> NAME/KEY: CDS
<222> LOCATION: (1)..(375)

<400> SEQUENCE: 36

```
gag gtg cag ctg gtg cag tct ggg gga ggc ttg gta cag cct ggg ggg    48
Glu Val Gln Leu Val Gln Ser Gly Gly Gly Leu Val Gln Pro Gly Gly
 1               5                  10                  15 tcc ctg aga ctc tcc tgt gca gcc gct gga ttc acc ttc agt agc tat    96
Ser Leu Arg Leu Ser Cys Ala Ala Ala Gly Phe Thr Phe Ser Ser Tyr
             20                  25                  30 agc atg aac tgg gtc cgc cag gct cca ggg aag ggg ctg gag tgg gtt   144
Ser Met Asn Trp Val Arg Gln Ala Pro Gly Lys Gly Leu Glu Trp Val
         35                  40                  45 tca tac att agt agt aga agt aga acc ata tac tac gca gac tct gtg   192
Ser Tyr Ile Ser Ser Arg Ser Arg Thr Ile Tyr Tyr Ala Asp Ser Val
     50                  55                  60 aag ggc cga ttc acc atc tcc aga gac aat gcc aag aac tca ctg tat   240
Lys Gly Arg Phe Thr Ile Ser Arg Asp Asn Ala Lys Asn Ser Leu Tyr
 65                  70                  75                  80 ctg caa atg aac agc ctg aga gac gag gac acg gct gtg tat tac tgt   288
Leu Gln Met Asn Ser Leu Arg Asp Glu Asp Thr Ala Val Tyr Tyr Cys
                 85                  90                  95 gcg aga gat tac ggt ggt caa ccc cct tac cac tac tac ggt atg       336
Ala Arg Asp Tyr Gly Gly Gln Pro Pro Tyr His Tyr Tyr Gly Met
            100                 105                 110 gac gtc tgg ggc caa ggg acc acg gtc acc gtc tcc tca               375
Asp Val Trp Gly Gln Gly Thr Thr Val Thr Val Ser Ser
        115                 120                 125
```

<210> SEQ ID NO 37
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 37

```
gcc atc cgg atg acc cag tct cca tcc tca ctg tct gca tct gta gga    48
Ala Ile Arg Met Thr Gln Ser Pro Ser Ser Leu Ser Ala Ser Val Gly
 1               5                  10                  15 gac aga gtc acc atc act tgt cgg gcg agt cag ggt att agc agc tgg    96
Asp Arg Val Thr Ile Thr Cys Arg Ala Ser Gln Gly Ile Ser Ser Trp
             20                  25                  30 tta gcc tgg tat cag cag aaa cca gag aaa gcc cct aag tcc ctg atc   144
Leu Ala Trp Tyr Gln Gln Lys Pro Glu Lys Ala Pro Lys Ser Leu Ile
         35                  40                  45 tat gct gca tcc agt ttg caa agt ggg gtc cca tca agg ttc agc ggc   192
Tyr Ala Ala Ser Ser Leu Gln Ser Gly Val Pro Ser Arg Phe Ser Gly
     50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
 65                  70                  75                  80 gaa gat ttt gta act tat tac tgc caa cag tat aat agt tac cct cgg   288
Glu Asp Phe Val Thr Tyr Tyr Cys Gln Gln Tyr Asn Ser Tyr Pro Arg
                 85                  90                  95 acg ttc ggc caa ggg acc aag gtg gaa atc aaa                       321
Thr Phe Gly Gln Gly Thr Lys Val Glu Ile Lys
            100                 105
```

<210> SEQ ID NO 38
<211> LENGTH: 321

<212> TYPE: DNA
<213> ORGANISM: Homo sapiens
<220> FEATURE:
<221> NAME/KEY: CDS
<222> LOCATION: (1)..(321)

<400> SEQUENCE: 38

```
gaa att gtg ctc acc cag tct cca tcc tca ctg tct gca tct gta gga       48
Glu Ile Val Leu Thr Gln Ser Pro Ser Ser Leu Ser Ala Ser Val Gly
 1               5                  10                  15 gac aga gtc acc atc act tgt cgg gcg agt cag ggt att agc agc tgg       96
Asp Arg Val Thr Ile Thr Cys Arg Ala Ser Gln Gly Ile Ser Ser Trp
             20                  25                  30 tta gcc tgg tat cag cag aaa cca gag aaa gcc cct aag tcc ctg atc      144
Leu Ala Trp Tyr Gln Gln Lys Pro Glu Lys Ala Pro Lys Ser Leu Ile
         35                  40                  45 tat gct gca tcc agt ttg caa agt ggg gtc cca cca agg ttc agc ggc      192
Tyr Ala Ala Ser Ser Leu Gln Ser Gly Val Pro Pro Arg Phe Ser Gly
     50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                  70                  75                  80 gaa gat ttt gca act tat tac tgc caa cag tat aat agt tac cct cgg      288
Glu Asp Phe Ala Thr Tyr Tyr Cys Gln Gln Tyr Asn Ser Tyr Pro Arg
                 85                  90                  95 acg ttc ggc caa ggg acc aag gtg gaa atc aaa                          321
Thr Phe Gly Gln Gly Thr Lys Val Glu Ile Lys
            100                 105
```

<210> SEQ ID NO 39
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 39

```
gtc atc tgg gtg acc cag tct cca tcc tca ctg tct gca tct gta gga       48
Val Ile Trp Val Thr Gln Ser Pro Ser Ser Leu Ser Ala Ser Val Gly
 1               5                  10                  15 gac aga gtc acc atc act tgt cgg acg agt cag ggt att agc agc tgg       96
Asp Arg Val Thr Ile Thr Cys Arg Thr Ser Gln Gly Ile Ser Ser Trp
             20                  25                  30 tta gcc tgg tat cag cag aaa cca gag aaa gcc cct gag ctc ctg atc      144
Leu Ala Trp Tyr Gln Gln Lys Pro Glu Lys Ala Pro Glu Leu Leu Ile
         35                  40                  45 tat gct gca tcc agt ttg caa agt ggg gtc cca tca agg ttc agc ggc      192
Tyr Ala Ala Ser Ser Leu Gln Ser Gly Val Pro Ser Arg Phe Ser Gly
     50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                  70                  75                  80 gaa gat ttt gca act tat tac tgc caa cag tat aat agt tac cct cgg      288
Glu Asp Phe Ala Thr Tyr Tyr Cys Gln Gln Tyr Asn Ser Tyr Pro Arg
                 85                  90                  95 acg ttc ggc caa ggg acc aag gtg gaa atc aaa                          321
Thr Phe Gly Gln Gly Thr Lys Val Glu Ile Lys
            100                 105
```

<210> SEQ ID NO 40
<211> LENGTH: 321
<212> TYPE: DNA

```
<213> ORGANISM: Homo sapiens
<220> FEATURE:
<221> NAME/KEY: CDS
<222> LOCATION: (1)..(321)

<400> SEQUENCE: 40 gaa att gtg ctc acc cag tct cca tcc tca ctg tct gca tct gta ggg      48
Glu Ile Val Leu Thr Gln Ser Pro Ser Ser Leu Ser Ala Ser Val Gly
  1               5                  10                  15 gac aga gtc acc atc act tgt cgg gcg agt cag ggt att agc aac tgg      96
Asp Arg Val Thr Ile Thr Cys Arg Ala Ser Gln Gly Ile Ser Asn Trp
             20                  25                  30 tta gcc tgg tat cag cag aaa cca gag aaa gcc cct aag tcc ctg atc     144
Leu Ala Trp Tyr Gln Gln Lys Pro Glu Lys Ala Pro Lys Ser Leu Ile
         35                  40                  45 tat gct gca tcc agt ttg caa agt ggg gtc cca tca agg ttc agc ggc     192
Tyr Ala Ala Ser Ser Leu Gln Ser Gly Val Pro Ser Arg Phe Ser Gly
     50                  55                  60 agt gga tct ggg aca gat ttc act ctc acc atc agc agc ctg cag cct     240
Ser Gly Ser Gly Thr Asp Phe Thr Leu Thr Ile Ser Ser Leu Gln Pro
 65                  70                  75                  80 gaa gat ttt gcg act tat tac tgc caa cag tat aat agt tac cct cgg     288
Glu Asp Phe Ala Thr Tyr Tyr Cys Gln Gln Tyr Asn Ser Tyr Pro Arg
                 85                  90                  95 acg ttc ggc caa ggg acc aag gtg gaa atc aaa                          321
Thr Phe Gly Gln Gly Thr Lys Val Glu Ile Lys
            100                 105

<210> SEQ ID NO 41
<211> LENGTH: 125
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
  1               5                  10                  15

Ser Leu Arg Leu Ser Cys Ala Ala Ala Gly Phe Thr Phe Ser Ser Tyr
             20                  25                  30

Ser Met Asn Trp Val Arg Gln Ala Pro Gly Lys Gly Leu Glu Trp Val
         35                  40                  45

Ser Tyr Ile Ser Ser Arg Ser Arg Thr Ile Tyr Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
        115                 120                 125

<210> SEQ ID NO 42
<211> LENGTH: 125
<212> TYPE: PRT
<213> ORGANISM: Homo sapiens

<400> SEQUENCE: 42

Glu Val Gln Leu Val Glu Ser Gly Gly Gly Leu Val Gln Pro Gly Gly
  1               5                  10                  15

Ser Leu Arg Leu Ser Cys Ala Ala Ala Gly Phe Thr Phe Ser Ser Tyr
```

```
            20                  25                  30
Ser Met Asn Trp Val Arg Gln Ala Pro Gly Lys Gly Leu Glu Trp Val
            35                  40                  45

Ser Tyr Ile Ser Ser Arg Ser Arg Ser Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
                    100                 105                 110

Asp Val Trp Gly Gln Gly Thr Thr Val Thr Val Ser Ser
                115                 120                 125

<210> SEQ ID NO 43
<211> LENGTH: 125
<212> TYPE: PRT
<213> ORGANISM: Homo sapiens

<400> SEQUENCE: 43

Glu Val Gln Leu Val Glu Ser Gly Gly Gly Leu Val Gln Pro Gly Gly
 1               5                  10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Arg Ser Lys Thr Ile Tyr Tyr Ala Asp Ser Val
        50                  55                  60

Lys Gly Arg Phe Thr Ile Ser Arg Asp Asn Ala Arg Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
                    100                 105                 110

Asp Val Trp Gly Gln Gly Thr Thr Val Thr Val Ser Ser
                115                 120                 125

<210> SEQ ID NO 44
<211> LENGTH: 125
<212> TYPE: PRT
<213> ORGANISM: Homo sapiens

<400> SEQUENCE: 44

Glu Val Gln Leu Val Gln Ser Gly Gly Gly Leu Val Gln Pro Gly Gly
 1               5                  10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Arg Ser Arg Thr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr His Tyr Tyr Tyr Gly Met
```

```
              100                 105                 110
Asp Val Trp Gly Gln Gly Thr Thr Val Thr Val Ser Ser
        115                 120                 125

<210> SEQ ID NO 45
<211> LENGTH: 107
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Val Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 46
<211> LENGTH: 107
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 47
<211> LENGTH: 107
<212> TYPE: PRT
<213> ORGANISM: Homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Gly Ile Ser Ser Trp
            20                  25                  30

Leu Ala Trp Tyr Gln Gln Lys Pro Glu Lys Ala Pro Glu Leu Leu Ile
        35                  40                  45
```

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 48
<211> LENGTH: 107
<212> TYPE: PRT
<213> ORGANISM: Homo sapiens

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 49
<211> LENGTH: 98
<212> TYPE: PRT
<213> ORGANISM: Homo sapiens

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg

<210> SEQ ID NO 50
<211> LENGTH: 95
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly

```
1               5                   10                  15
Asp Arg Val Thr Ile Thr Cys Arg Ala Ser Gln Gly Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro
                85                  90                  95
```

<210> SEQ ID NO 51
<211> LENGTH: 352
<212> TYPE: PRT
<213> ORGANISM: Homo sapiens

<400> SEQUENCE: 51

```
Met Glu Gly Ile Ser Ile Tyr Thr Ser Asp Asn Tyr Thr Glu Glu Met
1               5                   10                  15

Gly Ser Gly Asp Tyr Asp Ser Met Lys Glu Pro Cys Phe Arg Glu Glu
                20                  25                  30

Asn Ala Asn Phe Asn Lys Ile Phe Leu Pro Thr Ile Tyr Ser Ile Ile
            35                  40                  45

Phe Leu Thr Gly Ile Val Gly Asn Gly Leu Val Ile Leu Val Met Gly
        50                  55                  60

Tyr Gln Lys Lys Leu Arg Ser Met Thr Asp Lys Tyr Arg Leu His Leu
65                  70                  75                  80

Ser Val Ala Asp Leu Leu Phe Val Ile Thr Leu Pro Phe Trp Ala Val
                85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
            115                 120                 125

Phe Ile Ser Leu Asp Arg Tyr Leu Ala Ile Val His Ala Thr Asn Ser
        130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175

Val Ser Glu Ala Asp Asp Arg Tyr Ile Cys Asp Arg Phe Tyr Pro Asn
                180                 185                 190

Asp Leu Trp Val Val Phe Gln Phe Gln His Ile Met Val Gly Leu
            195                 200                 205

Ile Leu Pro Gly Ile Val Ile Leu Ser Cys Tyr Cys Ile Ile Ile Ser
        210                 215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
                260                 265                 270

Gly Cys Glu Phe Glu Asn Thr Val His Lys Trp Ile Ser Ile Thr Glu
            275                 280                 285
```

```
Ala Leu Ala Phe Phe His Cys Cys Leu Asn Pro Ile Leu Tyr Ala Phe
    290                 295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
                325                 330                 335

His Ser Ser Val Ser Thr Glu Ser Glu Ser Ser Ser Phe His Ser Ser
                340                 345                 350

<210> SEQ ID NO 52
<211> LENGTH: 20
<212> TYPE: PRT
<213> ORGANISM: Homo sapiens

<400> SEQUENCE: 52

Tyr Tyr Tyr Tyr Tyr Gly Met Asp Val Trp Gly Gln Gly Thr Thr Val
1               5                   10                  15

Thr Val Ser Ser
            20

<210> SEQ ID NO 53
<211> LENGTH: 11
<212> TYPE: PRT
<213> ORGANISM: Homo sapiens

<400> SEQUENCE: 53

Thr Phe Gly Gln Gly Thr Lys Val Glu Ile Lys
1               5                   10
```

HUMAN MONOCLONAL ANTIBODIES THAT BIND CXCR4 AND USES THEREOF

BACKGROUND

Chemokines are a family of about 50 small proteins that modulate cell trafficking and angiogenesis and also play a significant role in the tumor microenvironment (Vicari, A. P. and Caux, C. (2002) *Cytokine Growth Factor Rev.* 13:143-154). Depending on their structure, chemokines are classified as C-C chemokines (containing a cysteine-cysteine motif) or C-X-C chemokines (containing a cysteine-X-cysteine motif). Receptors that bind such chemokines thus are classified as members of the CCR family or CXCR family, respectively. One member of the CXCR family is CXCR4, a seven transmembrane G-protein coupled receptor that is predominantly expressed on lymphocytes and that activates chemotaxis. CXCR4 binds the chemokine CXCL12 (SDF-1).

CXCR4 plays a role in embryogenesis, homeostasis and inflammation. Studies with mice engineered to be deficient in CXCR4 or SDF-1 implicate the CXCR4/SDF-1 pathway in organ vascularization, as well as in the immune and hematopoietic systems (Tachibana, K. et al. (1998) *Nature* 393:591-594). Moreover, CXCR4 has been shown to function as a coreceptor for T lymphotrophic HIV-1 isolates (Feng, Y. et al. (1996) *Science* 272:872-877). CXCR4 also has been shown to be expressed on a wide variety of cancer cell types. Additionally, the CXCR4/SDF-1 pathway has been shown to be involved in stimulating the metastatic process in many different neoplasms (Murphy, P. M. (2001) *N. Engl. J. Med.* 345:833-835). For example, CXCR4 and SDF-1 have been shown to mediate organ-specific metastasis by creating a chemotactic gradient between the primary tumor site and the metastatic site (Muller, A. et al. (2001) *Nature* 410:50-56; Murakami, T. et al. (2002) *Cancer Res.* 62:7328-7334; Hanahan, D. et al. (2003) *Cancer Res.* 63:3005-3008).

SUMMARY

The present disclosure provides isolated monoclonal antibodies, in particular human monoclonal antibodies, that bind to human CXCR4 and that exhibit numerous desirable properties. These properties include the ability to bind to native human CXCR4 expressed on a cell surface, the ability to inhibit SDF-1 binding to human CXCR4, the ability to inhibit SDF-1-induced calcium flux in cells expressing CXCR4, the ability to inhibit SDF-1-induced migration of cells expressing CXCR4, the ability to inhibit capillary tube formation by human umbilical vein endothelial cells (HuVECs), the ability to induce apoptosis in cells expressing CXCR4, the ability to inhibit tumor cell proliferation in vitro, the ability to inhibit tumor cell proliferation in vivo, the ability to inhibit metastases of CXCR4$^+$ tumor cells and/or the ability to increase survival time of a CXCR4$^+$ tumor-bearing subject.

In one aspect, the instant disclosure pertains to an isolated human monoclonal antibody, or an antigen-binding portion thereof, wherein the antibody binds to native human CXCR4 expressed on a cell surface. In one embodiment, the antibody also inhibits binding of SDF-1 to human CXCR4, preferably with an $EC_{50}$ for inhibition of 50 nM or less, or 30 nM or less, or 15 nM or less, or 10 nM or less, or 5 nM or less, or 3 nM or less (e.g., an $EC_{50}$ for inhibition of 28.60 nM or less, or 12.51 nM or less, or 2.256 nM or less). In another embodiment, the antibody also binds to native human CXCR4 expressed on a cell surface but does not inhibit binding of SDF-1 to human CXCR4. In yet other embodiments, the antibody also inhibits SDF-1-induced calcium flux in cells expressing human CXCR4, preferably with an $EC_{50}$ for inhibition of 3 nM or less, or 2 nM or less, or 1 nM or less, or 0.9 nM or less, or 0.8 nM or less, or 0.7 nM or less, or 0.6 nM or less, or 0.5 nM or less, or 0.4 nM or less (e.g., 0.9046 nM or less, 0.5684 or less, or 0.3219 nM or less). In yet other embodiments, the antibody also inhibits SDF-1-induced migration of cells expressing human CXCR4, preferably with an $EC_{50}$ for inhibition of 50 nM or less, or 30 nM or less, or 20 nM or less, or 15 nM or less (e.g., 18.99 nM or less, or 12.44 or less). In still other embodiments, the antibody also inhibits capillary tube formation by HuVECs, induces apoptosis of cells expressing CXCR4, inhibits tumor cell proliferation in vitro, inhibits tumor cell proliferation or induces tumor cell apoptosis in vivo, inhibits metastases of CXCR4$^+$ tumor cells and/or increases survival time of a CXCR4$^+$ tumor-bearing subject.

Preferably, the antibody binds to human CXCR4 with high affinity, such as with a $K_D$ of $1\times10^{-7}$ M or less or with a $K_D$ of $5\times10^{-8}$ M or less. Preferably, the antibodies of this disclosure are full-length antibodies (i.e., comprising variable and constant regions). Furthermore, the antibodies of this disclosure preferably are raised against full-length human CXCR-4 expressed in its native conformation on a host cell or in an artificial membrane.

In a preferred aspect, this disclosure pertains to an isolated human monoclonal antibody, or an antigen-binding portion thereof, wherein the antibody:
   (a) binds to native human CXCR4 expressed on a cell surface;
   (b) inhibits binding of SDF-1 to human CXCR4;
   (c) inhibits SDF-1-induced calcium flux in cells expressing human CXCR4;
   (d) inhibits SDF-1-induced migration of cells expressing human CXCR4; and
   (e) inhibits capillary tube formation by human umbilical vein endothelial cells.

Even more preferably, the antibody also induces apoptosis of cells expressing human CXCR4 and/or inhibits growth of CXCR4$^+$ tumor cells and/or induces tumor cell apoptosis in vivo.

In another aspect, this disclosure pertains to an isolated human monoclonal antibody, or antigen binding portion thereof, wherein the antibody cross-competes for binding to CXCR4 with a reference antibody, wherein the reference antibody comprises:
   (a) a heavy chain variable region comprising the amino acid sequence of SEQ ID NO: 25 and a light chain variable region comprising the amino acid sequence of SEQ ID NO: 29; or
   (b) a heavy chain variable region comprising the amino acid sequence of SEQ ID NO: 26 and a light chain variable region comprising the amino acid sequence of SEQ ID NO: 30; or
   (c) a heavy chain variable region comprising the amino acid sequence of SEQ ID NO: 27 and a light chain variable region comprising the amino acid sequence of SEQ ID NO: 31; or
   (d) a heavy chain variable region comprising the amino acid sequence of SEQ ID NO: 28 and a light chain variable region comprising the amino acid sequence of SEQ ID NO: 32.

In certain embodiments, this disclosure provides an isolated monoclonal antibody, or an antigen-binding portion thereof, comprising a heavy chain variable region that is the product of or derived from a human $V_H$ 3-48 gene, wherein the antibody specifically binds human CXCR4. In other embodiments, this disclosure provides an isolated monoclonal antibody, or an antigen-binding portion thereof, comprising a light chain variable region that is the product of or derived from a human $V_K$ L15 gene, wherein the antibody specifically binds human CXCR4. In yet other embodiments, this disclosure provides an isolated monoclonal antibody, or an antigen-binding portion thereof, comprising a heavy chain variable region that is the product of or derived from a human $V_H$ 3-48 gene and a light chain variable region that is the product of or derived from a human $V_K$ L15 gene, wherein the antibody specifically binds human CXCR4.

In another aspect, this disclosure provides an isolated monoclonal antibody, or antigen binding portion thereof, comprising:

a heavy chain variable region that comprises CDR1, CDR2, and CDR3 sequences; and a light chain variable region that comprises CDR1, CDR2, and CDR3 sequences, wherein:

(a) the heavy chain variable region CDR3 sequence comprises an amino acid sequence selected from the group consisting of amino acid sequences of SEQ ID NOs: 9-12, and conservative modifications thereof;

(b) the light chain variable region CDR3 sequence comprises an amino acid sequence selected from the group consisting of amino acid sequence of SEQ ID NOs: 21-24, and conservative modifications thereof; and (c) the antibody binds to native human CXCR4 expressed on a cell surface. In preferred embodiments, this antibody also has one or more of the following characteristics: inhibits binding of SDF-1 to CXCR4, inhibits SDF-1-induced calcium flux in cells expressing CXCR4, inhibits SDF-1-induced migration of cells expressing CXCR-4; inhibits capillary tube formation by HuVECs; induces apoptosis in cells expressing CXCR4 (in vitro and/or in vivo), inhibits growth of CXCR4$^+$ tumor cells in vitro and/or in vivo, and/or inhibits metatases of CXCR4$^+$ tumor cells.

Preferably, the heavy chain variable region CDR2 sequence comprises an amino acid sequence selected from the group consisting of amino acid sequences of SEQ ID NOs: 5-8, and conservative modifications thereof; and the light chain variable region CDR2 sequence comprises an amino acid sequence selected from the group consisting of amino acid sequences of SEQ ID NOs: 17-20, and conservative modifications thereof. Preferably, the heavy chain variable region CDR1 sequence comprises an amino acid sequence selected from the group consisting of amino acid sequences of SEQ ID NOs: 1-4, and conservative modifications thereof; and the light chain variable region CDR1 sequence comprises an amino acid sequence selected from the group consisting of amino acid sequences of SEQ ID NOs: 13-16, and conservative modifications thereof.

A preferred combination comprises:
(a) heavy chain variable region CDR1 comprising SEQ ID NO: 1;
(b) a heavy chain variable region CDR2 comprising SEQ ID NO: 5;
(c) a heavy chain variable region CDR3 comprising SEQ ID NO: 9;
(d) a light chain variable region CDR1 comprising SEQ ID NO: 13;
(e) a light chain variable region CDR2 comprising SEQ ID NO: 17; and
(f) a light chain variable region CDR3 comprising SEQ ID NO: 21.

Another preferred combination comprises:
(a) a heavy chain variable region CDR1 comprising SEQ ID NO: 2;
(b) a heavy chain variable region CDR2 comprising SEQ ID NO: 6;
(c) a heavy chain variable region CDR3 comprising SEQ ID NO: 10;
(d) a light chain variable region CDR1 comprising SEQ ID NO: 14;
(e) a light chain variable region CDR2 comprising SEQ ID NO: 18; and
(f) a light chain variable region CDR3 comprising SEQ ID NO: 22.

Another preferred combination comprises:
(a) a heavy chain variable region CDR1 comprising SEQ ID NO: 3;
(b) a heavy chain variable region CDR2 comprising SEQ ID NO: 7;
(c) a heavy chain variable region CDR3 comprising SEQ ID NO: 11;
(d) a light chain variable region CDR1 comprising SEQ ID NO: 15;
(e) a light chain variable region CDR2 comprising SEQ ID NO: 19; and
(f) a light chain variable region CDR3 comprising SEQ ID NO: 23.

Another preferred combination comprises:
(a) a heavy chain variable region CDR1 comprising SEQ ID NO: 4;
(b) a heavy chain variable region CDR2 comprising SEQ ID NO: 8;
(c) a heavy chain variable region CDR3 comprising SEQ ID NO: 12;
(d) a light chain variable region CDR1 comprising SEQ ID NO: 16;
(e) a light chain variable region CDR2 comprising SEQ ID NO: 20; and
(f) a light chain variable region CDR3 comprising SEQ ID NO: 24.

Other preferred antibodies of this disclosure, or antigen binding portions thereof, comprise: (a) a heavy chain variable region comprising an amino acid sequence selected from the group consisting of SEQ ID NOs: 25-28 and 41-44; and (b) a light chain variable region comprising an amino acid sequence selected from the group consisting of SEQ ID NOs: 29-32 and 45-48; wherein the antibody specifically binds CXCR4.

A preferred combination comprises: (a) a heavy chain variable region comprising the amino acid sequence of SEQ ID NO: 25 or 41; and (b) a light chain variable region comprising the amino acid sequence of SEQ ID NO: 29 or 45.

Another preferred combination comprises: (a) a heavy chain variable region comprising the amino acid sequence of SEQ ID NO: 26 or 42; and (b) a light chain variable region comprising the amino acid sequence of SEQ ID NO: 30 or 46.

Another preferred combination comprises: (a) a heavy chain variable region comprising the amino acid sequence of SEQ ID NO: 27 or 43; and (b) a light chain variable region comprising the amino acid sequence of SEQ ID NO: 31 or 47.

Another preferred combination comprises: (a) a heavy chain variable region comprising the amino acid sequence of SEQ ID NO: 28 or 44; and (b) a light chain variable region comprising the amino acid sequence of SEQ ID NO: 32 or 48.

In another aspect of this disclosure, antibodies, or antigen-binding portions thereof, are provided that compete for binding to CXCR4 with any of the aforementioned antibodies.

The antibodies of this disclosure can be, for example, full-length antibodies, for example of an IgG1 or IgG4 isotype. Alternatively, the antibodies can be antibody fragments, such as Fab, Fab' or Fab'2 fragments, or single chain antibodies.

This disclosure also provides an immunoconjugate comprising an antibody of this disclosure, or antigen-binding portion thereof, linked to a therapeutic agent, such as a cytotoxin or a radioactive isotope. This disclosure also provides a bispecific molecule comprising an antibody, or antigen-binding portion thereof, of this disclosure, linked to a second functional moiety having a different binding specificity than said antibody, or antigen binding portion thereof.

Compositions comprising an antibody, or antigen-binding portion thereof, or immunoconjugate or bispecific molecule of this disclosure and a pharmaceutically acceptable carrier are also provided.

Nucleic acid molecules encoding the antibodies, or antigen-binding portions thereof, of this disclosure are also encompassed by this disclosure, as well as expression vectors comprising such nucleic acids and host cells comprising such expression vectors. Methods for preparing anti-CXCR4 antibodies using the host cells comprising such expression vectors are also provided and may include the steps of (i) expressing the antibody in the host cell and (ii) isolating the antibody from the host cell.

Another aspect of this disclosure pertains to methods of modulating CXCR4 activity in a cell, wherein the cells are contacted with an antibody, or antigen-binding portion thereof, of this disclosure. The cells can be contacted in vitro by culturing the cells with the antibody or the cells can be contacted in vivo by administering the antibody to a subject. In a preferred embodiment, the cells are tumor cells expressing CXCR4 and the method results in inhibition of the growth of tumor cells and/or inhibition of metastasis of the tumor cells. In another embodiment, the cells are T cells expressing CXCR4 and the method results in inhibition of entry of HIV into the cells. In yet another embodiment, the cells are lymphocytes in an inflammatory disorder and the methods result in inhibition of inflammation. In yet another embodiment, the cells are involved in vascularization and the method results in modulation of angiogenesis.

In another aspect, this disclosure pertains to a method of stimulating mobilization of $CD34^+$ stem cells from bone marrow to peripheral blood in a subject, the method comprising administering to the subject an antibody, or antigen-binding portion thereof, of this disclosure such that mobilization of $CD34^+$ stem cells from bone marrow to peripheral blood is stimulated. The method can further comprise collecting the $CD34^+$ stem cells from the peripheral blood, such as for use in autologous stem cell transplantation.

Other features and advantages of the instant disclosure will be apparent from the following detailed description and examples, which should not be construed as limiting. The contents of all references, Genbank entries, patents and published patent applications cited throughout this application are expressly incorporated herein by reference.

BRIEF DESCRIPTION OF THE DRAWINGS

FIG. 1A shows the nucleotide sequence (SEQ ID NO: 33) and amino acid sequence (SEQ ID NO: 25) of the heavy chain variable region of the F7 human monoclonal antibody. The CDR1 (SEQ ID NO: 1), CDR2 (SEQ ID NO: 5) and CDR3 (SEQ ID NO: 9) regions are delineated and the V, D and J germline derivations are indicated.

FIG. 1B shows the nucleotide sequence (SEQ ID NO: 37) and amino acid sequence (SEQ ID NO: 29) of the light chain variable region of the F7 human monoclonal antibody. The CDR1 (SEQ ID NO: 13), CDR2 (SEQ ID NO: 17) and CDR3 (SEQ ID NO: 21) regions are delineated and the V and J germline derivations are indicated.

FIG. 2A shows the nucleotide sequence (SEQ ID NO: 34) and amino acid sequence (SEQ ID NO: 26) of the heavy chain variable region of the F9 human monoclonal antibody. The CDR1 (SEQ ID NO: 2), CDR2 (SEQ ID NO: 6) and CDR3 (SEQ ID NO: 10) regions are delineated and the V, D and J germline derivations are indicated.

FIG. 2B shows the nucleotide sequence (SEQ ID NO: 38) and amino acid sequence (SEQ ID NO: 30) of the light chain variable region of the F9 human monoclonal antibody. The CDR1 (SEQ ID NO: 14), CDR2 (SEQ ID NO: 18) and CDR3 (SEQ ID NO: 22) regions are delineated and the V and J germline derivations are indicated.

FIG. 3A shows the nucleotide sequence (SEQ ID NO: 35) and amino acid sequence (SEQ ID NO: 27) of the heavy chain variable region of the D1 human monoclonal antibody. The CDR1 (SEQ ID NO: 3), CDR2 (SEQ ID NO: 7) and CDR3 (SEQ ID NO: 11) regions are delineated and the V, D and J germline derivations are indicated.

FIG. 3B shows the nucleotide sequence (SEQ ID NO: 39) and amino acid sequence (SEQ ID NO: 31) of the light chain variable region of the D1 human monoclonal antibody. The CDR1 (SEQ ID NO: 15), CDR2 (SEQ ID NO: 19) and CDR3 (SEQ ID NO: 23) regions are delineated and the V and J germline derivations are indicated.

FIG. 4A shows the nucleotide sequence (SEQ ID NO: 36) and amino acid sequence (SEQ ID NO: 28) of the heavy chain variable region of the E2 human monoclonal antibody. The CDR1 (SEQ ID NO: 4), CDR2 (SEQ ID NO: 8) and CDR3 (SEQ ID NO: 12) regions are delineated and the V, D and J germline derivations are indicated.

FIG. 4B shows the nucleotide sequence (SEQ ID NO: 40) and amino acid sequence (SEQ ID NO: 32) of the light chain variable region of the E2 human monoclonal antibody. The CDR1 (SEQ ID NO: 16), CDR2 (SEQ ID NO: 20) and CDR3 (SEQ ID NO: 24) regions are delineated and the V and J germline derivations are indicated.

FIG. 5A shows the alignment of the amino acid sequence of the heavy chain variable regions of F7 (SEQ ID NO: 25) and F7GL (SEQ ID NO: 41) with the human germline $V_H$ 3-48 amino acid sequence (SEQ ID NO: 49) (JH6b germline disclosed as SEQ ID NO: 52).

FIG. 5B shows the alignment of the amino acid sequence of the light chain variable region of F7 (SEQ ID NO: 29) and F7GL (SEQ ID NO: 45) with the human germline $V_k$ L15 amino acid sequence (SEQ ID NO:50) (JK1 germline disclosed as SEQ ID NO: 53).

FIG. 6A shows the alignment of the amino acid sequence of the heavy chain variable regions of F9 (SEQ ID NO: 26) and F9GL (SEQ ID NO: 42) with the human germline $V_H$ 3-48 amino acid sequence (SEQ ID NO: 49) (JH6b germline disclosed as SEQ ID NO: 52).

FIG. 6B shows the alignment of the amino acid sequence of the light chain variable region of F9 (SEQ ID NO: 30) and F9GL (SEQ ID NO: 46) with the human germline $V_k$ L15 amino acid sequence (SEQ ID NO:50) (JK1 germline disclosed as SEQ ID NO: 53).

FIG. 7A shows the alignment of the amino acid sequence of the heavy chain variable regions of D1 (SEQ ID NO: 27)

and D1GL (SEQ ID NO: 43) with the human germline $V_H$ 3-48 amino acid sequence (SEQ ID NO: 49) (JH6b germline disclosed as SEQ ID NO: 52).

FIG. 7B shows the alignment of the amino acid sequence of the light chain variable region of D1 (SEQ ID NO: 31) and D1GL (SEQ ID NO: 47) with the human germline $V_k$ L15 amino acid sequence (SEQ ID NO:50) (JK1 germline disclosed as SEQ ID NO: 53).

FIG. 8A shows the alignment of the amino acid sequence of the heavy chain variable regions of E2 (SEQ ID NO: 28) and E2GL (SEQ ID NO: 44) with the human germline $V_H$ 3-48 amino acid sequence (SEQ ID NO: 49) (JH6b germline disclosed as SEQ ID NO: 52).

FIG. 8B shows the alignment of the amino acid sequence of the light chain variable region of E2 (SEQ ID NO: 32) and E2GL (SEQ ID NO: 48) with the human germline $V_k$ L15 amino acid sequence (SEQ ID NO:50) (JK1 germline disclosed as SEQ ID NO: 53).

Figure 9:
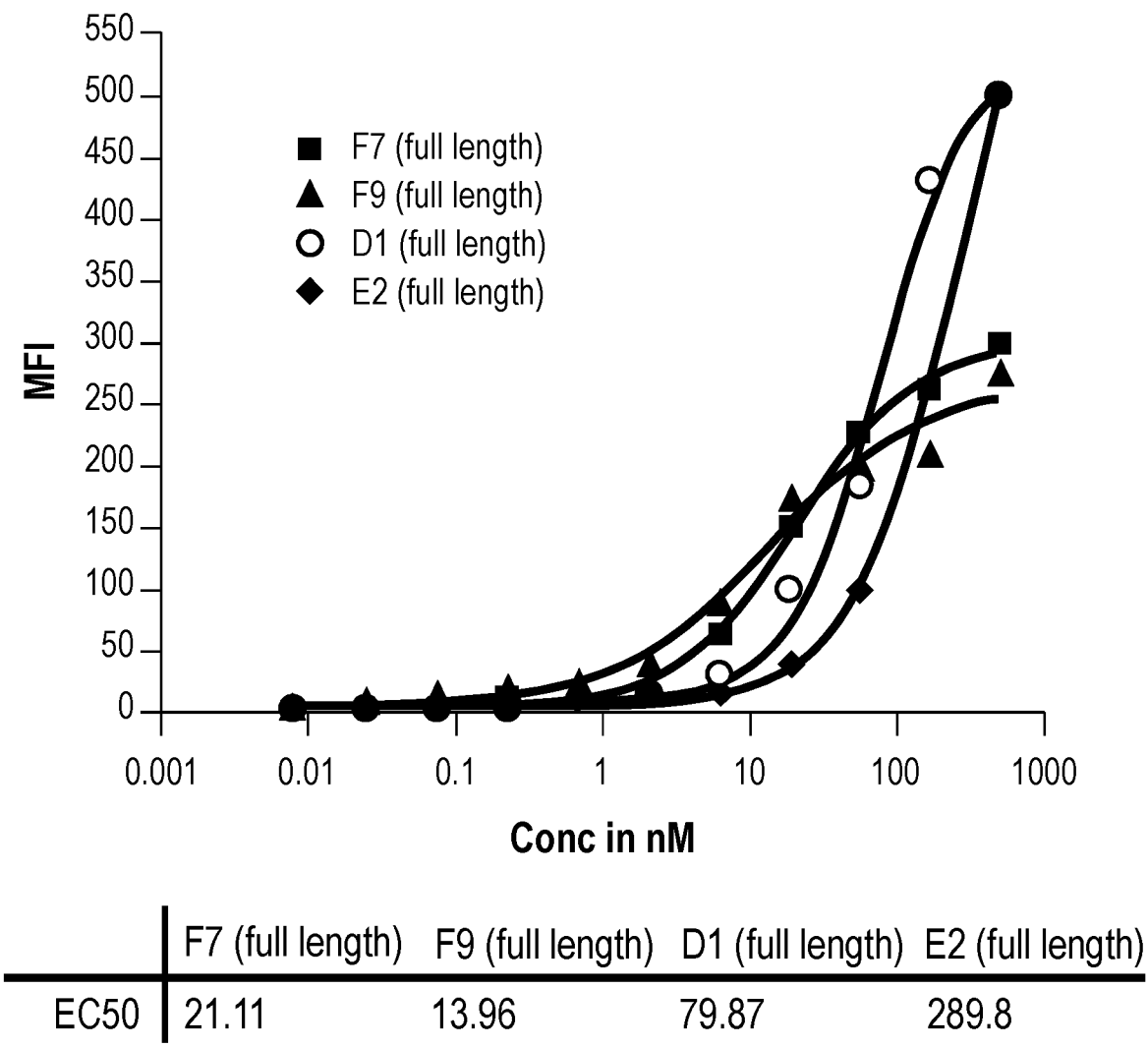

FIG. 9 is a graph showing the binding of anti-CXCR4 human antibodies F7, F9, D1 and E2 to CEM cells that express native human CXCR4 on the cell surface.

Figure 10:
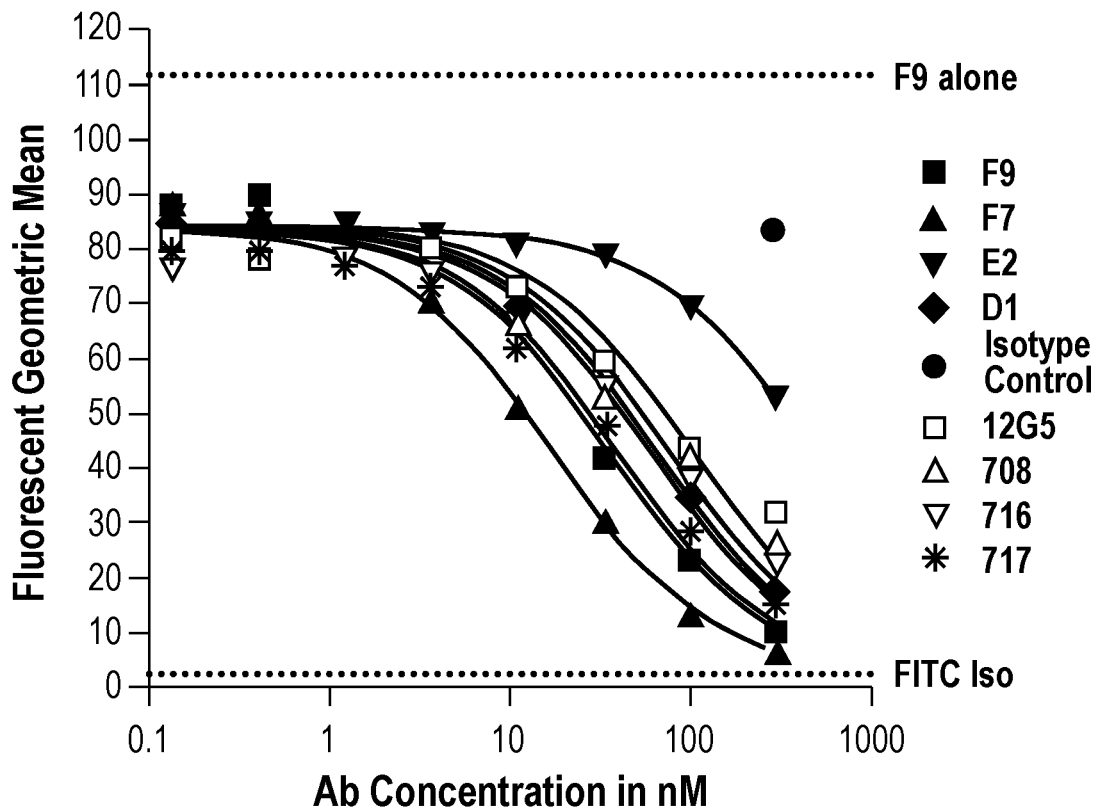

FIG. 10 is a graph showing antibody competition for binding to CEM cells between FITC-labeled anti-CXCR4 antibody F9 and a panel of unlabeled anti-CXCR4 human antibodies.

Figure 11:
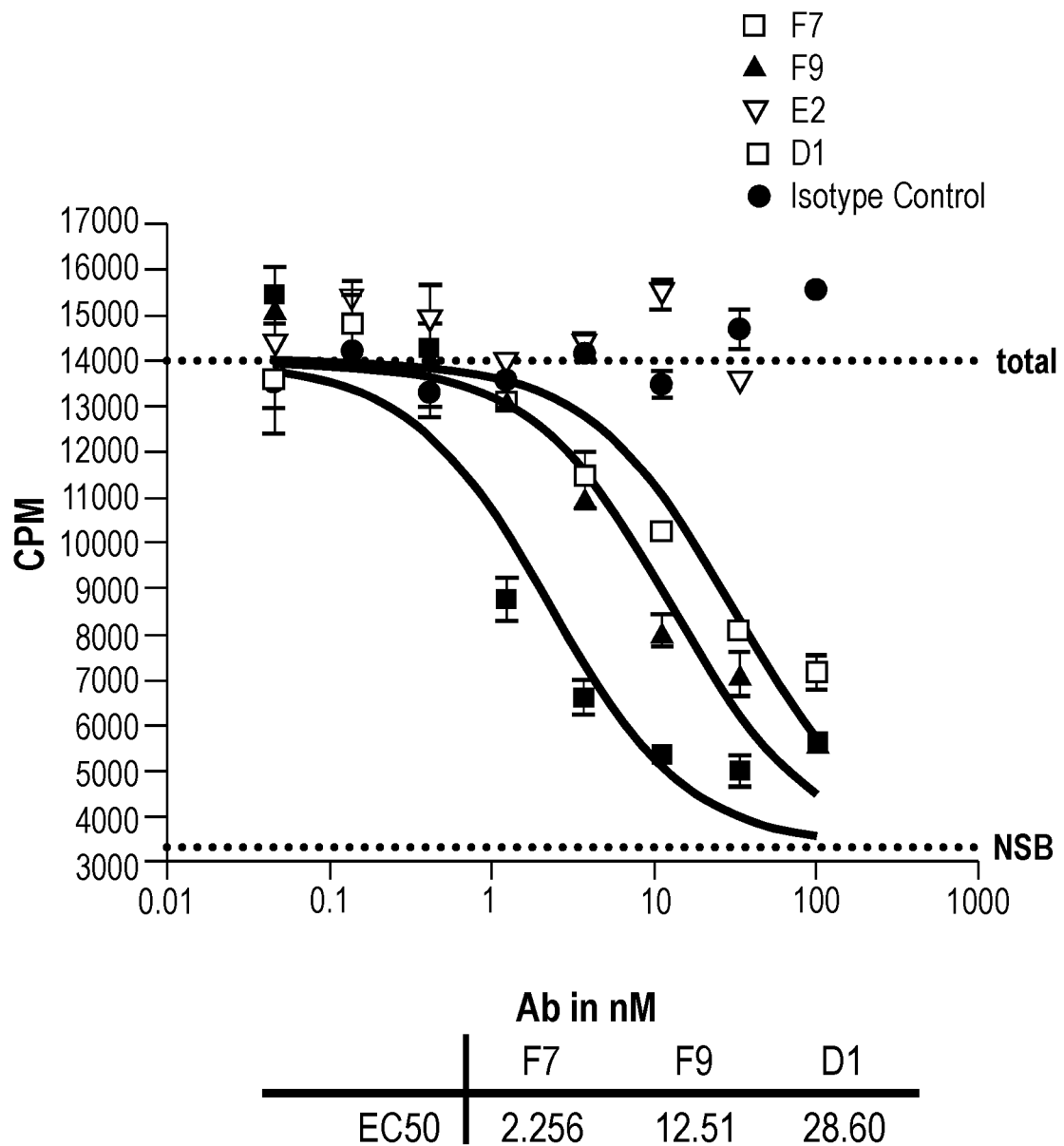

FIG. 11 is a graph showing inhibition of binding of $^{125}$I-labeled SDF-1 to CEM cells by anti-CXCR4 human antibodies F7, F9 and D1.

Figure 12:
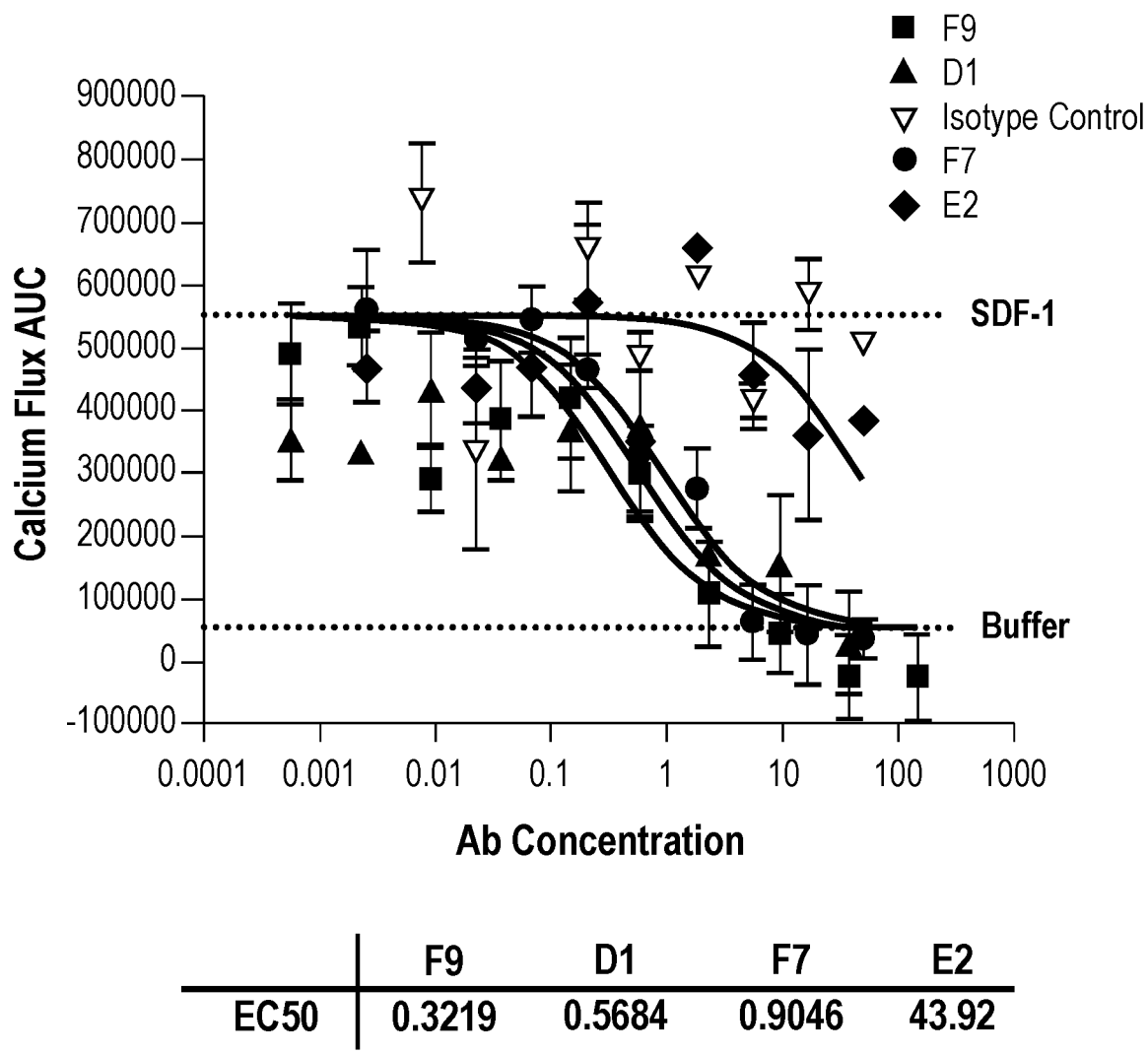

FIG. 12 is a graph showing inhibition of SDF-1-induced calcium flux in CEM cells by anti-CXCR4 human antibodies F7, F9 and D1.

Figure 13:
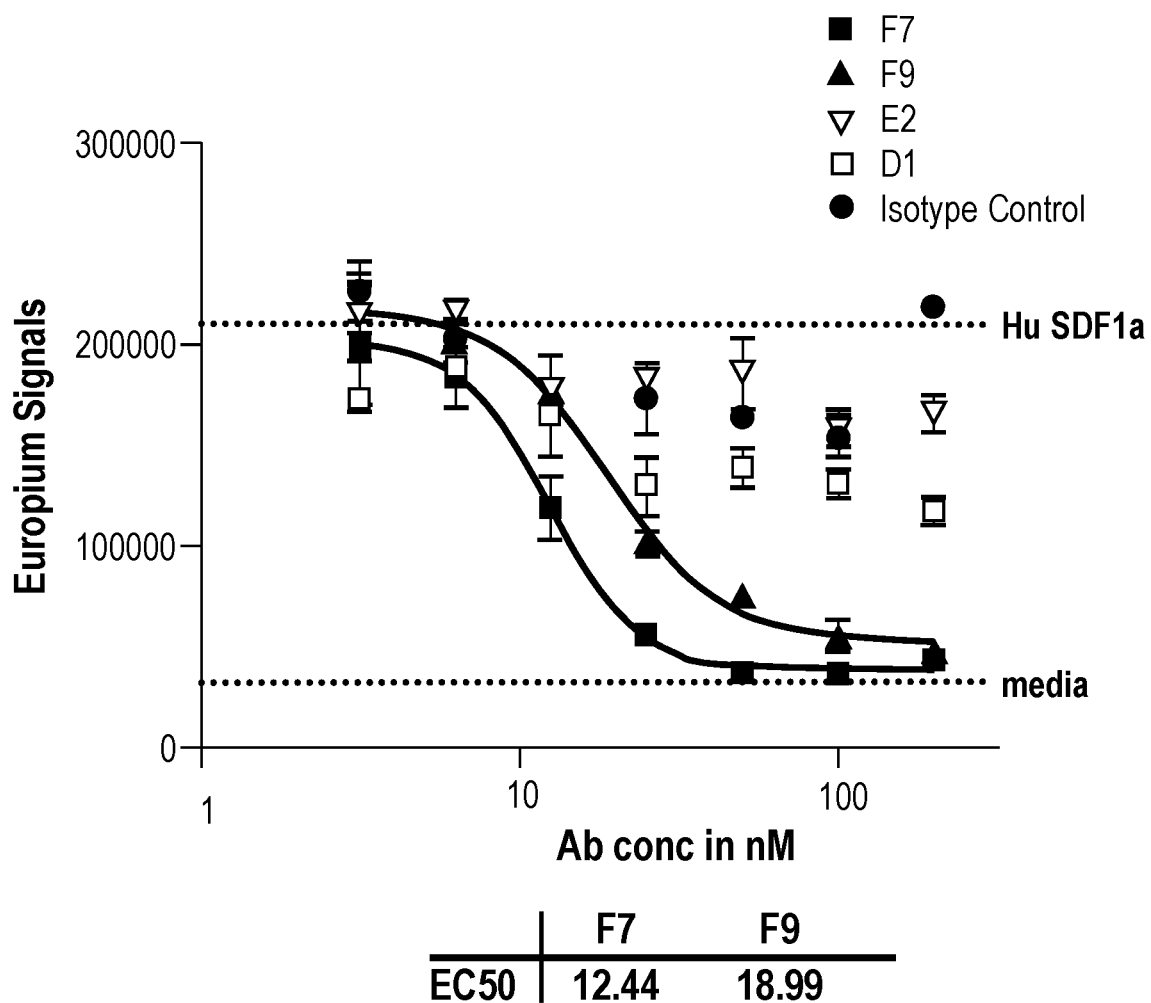

FIG. 13 is a graph showing inhibition of SDF-1-induced migration of CEM cells by anti-CXCR4 human antibodies F7 and F9.

Figure 14:
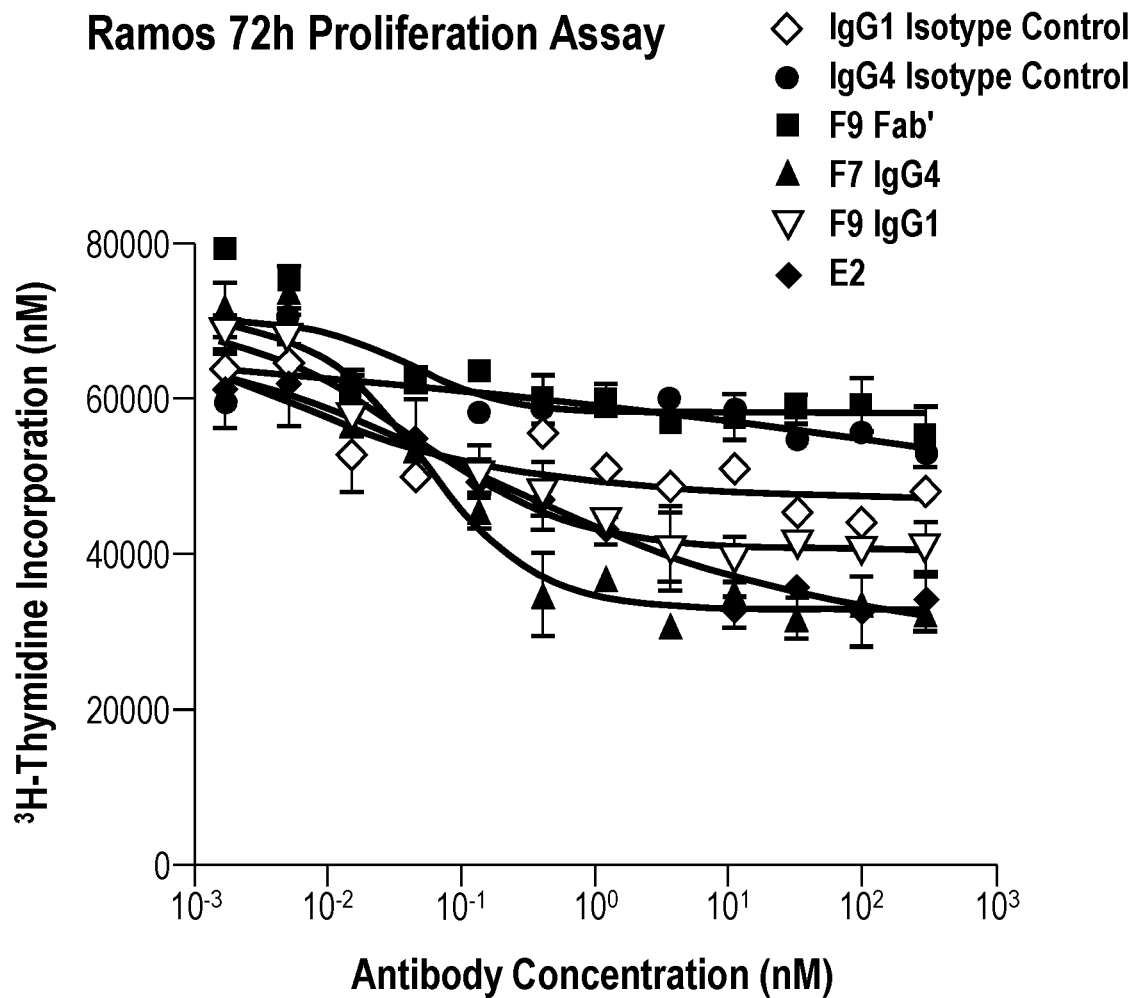

FIG. 14 is a graph showing inhibition of Ramos tumor cell proliferation in vitro by anti-CXCR4 human antibodies F7, F9 and E2.

Figure 15A:
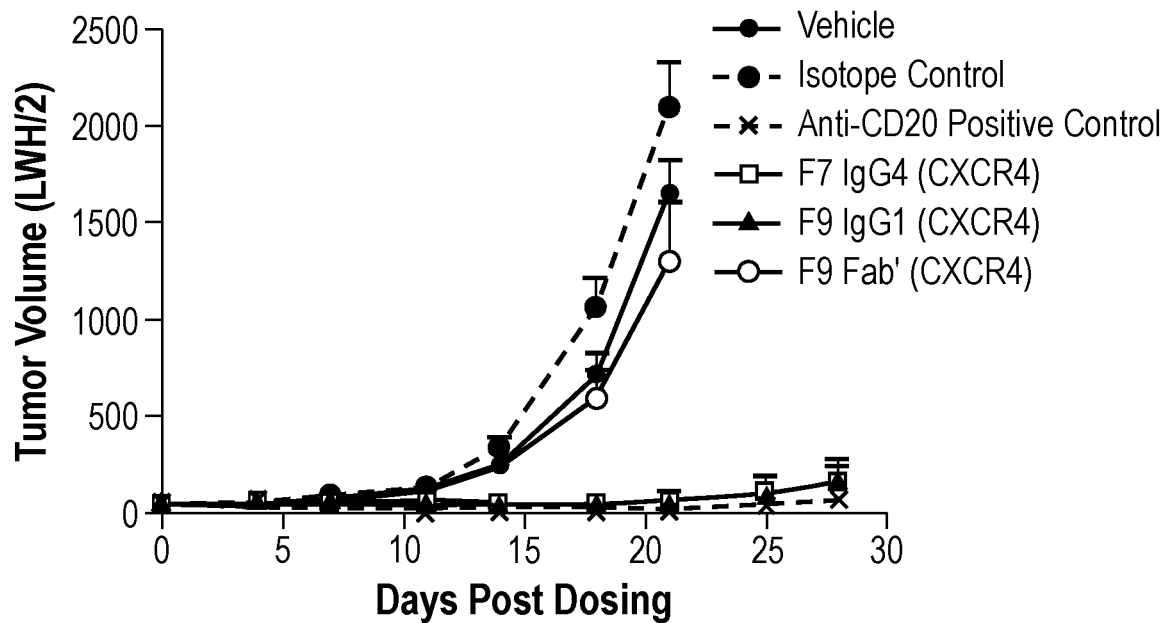
Figure 15B:
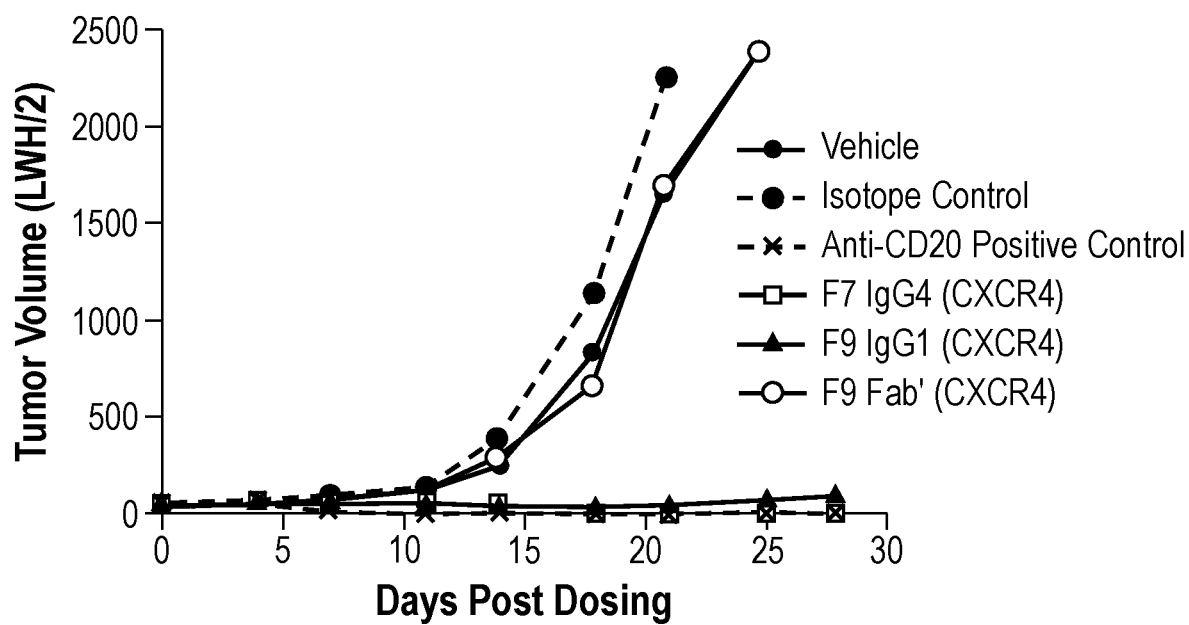
Figure 15C:
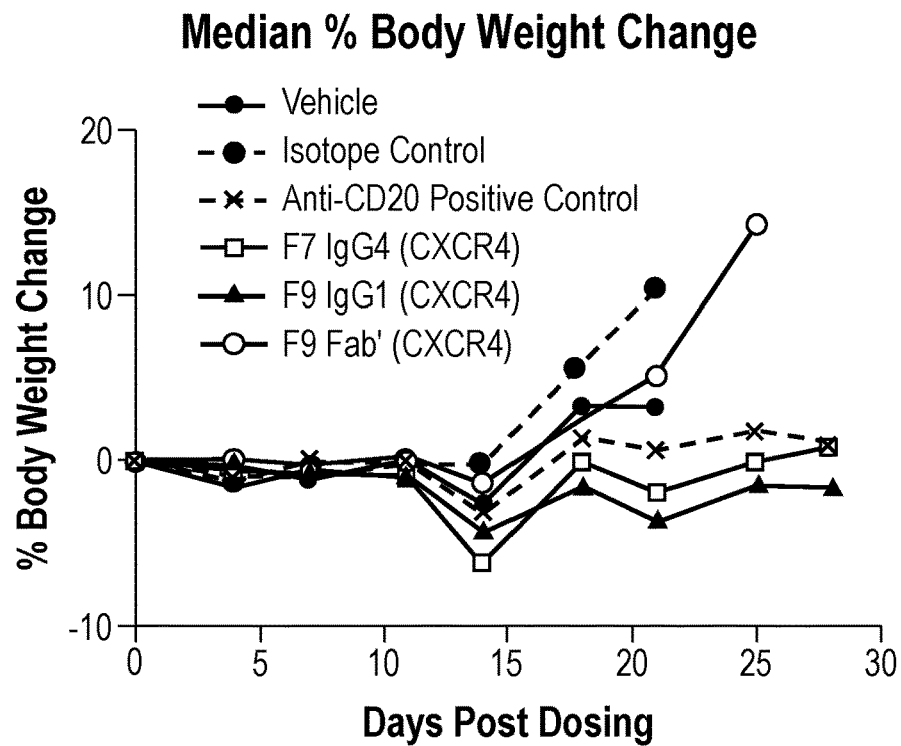

FIGS. 15A-C are graphs showing inhibition of Ramos tumor cell proliferation in vivo in a subcutaneous tumor model by anti-CXCR4 human antibodies F7 and F9. FIG. 15A shows the mean tumor volume growth curve; FIG. 15B shows the median tumor volume growth curve; FIG. 15C shows the median % body weight change.

Figure 16:
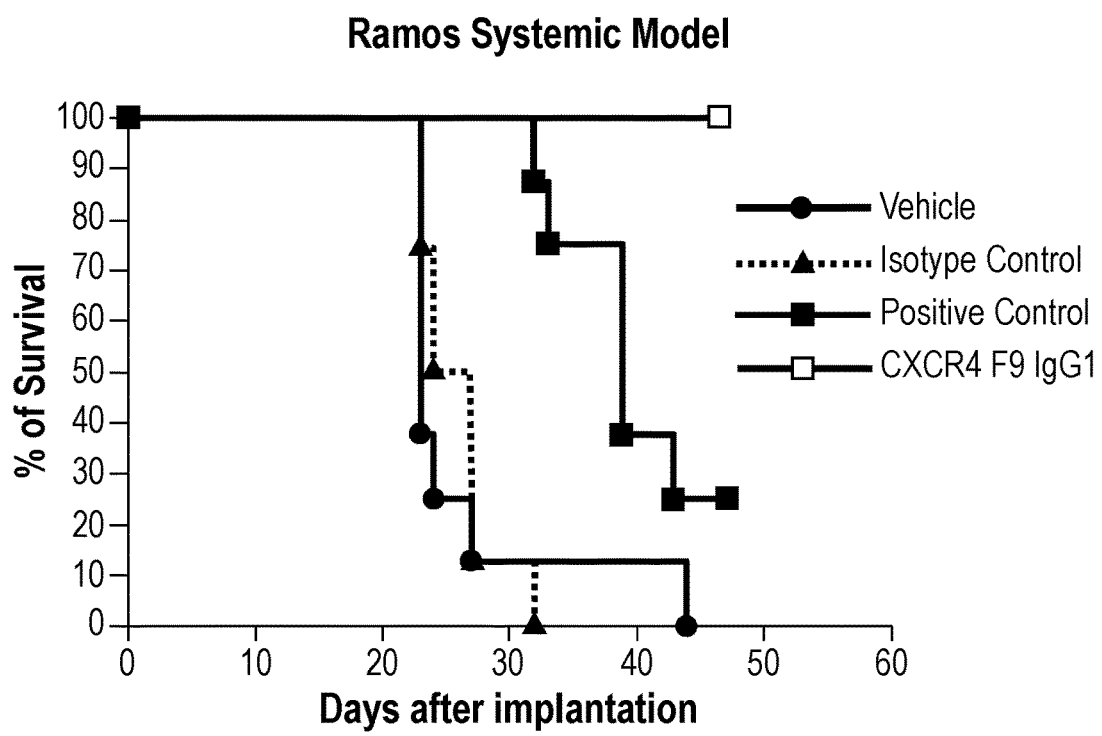

FIG. 16 is a graph showing % survival of mice treated with the anti-CXCR4 human antibody F9 in a Ramos systemic tumor cell model.

DETAILED DESCRIPTION OF THIS DISCLOSURE

The present disclosure relates to isolated monoclonal antibodies, particularly human monoclonal antibodies, which bind specifically to native human CXCR4 expressed on a cell surface. In certain embodiments, the antibodies of this disclosure are derived from particular heavy and light chain germline sequences and/or comprise particular structural features such as CDR regions comprising particular amino acid sequences. This disclosure provides isolated antibodies, methods of making such antibodies, immunoconjugates and bispecific molecules comprising such antibodies and pharmaceutical compositions containing the antibodies, immunoconjugates or bispecific molecules of this disclosure. This disclosure also relates to methods of using the antibodies, such as to detect CXCR4, as well as to modulate CXCR4 activity in diseases or disorders associated with expression of CXCR4 or involving the CXCR4/SDF-1 pathway, such as cancers, tumor metastasis, HIV infection, inflammation and angiogenesis. Accordingly, this disclosure also provides methods of using the anti-CXCR4 antibodies of this disclosure to treat cancer, for example, to treat a cancer such as breast, ovarian, prostate, non-small cell lung, pancreatic, thyroid, melanoma, nasopharyngeal, renal cell, lymphoma, neuroblastoma, glioblastoma, rhabdomyosarcoma, colorectal, kidney, osteosarcoma, acute lymphoblastic leukemia or acute myeloid leukemia. Additionally, this disclosure provides methods of using the anti-CXCR4 antibodies of this disclosure to inhibit tumor metastasis.

In order that the present disclosure may be more readily understood, certain terms are first defined. Additional definitions are set forth throughout the detailed description.

The term "CXCR4" includes variants, isoforms, homologs, orthologs and paralogs. For example, antibodies specific for CXCR4 may, in certain cases, cross-react with CXCR4 from species other than human. In other embodiments, the antibodies specific for human CXCR4 may be completely specific for human CXCR4 and may not exhibit species or other types of cross-reactivity. The term "human CXCR4" refers to human sequence CXCR4, such as the complete amino acid sequence of human CXCR4 having Genbank accession number P61073 (SEQ ID NO.:51). CXCR4 is also known in the art as, for example, LESTR, Fusin or CD184. The human CXCR4 sequence may differ from human CXCR4 of SEQ ID NO.:51 by having, for example, conserved mutations or mutations in non-conserved regions and the CXCR4 has substantially the same biological function as the human CXCR4 of SEQ ID NO.: 51. For example, a biological function of human CXCR4 is having an epitope in the extracellular domain of CXCR4 that is specifically bound by an antibody of the instant disclosure or the biological function of human CXCR4 is chemokine binding or involvement in the metastatic process.

A particular human CXCR4 sequence will generally be at least 90% identical in amino acids sequence to human CXCR4 of SEQ ID NO.:51 and contains amino acid residues that identify the amino acid sequence as being human when compared to CXCR4 amino acid sequences of other species (e.g., murine). In certain cases, a human CXCR4 may be at least 95%, or even at least 96%, 97%, 98%, or 99% identical in amino acid sequence to CXCR4 of SEQ ID NO.:51. In certain embodiments, a human CXCR4 sequence will display no more than 10 amino acid differences from the CXCR4 of SEQ ID NO.:51. In certain embodiments, the human CXCR4 may display no more than 5, or even no more than 4, 3, 2, or 1 amino acid difference from the CXCR4 of SEQ ID NO.:51. Percent identity can be determined as described herein.

The term "SDF-1" refers to stromal cell-derived factor 1, which is a ligand for CXCR4. The term "SDF-1" encompasses different isoforms of SDF-1, such as SDF-1α and SDF-1β. The amino acid sequence of human SDF-1α has Genbank accession number NP 954637. The amino acid sequence of human SDF-1β has Genbank accession number NP 000600. Human SDF-1 is also described in U.S. Pat. No. 5,756,084. SDF-1 is also known as CXCL12. The amino acid sequence of human SDF-1 can differ from the SDF-1 of NP 954637 or NP 000600, as described herein for CXCR4.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a "cell surface receptor" of the present disclosure is the CXCR4 receptor.

The term "antibody" as referred to herein includes whole antibodies and any antigen binding fragment (i.e., "antigen-binding portion") or single chains thereof. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion"), as used herein, refers to one or more fragments of an antibody that retain the ability to specifically bind to an antigen (e.g., CXCR4). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds CXCR4 is substantially free of antibodies that specifically bind antigens other than CXCR4). An isolated antibody that specifically binds CXCR4 may, however, have cross-reactivity to other antigens, such as CXCR4 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of this disclosure may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human CXCR4" is intended to refer to an antibody that binds to human CXCR4 (and possibly CXCR4 from one or more non-human species) but does not substantially bind to non-CXCR4 proteins. In certain embodiments, an antibody of the instant disclosure specifically binds to human CXCR4 of SEQ ID NO.:51 or a variant thereof. Preferably, the antibody binds to human CXCR4 with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, even more preferably $5 \times 10^{-9}$ M or less.

The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

As used herein, the term "high affinity" for an IgG antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-6}$ M or less, even more preferably $10^{-8}$ M or less.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

Various aspects of this disclosure are described in further detail in the following subsections.

Anti-CXCR4 Antibodies

The antibodies of this disclosure are characterized by particular functional features or properties of the antibodies. For example, the antibodies bind to native human CXCR4 expressed on a cell surface. Preferably, an antibody of this disclosure binds to CXCR4 with high affinity, for example with a $K_D$ of $1 \times 10^{-7}$ M or less. The anti-CXCR4 antibodies of this disclosure preferably exhibit one or more of the following characteristics:

(a) binding to native human CXCR4 expressed on a cell surface;
(b) inhibiting binding of SDF-1 to CXCR4;
(c) inhibiting SDF-1-induced calcium flux in cells expressing CXCR4;
(d) inhibiting SDF-1-induced migration of cells expressing CXCR4;
(e) inhibiting capillary tube formation by human umbilical vein endothelial cells;
(f) binding to human CXCR4 with a $K_D$ of $1 \times 10^{-7}$ M or less;
(g) inducing apoptosis in cells expressing CXCR4;
(h) inhibiting tumor cell proliferation in vitro;
(i) inhibiting tumor cell proliferation and/or inducing tumor cell apoptosis in vivo;
(j) inhibiting metastases of CXCR4+ tumor cells; and/or
(k) increasing survival time of a CXCR4+ tumor-bearing subject.

In certain embodiments, an antibody of this disclosure binds to native human CXCR4 on a cell surface but does not inhibit binding of SDF-1 to CXCR4 and does not inhibit SDF-1-induced calcium flux in cells expressing CXCR4 and does not inhibit SDF-1-induced migration of cells expressing CXCR4. In other embodiments, an antibody of this disclosure binds to native human CXCR4 on a cell surface and does inhibit binding of SDF-1 to CXCR4 and does inhibit SDF-1-induced calcium flux in cells expressing CXCR4 but does not inhibit SDF-1-induced migration of cells expressing CXCR4. In still other embodiments, an antibody of this disclosure binds to native human CXCR4 on a cell surface and does inhibit binding of SDF-1 to CXCR4 and does inhibit SDF-1-induced calcium flux in cells expressing CXCR4 and does inhibit SDF-1-induced migration of cells expressing CXCR4. In still other embodiments, an antibody of this disclosure binds to native human CXCR4 on a cell surface, does inhibit binding of SDF-1 to CXCR4, does inhibit SDF-1-induced calcium flux in cells expressing CXCR4, does inhibit SDF-1-induced migration of cells expressing CXCR4 and does inhibit capillary tube formation by HuVECs.

Preferably, an antibody of this disclosure binds to human CXCR4 with a $K_D$ of $5 \times 10^{-8}$ M or less, binds to human CXCR4 with a $K_D$ of $2 \times 10^{-8}$ M or less, binds to human CXCR4 with a $K_D$ of $5 \times 10^{-9}$ M or less, binds to human CXCR4 with a $K_D$ of $4 \times 10^{-9}$ M or less, binds to human CXCR4 with a $K_D$ of $3 \times 10^{-9}$ M or less, or binds to human CXCR4 with a $K_D$ of $2 \times 10^{-9}$ M or less.

Preferably, an antibody of the inhibits binding of SDF-1 to human CXCR4 with an $EC_{50}$ for inhibition of 50 nM or less, more preferably 30 nM or less, or 15 nM or less, or 10 nM or less, or 5 nM or less, or 3 nM or less (e.g., an $EC_{50}$ for inhibition of 28.60 nM or less, or 12.51 nM or less, or 2.256 nM or less)

Preferably, an antibody of this disclosure inhibits SDF-1-induced calcium flux in cells expressing human CXCR4 with an $EC_{50}$ for inhibition of 3 nM or less, more preferably 2 nM or less, or 1 nM or less, or 0.9 nM or less, or 0.8 nM or less, or 0.7 nM or less, or 0.6 nM or less, or 0.5 nM or less, or 0.4 nM or less (e.g., 0.9046 nM or less, 0.5684 or less, or 0.3219 nM or less).

Preferably, an antibody of this disclosure inhibits SDF-1-induced migration of cells expressing human CXCR4 with an $EC_{50}$ for inhibition of 50 nM or less, more preferably 30 nM or less, or 20 nM or less, or 15 nM or less (e.g., 18.99 nM or less, or 12.44 or less).

Standard assays to evaluate the binding ability of the antibodies toward native human CXCR4 expressed on a cell surface are known in the art, including for example, flow cytometry analysis using a cell line that naturally expresses native CXCR4 or that has been transfected to express native CXCR4. Suitable assays are described in detail in the Examples. A preferred cell line that expresses native CXCR4 is the CEM T cell line. Suitable assays for evaluating inhibition of binding of SDF-1, inhibition of SDF-1 induced calcium flux, inhibition of SDF-1 induced cell migration, inhibition of capillary tube formation by HuVECs, induction of apoptosis in cells expressing CXCR4 in vitro and/or in vivo, inhibition of growth of $CXCR4^+$ tumor cells in vitro and/or in vivo, and/or inhibition of metastases of $CXCR4^+$ tumor cells are also described in detail in the Examples. Binding affinity of the antibodies also can be determined by standard methods, such as by Scatchard analysis.

Monoclonal Antibodies F7, F9, D1 and E2

Preferred antibodies of this disclosure are the human monoclonal antibodies F7, F9, D1 and E2, isolated and structurally characterized as described in Examples 1 and 2. The $V_H$ amino acid sequences of F7, F9, D1 and E2 are shown in SEQ ID NOs: 25, 26, 27 and 28, respectively. The $V_L$ amino acid sequences of F7, F9, D1 and E2 are shown in SEQ ID NOs: 29, 30, 31 and 32, respectively. Additionally, alternative forms of F7, F9, D1 and E2, in which certain framework residues were substituted with a germline residue, were created and are referred to herein as F7GL, F9GL, D1GL and E2GL. The $V_H$ amino acid sequences of F7GL, F9GL, D1GL and E2GL are shown in SEQ ID NOs: 41, 42, 43 and 44, respectively. The $V_L$ amino acid sequences of F7GL, F9GL, D1GL and E2GL are shown in SEQ ID NOs: 45, 46, 47 and 48, respectively.

Given that each of these antibodies can bind to CXCR4, the $V_H$ and $V_L$ sequences can be "mixed and matched" to create other anti-CXCR4 binding molecules of this disclosure. CXCR4 binding of such "mixed and matched" antibodies can be tested using the binding assays described above and in the Examples (e.g., flow cytometry with CEM cells). Preferably, when $V_H$ and $V_L$ chains are mixed and matched, a $V_H$ sequence from a particular $V_H/V_L$ pairing is replaced with a structurally similar $V_H$ sequence. Likewise, preferably a $V_L$ sequence from a particular $V_H/V_L$ pairing is replaced with a structurally similar $V_L$ sequence.

Accordingly, in one aspect, this disclosure provides an isolated monoclonal antibody, or antigen binding portion thereof comprising:

(a) a heavy chain variable region comprising an amino acid sequence selected from the group consisting of SEQ ID NOs: 25-28 and 41-44; and (b) a light chain variable region comprising an amino acid sequence selected from the group consisting of SEQ ID NOs: 29-32 and 45-48;

wherein the antibody specifically binds CXCR4, preferably human CXCR4.

Preferred heavy and light chain combinations include:

(a) a heavy chain variable region comprising the amino acid sequence of SEQ ID NO: 25 or 41 and a light chain variable region comprising the amino acid sequence of SEQ ID NO: 29 or 45; or (b) a heavy chain variable region comprising the amino acid sequence of SEQ ID NO: 26 or 42 and a light chain variable region comprising the amino acid sequence of SEQ ID NO: 30 or 46; or (c) a heavy chain variable region comprising the amino acid sequence of SEQ ID NO: 27 or 43 and a light chain variable region comprising the amino acid sequence of SEQ ID NO: 31 or 47; or.

(d) a heavy chain variable region comprising the amino acid sequence of SEQ ID NO: 28 or 44 and a light chain variable region comprising the amino acid sequence of SEQ ID NO: 32 or 48.

In another aspect, this disclosure provides antibodies that comprise the heavy chain and light chain CDR1s, CDR2s and CDR3s of F7, F9, D1 or E2, or combinations thereof. The amino acid sequences of the $V_H$ CDR1s of F7, F9, D1 and E2 are shown in SEQ ID NOs: 1-4, respectively. The amino acid sequences of the $V_H$ CDR2s of F7, F9, D1 and E2 are shown in SEQ ID NOs: 5-8, respectively. The amino acid sequences of the $V_H$ CDR3s of F7, F9, D1 and E2 are shown in SEQ ID NOs: 9-12, respectively. The amino acid sequences of the $V_k$ CDR1s of F7, F9, D1 and E2 are shown in SEQ ID NOs: 13-16, respectively. The amino acid sequences of the $V_k$ CDR2s of F7, F9, D1 and E2 are shown in SEQ ID NOs: 17-20, respectively. The amino acid sequences of the $V_k$ CDR3 s of F7, F9, D1 and E2 are shown in SEQ ID NOs: 21-24, respectively. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

Given that each of these antibodies can bind to CXCR4 and that antigen-binding specificity is provided primarily by the CDR1, CDR2, and CDR3 regions, the $V_H$ CDR1, CDR2, and CDR3 sequences and $V_k$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_k$ CDR1, CDR2, and CDR3) to create other anti-CXCR4 binding molecules of this disclosure. CXCR4 binding of such "mixed and matched" antibodies can be tested using the binding assays described above and in the Examples (e.g., ELISAs, Biacore® analysis). Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_k$ CDR sequences are mixed and matched, the CDR1, CDR2 and/or CDR3 sequence from a particular $V_k$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies antibodies F7, F9, D1 and E2.

Accordingly, in another aspect, this disclosure provides an isolated monoclonal antibody, or antigen binding portion thereof comprising:

(a) a heavy chain variable region CDR1 comprising an amino acid sequence selected from the group consisting of SEQ ID NOs: 1-4;

(b) a heavy chain variable region CDR2 comprising an amino acid sequence selected from the group consisting of SEQ ID NOs: 5-8;

(c) a heavy chain variable region CDR3 comprising an amino acid sequence selected from the group consisting of SEQ ID NOs: 9-12;

(d) a light chain variable region CDR1 comprising an amino acid sequence selected from the group consisting of SEQ ID NOs: 13-16;

(e) a light chain variable region CDR2 comprising an amino acid sequence selected from the group consisting of SEQ ID NOs: 17-20; and (f) a light chain variable region CDR3 comprising an amino acid sequence selected from the group consisting of SEQ ID NOs: 21-24;

wherein the antibody specifically binds CXCR4, preferably human CXCR4.

In a preferred embodiment, the antibody comprises:

(a) a heavy chain variable region CDR1 comprising SEQ ID NO: 1;

(b) a heavy chain variable region CDR2 comprising SEQ ID NO: 5;

(c) a heavy chain variable region CDR3 comprising SEQ ID NO: 9;

(d) a light chain variable region CDR1 comprising SEQ ID NO: 13;

(e) a light chain variable region CDR2 comprising SEQ ID NO: 17; and (f) a light chain variable region CDR3 comprising SEQ ID NO: 21.

In another preferred embodiment, the antibody comprises:

(a) a heavy chain variable region CDR1 comprising SEQ ID NO: 2;

(b) a heavy chain variable region CDR2 comprising SEQ ID NO: 6;

(c) a heavy chain variable region CDR3 comprising SEQ ID NO: 10;

(d) a light chain variable region CDR1 comprising SEQ ID NO: 14;

(e) a light chain variable region CDR2 comprising SEQ ID NO: 18; and (f) a light chain variable region CDR3 comprising SEQ ID NO: 22.

In another preferred embodiment, the antibody comprises:

(a) a heavy chain variable region CDR1 comprising SEQ ID NO: 3;

(b) a heavy chain variable region CDR2 comprising SEQ ID NO: 7;

(c) a heavy chain variable region CDR3 comprising SEQ ID NO: 11;

(d) a light chain variable region CDR1 comprising SEQ ID NO: 15;

(e) a light chain variable region CDR2 comprising SEQ ID NO: 19; and (f) a light chain variable region CDR3 comprising SEQ ID NO: 23.

In another preferred embodiment, the antibody comprises:

(a) a heavy chain variable region CDR1 comprising SEQ ID NO: 4;

(b) a heavy chain variable region CDR2 comprising SEQ ID NO: 8;

(c) a heavy chain variable region CDR3 comprising SEQ ID NO: 12;

(d) a light chain variable region CDR1 comprising SEQ ID NO: 16;

(e) a light chain variable region CDR2 comprising SEQ ID NO: 20; and (f) a light chain variable region CDR3 comprising SEQ ID NO: 24.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, for example, Klimka et al., *British J. of Cancer* 83(2):252-260 (2000) (describing the production of a humanized anti-CD30 antibody using only the heavy chain variable domain CDR3 of murine anti-CD30 antibody Ki-4); Beiboer et al., *J. Mol. Biol.* 296:833-849 (2000) (describing recombinant epithelial glycoprotein-2 (EGP-2) antibodies using only the heavy chain CDR3 sequence of the parental murine MOC-31 anti-EGP-2 antibody); Rader et al., *Proc. Natl. Acad. Sci. U.S.A.* 95:8910-8915 (1998) (describing a panel of humanized anti-integrin $\alpha_v\beta_3$ antibodies using a heavy and light chain variable CDR3 domain of a murine anti-integrin $\alpha_v\beta_3$ antibody LM609 wherein each member antibody comprises a distinct sequence outside the CDR3 domain and capable of binding the same epitope as the parent muring antibody with affinities as high or higher than the parent murine antibody); Barbas et al., *J. Am. Chem. Soc.* 116:2161-2162 (1994) (disclosing that the CDR3 domain provides the most significant contribution to antigen binding); Barbas et al., *Proc. Natl. Acad. Sci. U.S.A.* 92:2529-2533 (1995) (describing the grafting of heavy chain CDR3 sequences of three Fabs (SI-1, SI-40, and SI-32) against human placental DNA onto the heavy chain of an anti-tetanus toxoid Fab thereby replacing the existing heavy chain CDR3 and demonstrating that the CDR3 domain alone conferred binding specificity); Ditzel et al., *J. Immunol.* 157:739-749 (1996) (describing grafting studies wherein transfer of only the heavy chain CDR3 of a parent polyspecific Fab LNA3 to a heavy chain of a monospecific IgG tetanus toxoid-binding Fab p313 antibody was sufficient to retain binding specificity of the parent Fab); Berezov et al., *BIA journal* 8: Scientific Review 8 (2001) (describing peptide mimetics based on the CDR3 of an anti-HER2 monoclonal antibody; Igarashi et al., *J. Biochem* (Tokyo) 117:452-7 (1995) (describing a 12 amino acid synthetic polypeptide corresponding to the CDR3 domain of an anti-phosphatidylserine antibody); Bourgeois et al., *J. Virol* 72:807-10 (1998) (showing that a single peptide derived form the heavy chain CDR3 domain of an anti-respiratory syncytial virus (RSV) antibody was capable of neutralizing the virus in vitro); Levi et al., *Proc. Natl. Acad. Sci. U.S.A.* 90:4374-8 (1993) (describing a peptide based on the heavy chain CDR3 domain of a murine anti-HIV antibody); Polymenis and Stoller, *J. Immunol.* 152:5218-5329 (1994) (describing enabling binding of an scFv by grafting the heavy chain CDR3 region of a Z-DNA-binding antibody) and Xu and Davis, Immunity 13:37-45 (2000) (describing that diversity at the heavy chain CDR3 is sufficient to permit otherwise identical IgM molecules to distinguish between a variety of hapten and protein antigens). See also, U.S. Pat. Nos. 6,951,646; 6,914,128; 6,090,382; 6,818,216; 6,156,313; 6,827,925; 5,833,943; 5,762,905 and 5,760,185, describing patented antibodies defined by a single CDR domain. Each of these references is hereby incorporated by reference in its entirety.

Accordingly, the present disclosure provides monoclonal antibodies comprising one or more heavy and/or light chain CDR3 domains from an antibody derived from a human or non-human animal, wherein the monoclonal antibody is capable of specifically binding to CXCR4. Within certain aspects, the present disclosure provides monoclonal antibodies comprising one or more heavy and/or light chain CDR3 domain from a non-human antibody, such as a mouse or rat antibody, wherein the monoclonal antibody is capable of specifically binding to CXCR4. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

Within other aspects, the present disclosure provides monoclonal antibodies comprising one or more heavy and/or light chain CDR3 domain from a human antibody, such as, for example, a human antibody obtained from a non-human animal, wherein the human antibody is capable of specifically binding to CXCR4. Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to CXCR4 and wherein the CDR3 domain from the first human antibody replaces a CDR3 domain in a human antibody that is lacking binding specificity for CXCR4 to generate a second human antibody that is capable of specifically binding to CXCR4. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of this disclosure comprises a heavy chain variable region from a particular germline heavy chain immunoglobulin gene and/or a light chain variable region from a particular germline light chain immunoglobulin gene.

For example, in a preferred embodiment, this disclosure provides an isolated monoclonal antibody, or an antigen-binding portion thereof, comprising a heavy chain variable region that is the product of or derived from a human $V_H$ 3-48 gene, wherein the antibody specifically binds CXCR4. In another preferred embodiment, this disclosure provides an isolated monoclonal antibody, or an antigen-binding portion thereof, comprising a light chain variable region that is the product of or derived from a human $V_K$ L15 gene, wherein the antibody specifically binds CXCR4. In yet another preferred embodiment, this disclosure provides an isolated monoclonal antibody, or antigen-binding portion thereof, wherein the antibody comprises a heavy chain variable region that is the product of or derived from a human $V_H$ 3-48 gene and comprises a light chain variable region that is the product of or derived from a human $V_K$ L15 gene, wherein the antibody specifically binds to CXCR4, preferably human CXCR4. Such antibodies also may possess one or more of the functional characteristics described in detail above, such as binding to native CXCR4 expressed on a cell surface, inhibition of SDF-1 binding to CXCR4, inhibition of SDF-1-induced calcium flux in cells expressing CXCR4, inhibition of SDF-1-induced migration of cells expressing CXCR4, inhibition of capillary tube formation by HuVECs, induction of apoptosis in cells expressing CXCR4 in vitro and/or in vivo, inhibition of growth of CXCR4$^+$ tumor cells in vitro and/or in vivo, and/or inhibition of metastases of CXCR4$^+$ tumor cells.

Examples of antibodies having $V_H$ and $V_K$ of $V_H$ 3-48 and $V_K$ L15, respectively, are the F7, F9, D1 and E2 antibodies.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of this disclosure comprises heavy and light chain variable regions comprising amino acid sequences that are homologous to the amino acid sequences of the preferred antibodies described herein, and wherein the antibodies retain the desired functional properties of the anti-CXCR4 antibodies of this disclosure.

For example, this disclosure provides an isolated monoclonal antibody, or antigen binding portion thereof, comprising a heavy chain variable region and a light chain variable region, wherein:
(a) the heavy chain variable region comprises an amino acid sequence that is at least 80% homologous to an amino acid sequence selected from the group consisting of SEQ ID NOs: 25-28 and 41-44;
(b) the light chain variable region comprises an amino acid sequence that is at least 80% homologous to an amino acid sequence selected from the group consisting of SEQ ID NOs: 29-32 and 45-48;
(c) the antibody binds to native human CXCR4 expressed on a cell surface.

Additionally or alternatively, the antibody may possess one or more of the following functional properties: (i) binds to human CXCR4 with a $K_D$ of $1\times10^{-7}$ M or less; (ii) inhibits SDF-1 binding to CXCR4; (iii) inhibits SDF-1-induced calcium flux in cells expressing CXCR4; (iv) inhibits SDF-1-induced migration of cells expressing CXCR4; (v) inhibits capillary tube formation by HuVECs; (vi) induces apoptosis in cells expressing CXCR4 in vitro and/or in vivo; (vii) inhibits growth of $CXCR4^+$ tumor cells in vitro and/or in vivo; and/or (viii) inhibits metastases of $CXCR4^+$ tumor cells.

In various embodiments, the antibody can be, for example, a human antibody, a humanized antibody or a chimeric antibody.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 25-32 or 41-48, followed by testing of the encoded altered antibody for retained function (i.e., the functions set forth above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present disclosure can further be used as a "query sequence" to perform a search against public databases to, for example, to identify related sequences. Such searches can be performed using the) XBLAST program (version 2.0) of Altschul, et al. (1990) *J. Mol. Biol.* 215:403-10. BLAST protein searches can be performed with the XBLAST program, score=50, wordlength=3 to obtain amino acid sequences homologous to the antibody molecules of this disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) are useful. See www.ncbi.nlm.nih.gov.

Antibodies with Conservative Modifications

In certain embodiments, an antibody of this disclosure comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., F7, F9, D1 or E2), or conservative modifications thereof, and wherein the antibodies retain the desired functional properties of the anti-CXCR4 antibodies of this disclosure. It is understood in the art that certain conservative sequence modification can be made which do not remove antigen binding. See, for example, Brummell et al. (1993) *Biochem* 32:1180-8 (describing mutational analysis in the CDR3 heavy chain domain of antibodies specific for *Salmonella*); de Wildt et al. (1997) *Prot. Eng.* 10:835-41 (describing mutation studies in anti-UA1 antibodies); Komissarov et al. (1997) *J. Biol. Chem.* 272:26864-26870 (showing that mutations in the middle of HCDR3 led to either abolished or diminished affinity); Hall et al. (1992) *J. Immunol.* 149:1605-12 (describing that a single amino acid change in the CDR3 region abolished binding activity); Kelley and O'Connell (1993) *Biochem.* 32:6862-35 (describing the contribution of Tyr residues in antigen binding); Adib-Conquy et al. (1998) *Int. Immunol.* 10:341-6 (describing the effect of hydrophobicity in binding) and Beers et al. (2000) *Clin. Can. Res.* 6:2835-43 (describing HCDR3 amino acid mutants). Accordingly, this disclosure provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region CDR3 sequence comprises an amino acid sequence selected from the group consisting of amino acid sequences of SEQ ID NOs: 9-12, and conservative modifications thereof;

(b) the light chain variable region CDR3 sequence comprises an amino acid sequence selected from the group consisting of amino acid sequence of SEQ ID NOs: 21-44, and conservative modifications thereof; and (c) the antibody binds to native human CXCR4 expressed on a cell surface.

Additionally or alternatively, the antibody may possess one or more of the following functional properties: (i) binds to human CXCR4 with a $K_D$ of $1\times10^{-7}$ M or less; (ii) inhibits SDF-1 binding to CXCR4; (iii) inhibits SDF-1-induced calcium flux in cells expressing CXCR4; (iv) inhibits SDF-1-induced migration of cells expressing CXCR4; (v) inhibits capillary tube formation by HuVECs; (vi) induces apoptosis in cells expressing CXCR4 in vitro and/or in vivo; (vii) inhibits growth of $CXCR4^+$ tumor cells in vitro and/or in vivo; and/or (viii) inhibits metastases of $CXCR4^+$ tumor cells.

In a preferred embodiment, the heavy chain variable region CDR2 sequence comprises an amino acid sequence selected from the group consisting of amino acid sequences of SEQ ID NOs: 5-8, and conservative modifications thereof and the light chain variable region CDR2 sequence comprises an amino acid sequence selected from the group consisting of amino acid sequences of SEQ ID NOs: 17-20, and conservative modifications thereof. In another preferred embodiment, the heavy chain variable region CDR1 sequence comprises an amino acid sequence selected from the group consisting of amino acid sequences of SEQ ID NOs: 1-4, and conservative modifications thereof; and the light chain variable region CDR1 sequence comprises an amino acid sequence selected from the group consisting of amino acid sequences of SEQ ID NOs: 13-16, and conservative modifications thereof.

In various embodiments, the antibody can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of this disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of this disclosure can be replaced with other amino acid residues from the same side chain family and the altered antibody can be tested for retained function (i.e., the functions set forth above) using the functional assays described herein.

Antibodies that Bind to the Same Epitope as Anti-CXCR4 Antibodies

In another embodiment, this disclosure provides antibodies that bind to the same epitope on human CXCR4 as any of the anti-CXCR4 monoclonal antibodies of this disclosure (i.e., antibodies that have the ability to cross-compete for binding to CXCR4 with any of the monoclonal antibodies of this disclosure). In preferred embodiments, the reference antibody for cross-competition studies can be the monoclonal antibody F7 (having $V_H$ and $V_L$ sequences as shown in SEQ ID NOs: 25 and 29, respectively), or the monoclonal antibody F9 (having $V_H$ and $V_L$ sequences as shown in SEQ ID NOs: 26 and 30, respectively) or the monoclonal antibody D1 (having $V_H$ and $V_L$ sequences as shown in SEQ ID NOs: 27 and 31, respectively) or the monoclonal antibody E2 (having $V_H$ and $V_L$ sequences as shown in SEQ ID NOs: 28 and 32, respectively).

Such cross-competing antibodies can be identified based on their ability to cross-compete with F7, F9, D1 or E2 in standard CXCR4 binding assays. For example, flow cytometry with CEM cells may be used to demonstrate cross-competition with the antibodies of the current disclosure, wherein the reference antibody is labeled with FITC and the ability of a test antibody to inhibit the binding of the FITC-labeled reference antibody to CEM cells is evaluated. The ability of a test antibody to inhibit the binding of, for example, F7, F9, D1 or E2, to human CXCR4 demonstrates that the test antibody can compete with F7, F9, D1 or E2 for binding to human CXCR4 and thus binds to the same epitope on human CXCR4 as F7, F9, D1 or E2. In a preferred embodiment, the antibody that binds to the same epitope on CXCR4 as F7, F9, D1 or E2 is a human monoclonal antibody. Such human monoclonal antibodies can be prepared and isolated as described in the Examples.

Engineered and Modified Antibodies

An antibody of this disclosure further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of this disclosure pertains to an isolated monoclonal antibody, or antigen binding portion thereof, comprising a heavy chain variable region comprising CDR1, CDR2, and CDR3 sequences comprising an amino acid sequence selected from the group consisting of SEQ ID NOs: 1-4, SEQ ID NOs: 5-8, and SEQ ID NOs: 9-12, respectively, and a light chain variable region comprising CDR1, CDR2, and CDR3 sequences comprising an amino acid sequence selected from the group consisting of SEQ ID NOs: 13-16, SEQ ID NOs: 17-20, and SEQ ID NOs: 21-24, respectively. Thus, such antibodies contain the $V_H$ and $V_L$ CDR sequences of monoclonal antibodies F7, F9, D1 or E2 yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (CAJ556644) and 3-23 (AJ406678). Yet another source of human heavy and light chain germline sequences is the database of human immunoglobulin genes available from IMGT (http://imgt.cines.fr).

Antibody protein sequences are compared against a compiled protein sequence database using one of the sequence similarity searching methods called the Gapped BLAST (Altschul et al. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin (http://vbase.mrc-cpe.cam.ac.uk/vbase1/list2.php) are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames. Other human germline sequence databases, such as that available from IMGT (http://imgt.cines.fr), can be searched similarly to VBASE as described above.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of this disclosure are those that are structurally similar to the framework sequences used by selected antibodies of this disclosure, e.g., similar to the $V_H$ 3-48 framework sequences (SEQ ID NO: 49) and/or the $V_K$ L15 framework sequence (SEQ ID NO: 50) used by preferred monoclonal antibodies of this disclosure. The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Accordingly, in another embodiment, the instant disclosure provides isolated anti-CXCR4 monoclonal antibodies, or antigen binding portions thereof, comprising a heavy chain variable region comprising: (a) a $V_H$ CDR1 region comprising an amino acid sequence selected from the group consisting of SEQ ID NOs: 1-4, or an amino acid sequence having one, two, three, four or five amino acid substitutions, deletions or additions as compared to SEQ ID NOs: 1-4; (b) a $V_H$ CDR2 region comprising an amino acid sequence selected from the group consisting of SEQ ID NOs: 5-8, or an amino acid sequence having one, two, three, four or five amino acid substitutions, deletions or additions as compared to SEQ ID NOs: 5-8; (c) a $V_H$ CDR3 region comprising an amino acid sequence selected from the group consisting of SEQ ID NOs: 9-12, or an amino acid sequence having one, two, three, four or five amino acid substitutions, deletions or additions as compared to SEQ ID NOs: 9-12; (d) a $V_K$ CDR1 region comprising an amino acid sequence selected from the group consisting of SEQ ID NOs: 13-16, or an amino acid sequence having one, two, three, four or five amino acid substitutions, deletions or additions as compared to SEQ ID NOs: 13-16; (e) a $V_K$ CDR2 region comprising an amino acid sequence selected from the group consisting of SEQ ID NOs: 17-20, or an amino acid sequence having one, two, three, four or five amino acid substitutions, deletions or additions as compared to SEQ ID NOs: 17-20; and (f) a $V_K$ CDR3 region comprising an amino acid sequence selected from the group consisting of SEQ ID NOs: 21-24, or an amino acid sequence having one, two, three, four or five amino acid substitutions, deletions or additions as compared to SEQ ID NOs: 21-24.

Engineered antibodies of this disclosure include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, for the F7 $V_H$ region, the following framework region amino acid positions (using the Kabat numbering system) differ from germline: 1, 6 and 25. One, two or all three of these positions can be backmutated to germline sequences by making one, two or all three of the following substitutions: Q1E, Q6E and A25S. A preferred modified form of the F7 V$_H$ region is F7GL V$_H$ (the amino acid sequence of which is shown in FIG. 5A and in SEQ ID NO: 41), which has the following framework substitutions: Q1E and Q6E.

Furthermore, for the F7 V$_k$ region, the following framework region amino acid positions (using the Kabat numbering system) differ from germline: 1, 3 and 84. One, two or all three of these positions can be backmutated to germline sequences by making one, two or all three of the following substitutions: A1D, R3Q and V84A. A preferred modified form of the F7 V$_k$ region is F7GL V$_k$ (the amino acid sequence of which is shown in FIG. 5B and in SEQ ID NO: 45), which has the following framework substitutions: MD and R3Q.

Furthermore, for the F9 V$_H$ region, the following framework region amino acid positions (using the Kabat numbering system) differ from germline: 1, 6 and 25. One, two or all three of these positions can be backmutated to germline sequences by making one, two or all three of the following substitutions: Q1E, Q6E and A25S. A preferred modified form of the F9 V$_H$ region is F9GL V$_H$ (the amino acid sequence of which is shown in FIG. 6A and in SEQ ID NO: 42), which has the following framework substitutions: Q1E and Q6E.

Furthermore, for the F9 V$_k$ region, the following framework region amino acid positions (using the Kabat numbering system) differ from germline: 1, 3, 4 and 60. One, two, three or all four of these positions can be backmutated to germline sequences by making one, two, three or all four of the following substitutions: E1D, V3Q, L4M and P60S. A preferred modified form of the F9 V$_k$ region is F9GL V$_k$ (the amino acid sequence of which is shown in FIG. 6B and in SEQ ID NO: 46), which has the following framework substitutions: E1D, V3Q and L4M.

Furthermore, for the D1 V$_H$ region, the following framework region amino acid positions (using the Kabat numbering system) differ from germline: 6, 25 and 76. One, two or all three of these positions can be backmutated to germline sequences by making one, two or all three of the following substitutions: Q6E, A25S and R76K. A preferred modified form of the D1 V$_H$ region is D1GL V$_H$ (the amino acid sequence of which is shown in FIG. 7A and in SEQ ID NO: 43), which has the following framework substitution: Q6E.

Furthermore, for the D1 V$_k$ region, the following framework region amino acid positions (using the Kabat numbering system) differ from germline: 1, 3, 4, 45 and 46. One, two, three, four or all five of these positions can be backmutated to germline sequences by making one, two, three, four or all five of the following substitutions: V1D, W3Q, V4M, E45K and L46S. A preferred modified form of the D1 V$_k$ region is D1GL V$_k$ (the amino acid sequence of which is shown in FIG. 7B and in SEQ ID NO: 47), which has the following framework substitutions: V1D, W3Q and V4M.

Furthermore, for the E2 V$_H$ region, the following framework region amino acid positions (using the Kabat numbering system) differ from germline: 6 and 25. One or both of these positions can be backmutated to germline sequences by making one or both of the following substitutions: Q6E and A25S. A preferred modified form of the E2 V$_H$ region is E2GL V$_H$ (the amino acid sequence of which is shown in FIG. 8A and in SEQ ID NO: 44), which has the following framework substitution: Q6E.

Furthermore, for the E2 V$_k$ region, the following framework region amino acid positions (using the Kabat numbering system) differ from germline: 1, 3 and 4. One, two or all three of these positions can be backmutated to germline sequences by making one, two or all three of the following substitutions: E1D, V3Q and L4M. A preferred modified form of the E2 V$_k$ region is E2GL V$_k$ (the amino acid sequence of which is shown in FIG. 8B and in SEQ ID NO: 48), which has the following framework substitutions: E1D, V3Q and L4M.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of this disclosure may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of this disclosure may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of this disclosure to thereby produce an antibody with altered glycosylation. For example, the cell lines Ms704, Ms705, and Ms709 lack the fucosyltransferase gene, FUT8 (alpha (1,6) fucosyltransferase), such that antibodies expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the alpha 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). Antibodies with a modified glycosylation profile can also be produced in chicken eggs, as described in US Patent Application No. PCT/US06/05853. Alternatively, antibodies with a modified glycosylation profile can be produced in plant cells, such as *Lemna*. Methods for production of antibodies in a plant system are disclosed in the U.S. Patent application corresponding to Alston & Bird LLP, filed on Aug. 11, 2006. PCT Publication WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17:176-180). Alternatively, the fucose residues of the antibody may be cleaved off using a fucosidase enzyme. For example, the fucosidase alpha-L-fucosidase removes fucosyl residues from antibodies (Tarentino, A. L. et al. (1975) *Biochem.* 14:5516-23).

Another modification of the antibodies herein that is contemplated by this disclosure is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of this disclosure. See for example, EP 0 154 316 by Nishimura et al. and EP 0 401 384 by Ishikawa et al.

Antibody Fragments and Antibody Mimetics

The instant invention is not limited to traditional antibodies and may be practiced through the use of antibody fragments and antibody mimetics. As detailed below, a wide variety of antibody fragment and antibody mimetic technologies have now been developed and are widely known in the art. While a number of these technologies, such as domain antibodies, Nanobodies, and UniBodies make use of fragments of, or other modifications to, traditional antibody structures, there are also alternative technologies, such as Affibodies, DARPins, Anticalins, Avimers, and Versabodies that employ binding structures that, while they mimic traditional antibody binding, are generated from and function via distinct mechanisms.

Domain Antibodies (dAbs) are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582,915; 6,593,081; 6,172,197; 6,696,245; US Serial No. 2004/0110941; European patent application No. 1433846 and European Patents 0368684 & 0616640; WO05/035572, WO04/101790, WO04/081026, WO04/058821, WO04/003019 and WO03/002609, each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. Nanobodies have a high homology with the VH domains of human antibodies and can be further humanized without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity, high affinity for their target and low inherent toxicity. However, like small molecule drugs they can inhibit enzymes and readily access receptor clefts. Furthermore, Nanobodies are extremely stable, can be administered by means other than injection (see e.g. WO 04/041867, which is herein incorporated by reference in its entirety) and are easy to manufacture. Other advantages of Nanobodies include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts e.g. *E. coli* (see e.g. U.S. Pat. No. 6,765,087, which is herein incorporated by reference in its entirety), molds (for example *Aspergillus* or *Trichoderma*) and yeast (for example *Saccharomyces, Kluyveromyces, Hansenula* or *Pichia*) (see e.g. U.S. Pat. No. 6,838,254, which is herein incorporated by reference in its entirety). The production process is scalable and multi-kilogram quantities of Nanobodies have been produced. Because Nanobodies exhibit a superior stability compared with conventional antibodies, they can be formulated as a long shelf-life, ready-to-use solution.

The Nanoclone method (see e.g. WO 06/079372, which is herein incorporated by reference in its entirety) is a proprietary method for generating Nanobodies against a desired target, based on automated high-throughout selection of B-cells and could be used in the context of the instant invention.

UniBodies are another antibody fragment technology, however this one is based upon the removal of the hinge region of IgG4 antibodies. The deletion of the hinge region results in a molecule that is essentially half the size of traditional IgG4 antibodies and has a univalent binding region rather than the bivalent binding region of IgG4 antibodies. It is also well known that IgG4 antibodies are inert and thus do not interact with the immune system, which may be advantageous for the treatment of diseases where an immune response is not desired, and this advantage is passed onto UniBodies. For example, UniBodies may function to inhibit or silence, but not kill, the cells to which they are bound. Additionally, UniBody binding to cancer cells do not stimulate them to proliferate. Furthermore, because UniBodies are about half the size of traditional IgG4 antibodies, they may show better distribution over larger solid tumors with potentially advantageous efficacy. UniBodies are cleared from the body at a similar rate to whole IgG4 antibodies and are able to bind with a similar affinity for their antigens as whole antibodies. Further details of UniBodies may be obtained by reference to patent WO2007/059782, which is herein incorporated by reference in its entirety.

Affibody molecules represent a new class of affinity proteins based on a 58-amino acid residue protein domain, derived from one of the IgG-binding domains of staphylococcal protein A. This three helix bundle domain has been used as a scaffold for the construction of combinatorial phagemid libraries, from which Affibody variants that target the desired molecules can be selected using phage display technology (Nord K, Gunneriusson E, Ringdahl J, Stahl S, Uhlen M, Nygren P A, Binding proteins selected from combinatorial libraries of an α-helical bacterial receptor domain, *Nat Biotechnol* 1997; 15:772-7. Ronmark J, Gronlund H, Uhlen M, Nygren P A, Human immunoglobulin A (IgA)-specific ligands from combinatorial engineering of protein A, Eur J Biochem 2002; 269:2647-55.). The simple, robust structure of Affibody molecules in combination with their low molecular weight (6 kDa), make them suitable for a wide variety of applications, for instance, as detection reagents (Ronmark J, Hansson M, Nguyen T, et al, Construction and characterization of affibody-Fc chimeras produced in *Escherichia coli*, J Immunol Methods 2002; 261:199-211) and to inhibit receptor interactions (Sandstorm K, Xu Z, Forsberg G, Nygren P A, Inhibition of the CD28-CD80 co-stimulation signal by a CD28-binding Affibody ligand developed by combinatorial protein engineering, Protein Eng 2003; 16:691-7). Further details of Affibodies and methods of production thereof may be obtained by reference to U.S. Pat. No. 5,831,012 which is herein incorporated by reference in its entirety.

Labelled Affibodies may also be useful in imaging applications for determining abundance of Isoforms.

DARPins (Designed Ankyrin Repeat Proteins) are one example of an antibody mimetic DRP (Designed Repeat Protein) technology that has been developed to exploit the binding abilities of non-antibody polypeptides. Repeat proteins such as ankyrin or leucine-rich repeat proteins, are ubiquitous binding molecules, which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated.

This strategy includes the consensus design of self-compatible repeats displaying variable surface residues and their random assembly into repeat domains.

DARPins can be produced in bacterial expression systems at very high yields and they belong to the most stable proteins known. Highly specific, high-affinity DARPins to a broad range of target proteins, including human receptors, cytokines, kinases, human proteases, viruses and membrane proteins, have been selected. DARPins having affinities in the single-digit nanomolar to picomolar range can be obtained.

DARPins have been used in a wide range of applications, including ELISA, sandwich ELISA, flow cytometric analysis (FACS), immunohistochemistry (IHC), chip applications, affinity purification or Western blotting. DARPins also proved to be highly active in the intracellular compartment for example as intracellular marker proteins fused to green fluorescent protein (GFP). DARPins were further used to inhibit viral entry with IC50 in the pM range. DARPins are not only ideal to block protein-protein interactions, but also to inhibit enzymes. Proteases, kinases and transporters have been successfully inhibited, most often an allosteric inhibition mode. Very fast and specific enrichments on the tumor and very favorable tumor to blood ratios make DARPins well suited for in vivo diagnostics or therapeutic approaches.

Additional information regarding DARPins and other DRP technologies can be found in US Patent Application Publication No. 2004/0132028 and International Patent Application Publication No. WO 02/20565, both of which are hereby incorporated by reference in their entirety.

Anticalins are an additional antibody mimetic technology, however in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids which is marginally larger than a single immunoglobulin domain.

Lipocalins are cloned and their loops are subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have successfully demonstrated that Anticalins can be developed that are specific for virtually any human target protein can be isolated and binding affinities in the nanomolar or higher range can be obtained.

Anticalins can also be formatted as dual targeting proteins, so-called Duocalins. A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins, offering flexible formulation and delivery potential for Duocalins.

Additional information regarding Anticalins can be found in U.S. Pat. No. 7,250,297 and International Patent Application Publication No. WO 99/16873, both of which are hereby incorporated by reference in their entirety.

Another antibody mimetic technology useful in the context of the instant invention are Avimers. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared with conventional single-epitope binding proteins. Other potential advantages include simple and efficient production of multitarget-specific molecules in *Escherichia coli*, improved thermostability and resistance to proteases. Avimers with sub-nanomolar affinities have been obtained against a variety of targets.

Additional information regarding Avimers can be found in US Patent Application Publication Nos. 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that could be used in the context of the instant invention. Versabodies are small proteins of 3-5 kDa with >15% cysteines, which form a high disulfide density scaffold, replacing the hydrophobic core that typical proteins have. The replacement of a large number of hydrophobic amino acids, comprising the hydrophobic core, with a small number of disulfides results in a protein that is smaller, more hydrophilic (less aggregation and non-specific binding), more resistant to proteases and heat, and has a lower density of T-cell epitopes, because the residues that contribute most to WIC presentation are hydrophobic. All four of these properties are well-known to affect immunogenicity, and together they are expected to cause a large decrease in immunogenicity.

The inspiration for Versabodies comes from the natural injectable biopharmaceuticals produced by leeches, snakes, spiders, scorpions, snails, and anemones, which are known to exhibit unexpectedly low immunogenicity. Starting with selected natural protein families, by design and by screening the size, hydrophobicity, proteolytic antigen processing, and epitope density are minimized to levels far below the average for natural injectable proteins.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in *E. coli* at high yields, and because of their hydrophilicity and small size, Versabodies are highly soluble and can be formulated to high concentrations. Versabodies are exceptionally heat stable (they can be boiled) and offer extended shelf-life.

Additional information regarding Versabodies can be found in US Patent Application Publication No. 2007/0191272 which is hereby incorporated by reference in its entirety.

The detailed description of antibody fragment and antibody mimetic technologies provided above is not intended to be a comprehensive list of all technologies that could be used in the context of the instant specification. For example, and also not by way of limitation, a variety of additional technologies including alternative polypeptide-based technologies, such as fusions of complimentary determining regions as outlined in Qui et al., *Nature Biotechnology*, 25(8) 921-929 (2007), which is hereby incorporated by reference in its entirety, as well as nucleic acid-based technologies, such as the RNA aptamer technologies described in U.S. Pat. Nos. 5,789,157, 5,864,026, 5,712,375, 5,763,566, 6,013,443, 6,376,474, 6,613,526, 6,114,120, 6,261,774, and 6,387,620, all of which are hereby incorporated by reference, could be used in the context of the instant invention.

Antibody Physical Properties

The antibodies of the present disclosure may be further characterized by the various physical properties of the anti-CXCR4 antibodies. Various assays may be used to detect and/or differentiate different classes of antibodies based on these physical properties.

In some embodiments, antibodies of the present disclosure may contain one or more glycosylation sites in either the light or heavy chain variable region. The presence of one or more glycosylation sites in the variable region may result in increased immunogenicity of the antibody or an alteration of the pK of the antibody due to altered antigen binding (Marshall et al (1972) *Annu Rev Biochem* 41:673-702; Gala F A and Morrison SL (2004) *J Immunol* 172:5489-94; Wallick et al (1988) *J Exp Med* 168:1099-109; Spiro R G (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N-X-S/T sequence. Variable region glycosylation may be tested using a Glycoblot assay, which cleaves the antibody to produce a Fab, and then tests for glycosylation using an assay that measures periodate oxidation and Schiff base formation. Alternatively, variable region glycosylation may be tested using Dionex light chromatography (Dionex-LC), which cleaves saccharides from a Fab into monosaccharides and analyzes the individual saccharide content. In some instances, it is preferred to have an anti-CXCR4 antibody that does not contain variable region glycosylation. This can be achieved either by selecting antibodies that do not contain the glycosylation motif in the variable region or by mutating residues within the glycosylation motif using standard techniques well known in the art.

In a preferred embodiment, the antibodies of the present disclosure do not contain asparagine isomerism sites. A deamidation or isoaspartic acid effect may occur on N-G or D-G sequences, respectively. The deamidation or isoaspartic acid effect results in the creation of isoaspartic acid which decreases the stability of an antibody by creating a kinked structure off a side chain carboxy terminus rather than the main chain. The creation of isoaspartic acid can be measured using an iso-quant assay, which uses a reverse-phase HPLC to test for isoaspartic acid.

Each antibody will have a unique isoelectric point (pI), but generally antibodies will fall in the pH range of between 6 and 9.5. The pI for an IgG1 antibody typically falls within the pH range of 7-9.5 and the pI for an IgG4 antibody typically falls within the pH range of 6-8. Antibodies may have a pI that is outside this range. Although the effects are generally unknown, there is speculation that antibodies with a pI outside the normal range may have some unfolding and instability under in vivo conditions. The isoelectric point may be tested using a capillary isoelectric focusing assay, which creates a pH gradient and may utilize laser focusing for increased accuracy (Janini et al (2002) *Electrophoresis* 23:1605-11; Ma et al. (2001) *Chromatographia* 53:S75-89; Hunt et al (1998) *J Chromatogr A* 800:355-67). In some instances, it is preferred to have an anti-CXCR4 antibody that contains a pI value that falls in the normal range. This can be achieved either by selecting antibodies with a pI in the normal range, or by mutating charged surface residues using standard techniques well known in the art.

Each antibody will have a melting temperature that is indicative of thermal stability (Krishnamurthy R and Manning M C (2002) *Curr Pharm Biotechnol* 3:361-71). A higher thermal stability indicates greater overall antibody stability in vivo. The melting point of an antibody may be measure using techniques such as differential scanning calorimetry (Chen et al (2003) *Pharm Res* 20:1952-60; Ghirlando et al (1999) *Immunol Lett* 68:47-52). $T_{M1}$ indicates the temperature of the initial unfolding of the antibody. $T_{M2}$ indicates the temperature of complete unfolding of the antibody. Generally, it is preferred that the $T_{M1}$ of an antibody of the present disclosure is greater than 60° C., preferably greater than 65° C., even more preferably greater than 70° C. Alternatively, the thermal stability of an antibody may be measure using circular dichroism (Murray et al. (2002) *J. Chromatogr Sci* 40:343-9).

In a preferred embodiment, antibodies are selected that do not rapidly degrade. Fragmentation of an anti-CXCR4 antibody may be measured using capillary electrophoresis (CE) and MALDI-MS, as is well understood in the art (Alexander A J and Hughes D E (1995) *Anal Chem* 67:3626-32).

In another preferred embodiment, antibodies are selected that have minimal aggregation effects. Aggregation may lead to triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation may be measured by several techniques well known in the art, including size-exclusion column (SEC) high performance liquid chromatography (HPLC), and light scattering to identify monomers, dimers, trimers or multimers.

Methods of Engineering Antibodies

As discussed above, the anti-CXCR4 antibodies having $V_H$ and $V_K$ sequences disclosed herein can be used to create new anti-CXCR4 antibodies by modifying the $V_H$ and/or $V_K$ sequences, or the constant region(s) attached thereto. Thus, in another aspect of this disclosure, the structural features of an anti-CXCR4 antibody of this disclosure, e.g. F7, F9, D1 or E2, are used to create structurally related anti-CXCR4 antibodies that retain at least one functional property of the antibodies of this disclosure, such as binding to human CXCR4. For example, one or more CDR regions of F7, F9, D1 or E2, or mutations thereof, can be combined recombinantly with known framework regions and/or other CDRs to create additional, recombinantly-engineered, anti-CXCR4 antibodies of this disclosure, as discussed above. Other types of modifications include those described in the previous section. The starting material for the engineering method is one or more of the $V_H$ and/or $V_K$ sequences provided herein, or one or more CDR regions thereof. To create the engineered antibody, it is not necessary to actually prepare (i.e., express as a protein) an antibody having one or more of the $V_H$ and/or $V_K$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, this disclosure provides a method for preparing an anti-CXCR4 antibody comprising:
  (a) providing: (i) a heavy chain variable region antibody sequence comprising a CDR1 sequence selected from the group consisting of SEQ ID NOs: 1-4, a CDR2 sequence selected from the group consisting of SEQ ID NOs: 5-8, and/or a CDR3 sequence selected from the group consisting of SEQ ID NOs: 9-12; and/or (ii) a light chain variable region antibody sequence comprising a CDR1 sequence selected from the group consisting of SEQ ID NOs: 13-16, a CDR2 sequence selected from the group consisting of SEQ ID NOs: 17-20, and/or a CDR3 sequence selected from the group consisting of SEQ ID NOs: 21-24;
  (b) altering at least one amino acid residue within the heavy chain variable region antibody sequence and/or the light chain variable region antibody sequence to create at least one altered antibody sequence; and
  (c) expressing the altered antibody sequence as a protein.

Standard molecular biology techniques can be used to prepare and express the altered antibody sequence.

Preferably, the antibody encoded by the altered antibody sequence(s) is one that retains one, some or all of the functional properties of the anti-CXCR4 antibodies described herein, which functional properties include, but are not limited to:
  (i) binding to native human CXCR4 expressed on a cell surface;
  (ii) inhibiting binding of SDF-1 to CXCR4;
  (iii) inhibiting SDF-1-induced calcium flux in cells expressing CXCR4;
  (iv) inhibiting SDF-1-induced migration of cells expressing CXCR4
  (v) inhibiting capillary tube formation by HuVECs;
  (vi) binding to human CXCR4 with a $K_D$ of $1 \times 10^{-7}$ M or less;
  (vii) inducing apoptosis in cells expressing CXCR4;
  (viii) inhibiting tumor cell proliferation in vitro;
  (ix) inhibiting tumor cell proliferation and/or inducing tumor cell apoptosis in vivo;
  (x) inhibiting metastases of CXCR4$^+$ tumor cells; and/or
  (xi) increasing survival time of a CXCR4$^+$ tumor-bearing subject.

The functional properties of the altered antibodies can be assessed using standard assays available in the art and/or described herein, such as those set forth in the Examples (e.g., flow cytometry, binding assays, functional assays).

In certain embodiments of the methods of engineering antibodies of this disclosure, mutations can be introduced randomly or selectively along all or part of an anti-CXCR4 antibody coding sequence and the resulting modified anti-CXCR4 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of this Disclosure

Another aspect of this disclosure pertains to nucleic acid molecules that encode the antibodies of this disclosure. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of this disclosure can be, for example, DNA or RNA and may or may not contain intronic sequences. In a preferred embodiment, the nucleic acid is a cDNA molecule.

Nucleic acids of this disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of this disclosure are those encoding the $V_H$ and $V_L$ sequences of the F7, F9, D1 and E2 monoclonal antibodies. DNA sequences encoding the $V_H$ sequences of F7, F9, D1 and E2 are shown in SEQ ID NOs: 33-36, respectively. DNA sequences encoding the $V_L$ sequences of F7, F9, D1 and E2 are shown in SEQ ID NOs: 37-40, respectively.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., el al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of this Disclosure

Monoclonal antibodies (mAbs) of the present disclosure can be produced by a variety of techniques, including conventional monoclonal antibody methodology e.g., the standard somatic cell hybridization technique of Kohler and Milstein (1975) *Nature* 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In a preferred embodiment, the antibodies of this disclosure are human monoclonal antibodies. Such human monoclonal antibodies directed against CXCR4 can be generated using transgenic or transchromosomic mice carrying parts of the human immune system rather than the mouse system. These transgenic and transchromosomic mice include mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) *Intern. Rev. Immunol.* 13: 65-93, and Harding, F. and Lonberg, N. (1995) *Ann. N.Y. Acad. Sci.* 764:536-546). Preparation and use of the HuMAb Mouse®, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of this disclosure can be raised using a mouse that carries human immunoglobulin sequences on transgenes and transchomosomes, such as a mouse that carries a human heavy chain transgene and a human light chain transchromosome. This mouse is referred to herein as a "KM Mouse®," and is described in detail in PCT Publication WO 02/43478 to Ishida et al.

Still further, alternative transgenic animal systems expressing human immunoglobulin genes are available in the art and can be used to raise anti-CXCR4 antibodies of this disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise anti-CXCR4 antibodies of this disclosure. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been described in the art (e.g., Kuroiwa et al. (2002) *Nature Biotechnology* 20:889-894 and PCT application No. WO 2002/092812) and can be used to raise anti-CXCR4 antibodies of this disclosure.

Human monoclonal antibodies of this disclosure can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In a particularly preferred embodiment, human anti-CXCR4 antibodies are prepared using a combination of human Ig mouse and phage display techniques, as described in U.S. Pat. No. 6,794,132 by Buechler et al. More specifically, the method first involves raising an anti-CXCR4 antibody response in a human Ig mouse (such as a HuMab mouse or KM mouse as described above) by immunizing the mouse with a CXCR4 antigen, followed by isolating nucleic acids encoding human antibody chains from lymphatic cells of the mouse and introducing these nucleic acids into a display vector (e.g., phage) to provide a library of display packages. Thus, each library member comprises a nucleic acid encoding a human antibody chain and each antibody chain is displayed from the display package. The library then is screened with a CXCR4 antigen to isolate library members that specifically bind CXCR4. Nucleic acid inserts of the selected library members then are isolated and sequenced by standard methods to determine the light and heavy chain variable sequences of the selected CXCR4 binders. The variable regions can be converted to full-length antibody chains by standard recombinant DNA techniques, such as cloning of the variable regions into an expression vector that carries the human heavy and light chain constant regions such that the VH region is operatively linked to the CH region and the VL region is operatively linked to the CL region. For a further description of the preparation of human anti-CXCR4 antibodies using this combined transgenic mouse/phage display system, see Example 1.

Immunization of Human Ig Mice

When human Ig mice are used to raise human antibodies of this disclosure, such mice can be immunized with a purified or enriched preparation of CXCR4 antigen and/or recombinant CXCR4, or cells expressing CXCR4, or a CXCR4 fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (5-50 μg) of CXCR4 antigen can be used to immunize the human Ig mice intraperitoneally. Most preferably, the immunogen used to raise the antibodies of this disclosure comprises human CXCR4 in its native conformation within a membrane, non-limiting examples of which include cells transfected to express CXCR4 on their cell surface, cells that natively express CXCR4 (e.g., CEM cells), and artificial membranes (e.g., liposomes) into which CXCR4 has been incorporated, such as magnetic proteoliposomes (MPLs) that incorporate CXCR4 (described further in Example 1).

Detailed procedures to generate fully human monoclonal antibodies to CXCR4 are described in Example 1 below. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-CXCR4 human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse® strain can be used, as described in Example 1.

Generation of Hybridomas Producing Human Monoclonal Antibodies of this Disclosure To generate hybridomas producing human monoclonal antibodies of this disclosure, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Alternatively, the single cell suspension of splenic lymphocytes from immunized mice can be fused using an electric field based electrofusion method, using a CytoPulse large chamber cell fusion electroporator (CytoPulse Sciences, Inc., Glen Burnie Md.). Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies of this Disclosure

Antibodies of this disclosure also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_K$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of this disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of this disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of this disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13).

Preferred mammalian host cells for expressing the recombinant antibodies of this disclosure include Chinese Hamster Ovary (CHO cells) (including dhfr⁻ CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of this disclosure can be tested for binding to CXCR4 by, for example, standard flow cytometry methods. Since the antibodies of this disclosure preferably recognize CXCR4 in its native conformation within a membrane, testing for binding to CXCR4 preferably is done with an assay (e.g., flow cytometry) that utilizes a reagent expressing native conformation CXCR4. Nonlimiting examples of reagents expressing native conformation CXCR4 that can be used in the binding assays include cells that naturally express CXCR4 (e.g., CEM cells), cells that have been transfected to express CXCR4 (e.g., R1610 cells transfected with a CXCR4 expression vector) and liposomes into which CXCR4 has been incorporated (e.g., magnetic proteoliposomes incorporating CXCR4), each of which is described in further detail in the Examples. Briefly, for the flow cytometry assay, cells expressing CXCR4 are incubated with the test antibody, washed, incubated with a labeled secondary reagent capable of binding to the test antibody, washed again, and subjected to analysis to detect the binding of the secondary reagent to the cells (e.g., using a FACS machine). Preferably, mice that develop the highest titers as evaluated by flow cytometry will be used for fusions or for further selection of antibodies (e.g., by phage display screening of antibody libraries made from B cells of the mouse).

A flow cytometry assay as described above can also be used to screen for hybridomas that show positive reactivity with CXCR4 immunogen. Hybridomas expressing antibodies that bind with high avidity to CXCR4 are subcloned and further characterized. One clone from each hybridoma, which retains the reactivity of the parent cells (by flow cytometry), can be chosen for making a 5-10 vial cell bank stored at −140° C., and for antibody purification.

To purify anti-CXCR4 antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-CXCR4 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using a whole cell ELISA assay in which ELISA plates are coated with cells expressing CXCR4, and the ability of the unlabeled antibody to compete with the biotinylated antibody for binding to the CXCR4-expressing cells is examined. Biotinylated mAb binding can be detected with a strep-avidin-alkaline phosphatase probe.

To determine the isotype of purified antibodies, isotype ELISAs can be performed using reagents specific for antibodies of a particular isotype. For example, to determine the isotype of a human monoclonal antibody, wells of microtiter plates can be coated with 1 μg/ml of anti-human immunoglobulin overnight at 4° C. After blocking with 1% BSA, the plates are reacted with 1 μg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-CXCR4 human IgGs can be further tested for reactivity with CXCR4 antigen by Western blotting. Briefly, CXCR4 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

The binding specificity of an antibody of this disclosure may also be determined by monitoring binding of the antibody to cells expressing CXCR4, for example by flow cytometry. Typically, a cell line, such as a CHO cell line, may be transfected with an expression vector encoding a transmembrane form of CXCR4. The transfected protein may comprise a tag, such as a myc-tag, preferably at the N-terminus, for detection using an antibody to the tag. Binding of an antibody of this disclosure to CXCR4 may be determined by incubating the transfected cells with the antibody, and detecting bound antibody. Binding of an antibody to the tag on the transfected protein may be used as a positive control.

Immunoconjugates

In another aspect, the present disclosure features an anti-CXCR4 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other preferred examples of therapeutic cytotoxins that can be conjugated to an antibody of this disclosure include duocarmycins, calicheamicins, maytansines and auristatins, and derivatives thereof. An example of a calicheamicin antibody conjugate is commercially available (Mylotarg®; American Home Products).

Cytotoxins can be conjugated to antibodies of this disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al. (2003) *Adv. Drug Deliv. Rev.* 55:199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3:1089-1091; Senter, P. D. and Springer, C. J. (2001) *Adv. Drug Deliv. Rev.* 53:247-264.

Antibodies of the present disclosure also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Method for preparing radioimmunconjugates are established in the art. Examples of radioimmunoconjugates are commercially available, including Zevalin® (IDEC Pharmaceuticals) and Bexxar® (Corixa Pharmaceuticals), and similar methods can be used to prepare radioimmunoconjugates using the antibodies of this disclosure.

The antibody conjugates of this disclosure can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., *Immunol. Rev.,* 62:119-58 (1982).

Bispecific Molecules

In another aspect, the present disclosure features bispecific molecules comprising an anti-CXCR4 antibody, or a fragment thereof, of this disclosure. An antibody of this disclosure, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of this disclosure may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule of this disclosure, an antibody of this disclosure can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present disclosure includes bispecific molecules comprising at least one first binding specificity for CXCR4 and a second binding specificity for a second target epitope. In a particular embodiment of this disclosure, the second target epitope is an Fc receptor, e.g., human FcγRI (CD64) or a human Fcα receptor (CD89). Therefore, this disclosure includes bispecific molecules capable of binding both to FcγR or FcαR expressing effector cells (e.g., monocytes, macrophages or polymorphonuclear cells (PMNs)), and to target cells expressing CXCR4. These bispecific molecules target CXCR4 expressing cells to effector cell and trigger Fc receptor-mediated effector cell activities, such as phagocytosis of CXCR4 expressing cells, antibody dependent cell-mediated cytotoxicity (ADCC), cytokine release, or generation of superoxide anion.

In an embodiment of this disclosure in which the bispecific molecule is multispecific, the molecule can further include a third binding specificity, in addition to an anti-Fc binding specificity and an anti-CXCR4 binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1 or other immune cell that results in an increased immune response against the target cell).

In one embodiment, the bispecific molecules of this disclosure comprise as a binding specificity at least one antibody, or an antibody fragment thereof, including, e.g., an Fab, Fab', F(ab')$_2$, Fv, Fd, dAb or a single chain Fv. The antibody may also be a light chain or heavy chain dimer, or any minimal fragment thereof such as a Fv or a single chain construct as described in U.S. Pat. No. 4,946,778 to Ladner et al., the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ $M^{-1}$).

The production and characterization of certain preferred anti-Fcγ □□ monoclonal antibodies are described in PCT Publication WO 88/00052 and in U.S. Pat. No. 4,954,617 to Fanger et al., the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this disclosure are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and PCT Publication WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity $5\times10^7$ $M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148:1764).

FcαRI and FcγRI are preferred trigger receptors for use in the bispecific molecules of this disclosure because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific molecules of this disclosure are murine, chimeric and humanized monoclonal antibodies.

The bispecific molecules of the present disclosure can be prepared by conjugating the constituent binding specificities, e.g., the anti-FcR and anti-CXCR4 binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83, and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb× mAb, mAb× Fab, Fab×F (ab')$_2$ or ligand× Fab fusion protein. A bispecific molecule of this disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, enzyme-linked immunosorbent assay (ELISA), radioimmunoassay (MA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (MA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a □γ□ counter or a scintillation counter or by autoradiography.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. Such compositions may include one or a combination of (e.g., two or more different) antibodies, or immunoconjugates or bispecific molecules of this disclosure. For example, a pharmaceutical composition of this disclosure can comprise a combination of antibodies (or immunoconjugates or bispecifics) that bind to different epitopes on the target antigen or that have complementary activities.

Pharmaceutical compositions of this disclosure also can be administered in combination therapy, i.e., combined with other agents. For example, the combination therapy can include an anti-CXCR4 antibody of the present disclosure combined with at least one other anti-inflammatory or immunosuppressant agent. Examples of therapeutic agents that can be used in combination therapy are described in greater detail below in the section on uses of the antibodies of this disclosure.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds of this disclosure may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of this disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-CXCR4 antibody of this disclosure include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-CXCR4 antibody of this disclosure preferably results in a decrease in severity of disease symptoms, an increase in frequency and duration of disease symptom-free periods, or a prevention of impairment or disability due to the disease affliction. For example, for the treatment of CXCR4$^+$ tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of this disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition of this disclosure can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of this disclosure can be formulated to ensure proper distribution in vivo. For example, the blood-brain barrier (BBB) excludes many highly hydrophilic compounds. To ensure that the therapeutic compounds of this disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Uses and Methods

The antibodies, particularly the human antibodies, antibody compositions and methods of the present disclosure have numerous in vitro and in vivo diagnostic and therapeutic utilities involving the diagnosis and treatment of CXCR4 mediated disorders. For example, these molecules can be administered to cells in culture, in vitro or ex vivo, or to human subjects, e.g., in vivo, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by or modulated by CXCR4 activity or involving the CXCR4/SDF-1 pathway. When antibodies to CXCR4 are administered together with another agent, the two can be administered in either order or simultaneously.

Given the specific binding of the antibodies of this disclosure for CXCR4, the antibodies of this disclosure can be used to specifically detect CXCR4 expression on the surface of cells and, moreover, can be used to purify CXCR4 via immunoaffinity purification.

Suitable routes of administering the antibody compositions (e.g., human monoclonal antibodies, multispecific and bispecific molecules and immunoconjugates) of this disclosure in vivo and in vitro are well known in the art and can be selected by those of ordinary skill. For example, the antibody compositions can be administered by injection (e.g., intravenous or subcutaneous). Suitable dosages of the molecules used will depend on the age and weight of the subject and the concentration and/or formulation of the antibody composition.

As previously described, human anti-CXCR4 antibodies of this disclosure can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin (adriamycin), cisplatin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/ml dose once every 21 days. Co-administration of the human anti-CXCR4 antibodies, or antigen binding fragments thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells that would render them unreactive with the antibody.

Target-specific effector cells, e.g., effector cells linked to compositions (e.g., human antibodies, multispecific and bispecific molecules) of this disclosure can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing CXCR4, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of this disclosure and/or effector cells armed with these compositions can be used in conjunction with chemotherapy. Additionally, combination immunotherapy may be used to direct two distinct cytotoxic effector populations toward tumor cell rejection. For example, anti-CXCR4 antibodies linked to anti-Fc-gamma RI or anti-CD3 may be used in conjunction with IgG- or IgA-receptor specific binding agents.

Bispecific and multispecific molecules of this disclosure can also be used to modulate FcγR or FcγR levels on effector cells, such as by capping and elimination of receptors on the cell surface. Mixtures of anti-Fc receptors can also be used for this purpose.

The compositions (e.g., human, humanized, or chimeric antibodies, multispecific and bispecific molecules and immunoconjugates) of this disclosure which have complement binding sites, such as portions from IgG1, -2, or -3 or IgM which bind complement, can also be used in the presence of complement. In one embodiment, ex vivo treatment of a population of cells comprising target cells with a binding agent of this disclosure and appropriate effector cells can be supplemented by the addition of complement or serum containing complement. Phagocytosis of target cells coated with a binding agent of this disclosure can be improved by binding of complement proteins. In another embodiment target cells coated with the compositions (e.g., human antibodies, multispecific and bispecific molecules) of this disclosure can also be lysed by complement. In yet another embodiment, the compositions of this disclosure do not activate complement.

The compositions (e.g., human, humanized, or chimeric antibodies, multispecific and bispecific molecules and immunoconjugates) of this disclosure can also be administered together with complement. Accordingly, within the scope of this disclosure are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of this disclosure and the complement or serum can be administered separately.

The antibodies of this disclosure also can be used in combination with one or more additional therapeutic antibodies or other binding agents, such as Ig fusion proteins. Non-limiting examples of other antibodies or binding agents with which an anti-CXCR4 antibody of this disclosure can be administered in combination include antibodies or binding agents to CTLA-4, PSMA, CD30, IP-10, CD70, PD-1, PD-L1, TNF, TNF-R, VEGF, VEGF-R, CCR5, IL-1, IL-18, IL-18R, CD19, Campath-1, EGFR, CD33, CD20, Her-2, CD25, gpIIb/IIIa, IgE, CD11a, α4 integrin, IFNα and IFNAR1.

Also within the scope of the present disclosure are kits comprising the antibody compositions of this disclosure (e.g., human antibodies, bispecific or multispecific molecules, or immunoconjugates) and instructions for use. The kit can further contain one ore more additional reagents, such as an immunosuppressive reagent, a cytotoxic agent or a radiotoxic agent, or one or more additional human antibodies of this disclosure (e.g., a human antibody having a complementary activity which binds to an epitope in the CXCR4 antigen distinct from the first human antibody).

Accordingly, patients treated with antibody compositions of this disclosure can be additionally administered (prior to, simultaneously with, or following administration of a human antibody of this disclosure) with another therapeutic agent, such as a cytotoxic or radiotoxic agent, which enhances or augments the therapeutic effect of the human antibodies.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The compositions (e.g., human antibodies, multispecific and bispecific molecules) of this disclosure can also be used to target cells expressing CXCR4, for example for labeling such cells. For such use, the binding agent can be linked to a molecule that can be detected. Thus, this disclosure provides methods for localizing ex vivo or in vitro cells expressing CXCR4. The detectable label can be, e.g., a radioisotope, a fluorescent compound, an enzyme, or an enzyme co-factor.

In a particular embodiment, this disclosure provides methods for detecting the presence of CXCR4 antigen in a sample, or measuring the amount of CXCR4 antigen, comprising contacting the sample, and a control sample, with a human monoclonal antibody, or an antigen binding portion thereof, which specifically binds to CXCR4, under conditions that allow for formation of a complex between the antibody or portion thereof and CXCR4. The formation of a complex is then detected, wherein a difference complex formation between the sample compared to the control sample is indicative the presence of CXCR4 antigen in the sample.

In yet another embodiment, immunoconjugates of this disclosure can be used to target compounds (e.g., therapeutic agents, labels, cytotoxins, radiotoxoins immunosuppressants, etc.) to cells which have CXCR4 cell surface receptors by linking such compounds to the antibody. Thus, this disclosure also provides methods for localizing ex vivo or in vivo cells expressing CXCR4 (e.g., with a detectable label, such as a radioisotope, a fluorescent compound, an enzyme, or an enzyme co-factor). Alternatively, the immunoconjugates can be used to kill cells which have CXCR4 cell surface receptors by targeting cytotoxins or radiotoxins to CXCR4.

CXCR4 is known to be expressed on a wide variety of tumor cells types and also is known to be involved in tumor metastasis. Moreover, as a coreceptor for HIV entry into T cells, CXCR4 is known to be involved in HIV infection. Additionally, the CXCR4/SDF-1 pathway has been shown to be involved in inflammatory conditions. Still further, the CXCR4/SDF-1 pathway has been shown to be involved in angiogenesis or neovascularization. Accordingly, the anti-CXCR4 antibodies (and immunoconjugates and bispecific molecules) of this disclosure can be used to modulate CXCR4 activity in each of these clinical situations, as follows:

A. Cancer

CXCR4 has been shown to be expressed by a variety of cancer types and in certain situations an inverse correlation has been established between CXCR4 expression and patient prognosis or survival. Non-limiting examples of cancer types associated with CXCR4 expression include: breast (Muller, A. et al. (2001) *Nature* 410:50-56); ovarian (Scotton, C. et al. (2001) *Br. J. Cancer* 85:891-897; prostate (Taichman, R. S. et al. (2002) *Cancer Res.* 62:1832-1837; non-small cell lung (Spano J. P. et al. (2004) *Ann. Oncol.* 15:613-617); pancreatic (Koshiba, T. et al. (2000) *Clin. Cancer Res.* 6:3530-3535); thyroid (Hwang, J. H. et al. (2003) *J. Clin. Endocrinol. Metab.* 88:408-416); nasopharyngeal carcinoma (Wang, N. et al. (2005) *J. Transl. Med.* 3:26-33); melanoma (Scala, S. et al. (2005) *Clin. Cancer Res.* 11:1835-1841); renal cell carcinoma (Staller, P. et al. (2003) *Nature* 425:307-311); lymphoma (Bertolini, F. et al. (2002) *Cancer Res.* 62:3530-3535); neuroblastoma (Geminder, H. et al. (2001) *J. Immunol.* 167:4747-4757); glioblastoma (Rempel, S. A. et al. (2000) *Clin. Cancer Res.* 6:102-111); rhabdomyosarcoma (Libura, J. et al. (2002) *Blood* 100:2597-2606); colorectal (Zeelenberg, I. S. et al. (2003) *Cancer Res.* 63:3833-3839); kidney (Schrader, A. J. et al. (2002) *Br. I Cancer* 86:1250-1256); osteosarcoma (Laverdiere, C. et al. (2005) *Clin. Cancer Res.* 11:2561-2567); acute lymphoblastic leukemia (Crazzolara, R. et al. (2001) *Br. I Haematol.* 115:545-553); and acute myeloid leukemia (Rombouts, E. J. C. et al. (2004) *Blood* 104:550-557).

In view of the foregoing, the anti-CXCR4 antibodies of this disclosure can be used in the treatment of cancers, including but not limited to a cancer selected from the group consisting of breast, ovarian, prostate, non-small cell lung, pancreatic, thyroid, nasopharyngeal carcinoma, melanoma, renal cell carcinoma, lymphoma, neuroblastoma, glioblastoma, rhabdomyosarcoma, colorectal, kidney, osteosarcoma, acute lymphoblastic leukemia and acute myeloid leukemia. The antibody can be used alone or in combination other cancer treatments, such as surgery and/or radiation, and/or with other anti-neoplastic agents, such as the anti-neoplastic agents discussed and set forth above, including chemotherapeutic drugs and other anti-tumor antigen antibodies, such as those that bind CD20, Her2, PSMA, Campath-1, EGFR and the like.

B. Viral Infections, Including HIV Infection

CXCR4 has been shown to be a coreceptor for HIV entry into T cells and, additionally, certain murine anti-CXCR4 antibodies have been demonstrated to be able to inhibit entry of HIV isolates into T cells (see Hou, T. et al. (1998) *J. Immunol.* 160:180-188; Carnec, X. et al. (2005) *J. Virol.* 79:1930-1938). Thus, CXCR4 can be used as a receptor by viruses for entry into the cell and antibodies to CXCR4 can be used to inhibit cell entry of such viruses that use CXCR4 as a receptor. Accordingly, the human anti-CXCR4 antibodies of this disclosure can be used to inhibit entry of a virus into a cell, wherein the virus uses CXCR4 as a receptor for cell entry, such that viral infection is inhibited. In a preferred embodiment, the antibodies are used to inhibit entry of HIV into T cells, e.g., in the treatment or prevention of HIV/AIDS. The antibody can be used alone or in combination with other anti-viral agents, such as anti-retroviral drugs such as AZT or protease inhibitors.

C. Inflammatory Conditions

The CXCR4/SDF-1 pathway has been shown to play a role in a variety of inflammatory conditions, including but not limited to inflammatory liver disease (Terada, R. et al. (2003) *Lab. Invest.* 83:665-672); autoimmune joint inflammation (Matthys, P. et al. (2001) *J. Immunol.* 167:4686-4692); allergic airway disease (Gonzalo, J. A. et al. (2000) *J. Immunol.* 165:499-508); and periodontal disease (Hosokawa, Y. et al. (2005) *Clin. Exp. Immunol.* 141:467-474).

Accordingly, the human anti-CXCR4 antibodies of this disclosure that inhibit binding of SDF-1 to CXCR4 can be used to inhibit inflammation in inflammatory disorders, including disorders selected from the group consisting of inflammatory liver disease, autoimmune joint inflammation, allergic airway disease, periodontal disease, rheumatoid arthritis, inflammatory bowel disease, systemic lupus erythematosus, Type I diabetes, inflammatory skin disorders (e.g., psoriasis, lichen planus), autoimmune thyroid disease, Sjogren's syndrome, pulmonary inflammation (e.g., chronic obstructive pulmonary disease, pulmonary sarcoidosis, lymphocytic alveolitis) and inflammatory kidney disease (e.g., IgA nephropathy, glomerulonephritis). The antibody can be used alone or in combination with other anti-inflammatory agents, such as non-steroidal anti-inflammatory drugs (NSAIDs), corticosteroids (e.g., prednisone, hydrocortisone), methotrexate, COX-2 inhibitors, TNF antagonists (e.g., etanercept, infliximab, adalimumab) and immunosuppressants (such as 6-mercaptopurine, azathioprine and cyclosporine A).

D. Angiogenesis

It has been demonstrated that SDF-1 induces neovascularization through recruitment of CXCR4-expressing hemangiocytes (Jin, D. K. et al. (2006) *Nat. Med.* 12:557-567). Moreover, blockade of the SDF-1/CXCR4 pathway can attenuate in vivo tumor growth by inhibiting angiogenesis in a VEGF-independent manner (Guleng, B. et al. (2005) *Cancer Res.* 65:5864-58-71). Still further, as demonstrated in Example 2, antibodies of this disclosure are capable of inhibiting capillary tube formation in vitro. Accordingly, the anti-CXCR4 antibodies of this disclosure that inhibit binding of SDF-1 to CXCR4 can be used to inhibit angiogenesis by interfering with the SDF-1/CXCR4 pathway. Inhibition of angiogenesis can be used, for example, to inhibit tumor growth or tumor metastasis (regardless of whether the tumor is CXCR4+). The antibody can be used alone or in combination with other anti-angiogenic agents, such as anti-VEGF antibodies.

E. Autologous Stem Cell Transplantation

Peripheral blood stem cells are the preferred source of stem cells for use in autologous stem cell transplantation, for example in the treatment of certain hematological malignancies. Collection of stem cells from the peripheral blood requires mobilization of $CD34^+$ stem cells from the bone marrow to the peripheral blood. Various cytokines, chemokines and adhesion molecules have been implicated in the regulation of this process (reviewed in Gazitt, Y. (2001) *J. Hematother. Stem Cell Res.* 10:229-236), including the interaction of CXCR4 and SDF-1. Moreover, a small molecule CXCR4 antagonist has been demonstrated to stimulate rapid mobilization of $CD34^+$ stem cells from the bone marrow to the periphery (see e.g., Devine, S. M. et al. (2004) *J. Clin. Oncol.* 22:1095-1102; Broxmeyer, H. E. et al. (2005) *J. Exp. Med.* 201:1307-1318; Flomenberg, N. et al. (2005) *Blood* 106:1867-1874). Accordingly, anti-CXCR4 antibodies of this disclosure that inhibit CXCR4 activity (i.e., antagonist antibodies) can be used to stimulate mobilization of $CD34^+$ stem cells from the bone marrow to the peripheral blood to allow for the use of such stem cells in transplantation (e.g., autologous transplantation), for example in the treatment of hematological disorders, such as multiple myeloma and non-Hodgkin's lymphoma. The antibody can be used alone or in combination with other agents used to stimulate mobilization of stem cells, such as G-CSF and/or GM-CSF. Thus, in another embodiment, the invention provides a method of stimulating mobilization of $CD34^+$ stem cells from bone marrow to peripheral blood in a subject, the method comprising administering to the subject an anti-CXCR4 antibody of the invention such that mobilization of $CD34^+$ stem cells from bone marrow to peripheral blood is stimulated. The method can further comprise collecting CD34+ stem cells from peripheral blood, such as for use in autologous stem cell transplantation.

The present disclosure is further illustrated by the following examples, which should not be construed as further limiting. The contents of all figures and all references, patents and published patent applications cited throughout this application are expressly incorporated herein by reference.

EXAMPLES

Example 1: Generation of Human Monoclonal Antibodies Against CXCR4

Anti-CXCR4 human monoclonal antibodies were generated using a combination approach in which, first, mice expressing human antibody genes were immunized to raise in the mice a repertoire of human immunoglobulins specific for human CXCR4 and then, second, a human antibody library was prepared from spleen cells of the mice and displayed on phage such that the phage were then screened for expression of antibodies with specificity for CXCR4. This combination approach is generally described in U.S. Application No. 20030091995 by Buechler et al.

Antigen

R1610 cells (a Chinese Hamster lung cell line, originally described in Thirion, J. P. et al. (1976) *Genetics* 83:137-147) were transfected with an expression vector encoding the full-length human CXCR4 protein such that the protein was expressed on the surface of the cells. A codon-optimized form of the CXCR4 cDNA was used in the expression vector, which was prepared as described in Mirzabekov, T. et al. (1999) *J. Biol. Chem.* 274:28745-28750. To enhance the immunogenicity of the cells, the cells were coated with trinitrophenol (TNP), by incubation with an aqueous solution of trinitrobenzenesulfonic acid (TNBS), available commercially as a 5% solution (Sigma, Cat. #P2297). More specifically, $1 \times 10^8$ cells were washed once with sterile PBS, incubated with 50 µl of the commercial 5% TNBS solution for one hour in the dark at room temperature and then washed three times with PBS. The resultant TNP-coated, CXCR-4-expressing R1610 cells were used as antigen for immunization. The final immunogen was a mix of 100 µl of TNP-coated, washed cells (1×10⁷ cells) plus 100 µl of Ribi adjuvant. Mice received six doses of the immunogen over time.

Transgenic Transchromosomic KM Mouse® Strain

Fully human monoclonal antibodies to CXCR4 were prepared by initially immunizing the KM strain of transgenic transchromosomic mice, which expresses human antibody genes. In this mouse strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of PCT Publication WO 01/09187. Additionally, this mouse strain carries a human kappa light chain transgene, KCo5 (as described in Fishwild et al. (1996) *Nature Biotechnology* 14:845-851) and also contains the SC20 transchromosome, which carries the human Ig heavy chain locus, as described in PCT Publication WO 02/43478. KM mice are also described in detail in U.S. Application No. 20020199213.

KM Immunization

To raise fully human monoclonal antibodies to CXCR4, mice of the KM Mouse® strain were immunized with R1610 cells transfected to express CXCR4 and coated with TNP (as described above for the antigen). General immunization schemes for the raising human antibodies in mice strains carrying human antibody genes are described in Lonberg, N. et al (1994) *Nature* 368(6474): 856-859; Fishwild, D. et al. (1996) *Nature Biotechnology* 14: 845-851 and PCT Publication WO 98/24884. The mice were 6-16 weeks of age upon the first infusion of antigen.

KM mice were immunized with antigen in Ribi adjuvant either intraperitonealy (IP), subcutaneously (Sc) or via footpad (FP), followed by 3-21 days IP, Sc or FP reimmunization (for a total of 6 immunizations) with the antigen in Ribi adjuvant. The immune response was monitored by retroorbital bleeds. The plasma was screened by FACS staining of CXCR4-expressing R1610 cells (versus untransfected parental R1610 cells). Mice with sufficient titers of anti-CXCR4 human immunoglobulin were used for harvesting spleens.

Preparation of Phage Display Library and Screening for Anti-CXCR4 Antibodies

Spleens harvested from the immunized mice described above were used to make a phage display library expressing human antibody heavy and light chains. More specifically total RNA was isolated from the spleens, cDNA was prepared from the RNA and human antibody variable region cDNA was specifically amplified by PCR, essentially as described in U.S. Patent Application 20030091995 by Buechler et al. The library of human antibody variable regions was cloned into phage expression vectors, again essentially as described in U.S. Patent Application 20030091995 by Buechler et al. The phage display library was screened for library members having affinity for CXCR4 by panning with human CXCR4 incorporated into magnetic proteoliposomes (CXCR4-MPL). MPLs expressing CXCR4, or other seven transmembrane (7TM) receptors (e.g., CCR5), such that the native conformation of the 7TM receptor is maintained, have been described previously (see e.g., Mirzabekov, T. et al. (2000) *Nat. Biotechnol.* 18:649-654; Babcock, G. J. et al. (2001) *J. Biol. Chem.* 276:38433-38440; PCT Publication WO 01/49265; U.S. Patent Application 20010034432). In brief, recombinant human CXCR4 that contained an epitope tag was solubilized from a transfected CXCR4-expressing cell line using the detergent CHAPSO and the protein was captured on magnetic beads via the epitope tag. A lipid membrane was reconstituted during removal of the detergent, such that the native membrane conformation of CXCR4 was maintained, to create the CXCR4-MPLs. Three rounds of panning of the phage display library on the CXCR4-MPLs led to a 30-fold enrichment of CXCR4-binders as compared to background. Variable region fragments of interest were recloned into a Fab expression vector and the Fab retested for antigen binding against transfected CXCR4-expressing cells. Whole antibodies were then generated from the Fabs using standard molecular biology techniques.

Fab clones F7, F9, D1 and E2 were selected for further analysis.

Example 2: Structural Characterization of Human Anti-CXCR4 Monoclonal Antibodies F7, F9, D1 and E2

The cDNA sequences encoding the heavy and light chain variable regions of the F7, F9, D1 and E2 Fab clones, obtained from phage display library screening as described in Example 1, were sequenced using standard DNA sequencing techniques.

The nucleotide and amino acid sequences of the heavy chain variable region of F7 are shown in FIGS. 1A and 1n SEQ ID NO: 33 and 25, respectively.

The nucleotide and amino acid sequences of the light chain variable region of F7 are shown in FIGS. 1B and 1n SEQ ID NO: 37 and 29, respectively.

Comparison of the F7 heavy chain immunoglobulin sequence to the known human germline immunoglobulin heavy chain sequences demonstrated that the F7 heavy chain utilizes a $V_H$ segment from human germline $V_H$ 3-48, a D segment from the human germline 4-23, and a JH segment from human germline JH 6B. Further analysis of the F7 $V_H$ sequence using the Kabat system of CDR region determination led to the delineation of the heavy chain CDR1, CDR2 and CD3 regions as shown in FIG. 1A and in SEQ ID NOs: 1, 5 and 9, respectively.

Comparison of the F7 light chain immunoglobulin sequence to the known human germline immunoglobulin light chain sequences demonstrated that the F7 light chain utilizes a $V_L$ segment from human germline $V_K$ L15 and a JK segment from human germline JK 1. Further analysis of the F7 $V_L$ sequence using the Kabat system of CDR region determination led to the delineation of the light chain CDR1, CDR2 and CD3 regions as shown in FIGS. 1B and 1n SEQ ID NOs: 13, 17 and 21, respectively.

The nucleotide and amino acid sequences of the heavy chain variable region of F9 are shown in FIG. 2A and in SEQ ID NO: 34 and 26, respectively.

The nucleotide and amino acid sequences of the light chain variable region of F9 are shown in FIG. 2B and in SEQ ID NO: 38 and 30, respectively.

Comparison of the F9 heavy chain immunoglobulin sequence to the known human germline immunoglobulin heavy chain sequences demonstrated that the F9 heavy chain utilizes a $V_H$ segment from human germline $V_H$ 3-48, a D segment from the human germline 4-23, and a JH segment from human germline JH 6B. Further analysis of the F9 $V_H$ sequence using the Kabat system of CDR region determination led to the delineation of the heavy chain CDR1, CDR2 and CD3 regions as shown in FIG. 2A and in SEQ ID NOs: 2, 6 and 10, respectively.

Comparison of the F9 light chain immunoglobulin sequence to the known human germline immunoglobulin light chain sequences demonstrated that the F9 light chain utilizes a $V_L$ segment from human germline $V_K$ L15 and a JK segment from human germline JK 1. Further analysis of the F9 $V_L$ sequence using the Kabat system of CDR region determination led to the delineation of the light chain CDR1, CDR2 and CD3 regions as shown in FIG. 2B and in SEQ ID NOs: 14, 18 and 22, respectively.

The nucleotide and amino acid sequences of the heavy chain variable region of D1 are shown in FIG. 3A and in SEQ ID NO: 35 and 27, respectively.

The nucleotide and amino acid sequences of the light chain variable region of D1 are shown in FIG. 3B and in SEQ ID NO: 39 and 31, respectively.

Comparison of the D1 heavy chain immunoglobulin sequence to the known human germline immunoglobulin heavy chain sequences demonstrated that the D1 heavy chain utilizes a $V_H$ segment from human germline $V_H$ 3-48, a D segment from the human germline 4-23, and a JH segment from human germline JH 6B. Further analysis of the D1 $V_H$ sequence using the Kabat system of CDR region determination led to the delineation of the heavy chain CDR1, CDR2 and CD3 regions as shown in FIG. 3A and in SEQ ID NOs: 3, 7 and 11, respectively.

Comparison of the D1 light chain immunoglobulin sequence to the known human germline immunoglobulin light chain sequences demonstrated that the D1 light chain utilizes a $V_L$ segment from human germline $V_K$ L15 and a JK segment from human germline JK 1. Further analysis of the D1 $V_L$ sequence using the Kabat system of CDR region determination led to the delineation of the light chain CDR1, CDR2 and CD3 regions as shown in FIG. 3B and in SEQ ID NOs: 15, 19 and 23, respectively.

The nucleotide and amino acid sequences of the heavy chain variable region of E2 are shown in FIG. 4A and in SEQ ID NO: 36 and 28, respectively.

The nucleotide and amino acid sequences of the light chain variable region of E2 are shown in FIG. 4B and in SEQ ID NO: 40 and 32, respectively.

Comparison of the E2 heavy chain immunoglobulin sequence to the known human germline immunoglobulin heavy chain sequences demonstrated that the E2 heavy chain utilizes a $V_H$ segment from human germline $V_H$ 3-48, a D segment from the human germline 4-23, and a JH segment from human germline JH 6B. Further analysis of the E2 $V_H$ sequence using the Kabat system of CDR region determination led to the delineation of the heavy chain CDR1, CDR2 and CD3 regions as shown in FIG. 4A and in SEQ ID NOs: 4, 8 and 12, respectively.

Comparison of the E2 light chain immunoglobulin sequence to the known human germline immunoglobulin light chain sequences demonstrated that the E2 light chain utilizes a $V_L$ segment from human germline $V_K$ L15 and a JK segment from human germline JK 1. Further analysis of the E2 $V_L$ sequence using the Kabat system of CDR region determination led to the delineation of the light chain CDR1, CDR2 and CD3 regions as shown in FIG. 4B and in SEQ ID NOs: 16, 20 and 24, respectively.

Analysis of the framework sequences of the $V_H$ and $V_L$ regions of F7, F9, D1 and E2, as compared to the germline sequences from which they were derived, identified various framework amino acid residues that differed from germline. Certain framework residues in the N-terminal regions of the $V_H$ and $V_L$ segments were chosen for "back-mutation" to restore the framework residue to the germline sequence, because these non-germline residues in the N-terminal portion were encoded by the primers used to create the phage display libraries described in Example 1. In particular, the following modified forms of the $V_H$ and $V_L$ segments of F7, F9, D1 and E2 (referred to as "GL" forms, for germline) were created using standard molecular biology techniques to substitute the germline amino acid residue at the indicated framework position:

F7GL $V_H$: Q1E, Q6E
F7GL $V_K$: MD, R3Q
F9GL $V_H$: Q1E, Q6E
F9GL $V_K$: E1D, V3Q, L4M
D1GL $V_H$: Q6E
D1GL $V_K$: V1D, W3Q, V4M
E2GL $V_H$: Q6E
E2GL $V_K$: E1D, V3Q, L4M

FIG. 5A shows the alignment of the F7 (SEQ ID NO: 25) and F7GL (SEQ ID NO: 41) heavy chain variable amino acid sequences with the germline $V_H$ 3-48 encoded amino acid sequence (SEQ ID NO: 49). The CDR1, CDR2 and CDR3 regions are delineated.

FIG. 5B shows the alignment of the F7 (SEQ ID NO: 29) and F7GL (SEQ ID NO: 45) light chain variable amino acid sequences with the germline $V_K$ L15 encoded amino acid sequence (SEQ ID NO: 50). The CDR1, CDR2 and CDR3 regions are delineated.

FIG. 6A shows the alignment of the F9 (SEQ ID NO: 26) and F9GL (SEQ ID NO: 42) heavy chain variable amino acid sequences with the germline $V_H$ 3-48 encoded amino acid sequence (SEQ ID NO: 49). The CDR1, CDR2 and CDR3 regions are delineated.

FIG. 6B shows the alignment of the F9 (SEQ ID NO: 30) and F9GL (SEQ ID NO: 46) light chain variable amino acid sequences with the germline $V_K$ L15 encoded amino acid sequence (SEQ ID NO: 50). The CDR1, CDR2 and CDR3 regions are delineated.

FIG. 7A shows the alignment of the D1 (SEQ ID NO: 27) and D1GL (SEQ ID NO: 43) heavy chain variable amino acid sequences with the germline $V_H$ 3-48 encoded amino acid sequence (SEQ ID NO: 49). The CDR1, CDR2 and CDR3 regions are delineated.

FIG. 7B shows the alignment of the D1 (SEQ ID NO: 31) and D1GL (SEQ ID NO: 47) light chain variable amino acid sequences with the germline $V_K$ L15 encoded amino acid sequence (SEQ ID NO: 50). The CDR1, CDR2 and CDR3 regions are delineated.

FIG. 8A shows the alignment of the E2 (SEQ ID NO: 28) and E2GL (SEQ ID NO: 44) heavy chain variable amino acid sequences with the germline $V_H$ 3-48 encoded amino acid sequence (SEQ ID NO: 49). The CDR1, CDR2 and CDR3 regions are delineated.

FIG. 8B shows the alignment of the E2 (SEQ ID NO: 32) and E2GL (SEQ ID NO: 48) light chain variable amino acid sequences with the germline $V_K$ L15 encoded amino acid sequence (SEQ ID NO: 50). The CDR1, CDR2 and CDR3 regions are delineated.

The F7, F9, D1 and E2 Fab fragments are converted to full-length antibodies using standard recombinant DNA techniques. For example, DNA encoding the $V_H$ and $V_K$ regions of one of the Fab fragments can be cloned into an expression vector that carries the heavy and light chain constant regions such that the variable regions are operatively linked to the constant regions. Alternatively, separate vectors can be used for expression of the full-length heavy chain and the full-length light chain. Non-limiting examples of expression vectors suitable for use in creating full-length antibodies include the pIE vectors described in U.S. Patent Application No. 20050153394 by Black.

Example 3: Binding Characteristics of Anti-CXCR4 Human Monoclonal Antibodies

In this example, binding characteristics of the anti-CXCR4 antibodies were examined by flow cytometry.

The human T cell line CEM, which expresses native human CXCR4 on its cell surface, was used to examine the ability of the F7, F9, D1 and E2 antibodies to bind to native, cell-surface CXCR4. Full-length F7, F9, D1 and E2 were titrated in a 1:3 serial dilution series, resulting in a concentration range from 300 nM to 5 pM. The antibodies were then mixed with CEM cells and allowed to bind before being detected with a FITC-conjugated anti-human IgG secondary antibody. The cells were then analyzed by fluorescent cytometry. The resulting mean fluorescence intensities are shown in the graph of FIG. 9, which demonstrates that all four anti-CXCR4 antibodies bind to CEM cells. The $EC_{50}$ for binding F7, F9, D1 and E2 were 21 nM, 14 nM, 80 nM and 290 nM, respectively.

To determine the ability of a panel of anti-CXCR4 antibodies to compete for binding to CXCR4, competition studies were performed. The four human anti-CXCR4 antibodies F9, F7, E2 and D1 were used, along with four commercially available murine monoclonal anti-CXCR4 antibodies (12G5, 708, 716 and 717; R&D Systems catalog #s: MAB170, MAB171, MAB172 and MAB173, respectively). The anti-CXCR4 antibodies were titrated in a 1:3 serial dilution series resulting in a concentration range from 300 nM to 5 pM in the presence of a constant concentration of FITC-labeled anti-CXCR4 antibody F9. The mixture of antibodies was then added to CEM cells and allowed to bind. The ability of each antibody to compete with F9 for binding to CEM cells was assessed by fluorescent cytometry and detection of FITC. The resulting mean fluorescent intensities are shown in the graph of FIG. 10, which demonstrates that all seven antibodies examined (F7, E2, D1, 12G5, 708, 716 and 717) were able to compete with F9 for binding to CEM cells, although the E2 antibody only demonstrated partial inhibition at high concentrations compared to the other antibodies.

In another set of experiments, the ability of the F7 mAb to bind to a variety of different cell lines was examined by flow cytometry by carrying out a FACS titration. Increasing amounts of mAb (from less than 0.001 µg/ml to more than 100 µg/ml) were incubated with 100,00 cells and binding assessed by flow cytometry. The Bmax value also was determined, which indicates approximately how many CXCR4 molecules are present on each cell. Based on the binding curves, an $EC_{50}$ for antibody binding was determined, the results of which are summarized below in Table 1:

TABLE 1

FACS Titration Results for mAb F7
Binding to Different Cell Lines

| Cell Type | $EC_{50}$ (µg/ml) | Bmax |
|---|---|---|
| Ramos | 0.48 | 106,000 |
| Raji | 0.34 | 52,536 |
| Namalwa | 1.57 | 116,000 |
| L540 | 3.69 | 31,868 |
| DMS79 | 3.99 | 24,587 |
| MDA-MB-231 | 9.24 | 14,186 |

Bmax = maximium binding (GMFI units)

The results show that F7 mAb is capable of binding effectively to each of the six cell lines tested, with the lowest $EC_{50}$s observed with the Ramos and Raji cell lines. These data also show that the expression of CXCR4 receptor is highest for Ramos and Namalwa cells and lowest for MDA-MB-231 cells and DMS79 cells.

In another binding experiment, the ability of the F7 mAb to bind to different subsets of human peripheral blood mononuclear cells (PBMCs) was examined. Human PBMCs were isolated by standard methods and different cellular subsets were isolated by FACS. In particular, the following cellular subsets were isolated: (i) $CD3^+$; (ii) $CD20^+$; (iii) $CD11b^+$ and (iv) $CD14^+$. Flow cytometry experiments conducted with the F7 mAb (at 33 µg/ml) demonstrated that the F7 mAb was capable of binding effectively to each of the four subsets, as compared to an isotype-matched control antibody.

Example 4: Inhibition of SDF-1 Binding to CXCR4 by Anti-CXCR4 Antibodies

To determine the ability of the anti-CXCR4 human antibodies to inhibit the binding of SDF-1 to CXCR4, a competition study was performed using $^{125}$I-labeled SDF-1 and CEM cells, which naturally express CXCR4. A comparison of anti-CXCR4 antibodies on blocking SDF-1 binding to CEM cells was performed by a standard radio-labeled ligand binding assay. The anti-CXCR4 antibodies were serially diluted 1:3 to yield a range of concentrations from 300 nM to 137 pM. The antibodies were added to 750,000 CEM cells in 100 µl in the presence of 100 pM $^{125}$I-SDF-1 with a specific activity of 2000 Ci/mmole (Amersham, catalog #IM314-25UCI). An irrelevant antibody of the same isotype was used as a negative control. The total possible bound radio-labeled ligand was determined by allowing the $^{125}$I-SDF-1 to bind to CEM cells in the absence of antibodies for 2 hours at 4° C. Non-specific binding of the radio-labeled ligand was determined by allowing the $^{125}$I-SDF-1 to bind in the presence of 1 µM unlabeled SDF-1 (Peprotech, catalog #300-28A). The amount of cell-associated $^{125}$I-SDF-1 was determined by standard methods. The results are shown in FIG. 11, which demonstrates that the F7 antibody provides the most effective blockade of SDF-1 binding to CXCR4 expressed on CEM cells. The F9 and D1 antibodies also blocked SDF-1 binding, although more moderately than F7. The E2 antibody, although it does bind to CXCR4 on CEM cells (as demonstrated in Example 3), did not effectively block SDF-1 binding to CXCR4 on CEM cells. The $EC_{50}$s for SDF-1 blockade by F7, F9 and D1 were 2.3 nM, 12.5 nM and 28.6 nM, respectively.

Example 5: Inhibition of SDF-1-Induced Calcium Flux by Anti-CXCR4 Antibodies

To determine the ability of the anti-CXCR4 human antibodies to inhibit calcium flux in CEM cells induced by SDF-1, CEM cells were first labeled with the fluorescent dye Calcium 3 (Molecular Devices). The anti-CXCR4 antibodies were titrated in a 1:3 serial dilution series resulting in a concentration range from 100 nM to 1 pM and allowed to bind to 200,000 CEM cells in 200 µl and incubated 10 minutes at room temperature prior to loading into a Flexstation machine (Molecular Devices). As a negative control, an irrelevant antibody of the same isotype was used. Cells were then stimulated with a final concentration of 50 nM recombinant human SDF-1α (Peprotech), added as 500 nM in a volume of 22 µl for a final volume of 222 µl. The resulting calcium flux was measured for 200 seconds per well. As a positive control, cells in the absence of antibody were stimulated with SDF-1α (made up in Hank's buffered saline (HBS) with 0.1% BSA or HBS) to achieve a maximum possible calcium flux signal. To determine a baseline, cells were stimulated with EMS with 0.1% BSA. The SDF-1α-stimulated release of calcium was measured by the development of calcium-dependent fluorescence over time. The area under the curve of the resulting fluorescence trace was reported as an indication of calcium flux. The resulting inhibition of calcium flux by the anti-CXCR4 antibodies is represented in FIG. 12. The data were plotted and the $EC_{50}$s were calculated using GraphPad Prism software and the non-linear curve fit, sigmoidal dose response formula. Antibodies F7, F9 and D1 inhibited SDF-1α-induced calcium flux. Antibody E2, although it did bind to CXCR4 (as demonstrated in Example 3), did not significantly inhibit SDF-1α-induced calcium flux. The $EC_{50}$s for inhibition of SDF-1-induced calcium flux by F7, F9 and D1 were 0.90 nM, 0.32 nM and 0.57 nM, respectively.

Example 6: Inhibition of SDF-1-Induced Migration of CEM Cells by Anti-CXCR4 Antibodies To determine the ability of the anti-CXCR4 human antibodies to inhibit migration of CEM cells induced by SDF-1, CEM cells first were labeled with the BATDA reagent (Perkin Elmer). The anti-CXCR4 antibodies were titrated in a 1:3 serial dilution series resulting in a concentration range from 100 nM to 1 pM and allowed to bind to labeled CEM cells at a density of 10 million cells per ml. As a negative control, an irrelevant antibody of the same isotype was used. Recombinant human SDF-1α (Peprotech) was added at 5 nM at 30 µl per well to the lower chamber of a 96 well Neuroprobe migration plate with 5.7 mm diameter filters per well. Each well contains 5 µM pores. Labeled CEM cells with and without antibody were loaded onto the filters at a concentration of 0.5 million cells per well in a volume of 50 µl. The migration plate was incubated at 37° C. for 2.5 hours. Migrated cells were captured in the lower chamber of the plate, lysed and detected with Europium detection solution (Perkin Elmer). The chemi-luminescent signal was recorded on a Fusion instrument. The resulting inhibition of SDF-1α-induced migration by the anti-CXCR4 antibodies in shown in FIG. 13. The results demonstrated that antibodies F7 and F9 inhibited migration effectively, while antibodies D1 and E2 did not significantly inhibit migration. The $EC_{50}$s for inhibition of SDF-1-induced CEM cell migration by F7 and F9 were 12.44 nM and 18.99 nM, respectively.

Example 7: Inhibition of HuVEC Capillary Tube Formation by Anti-CXCR4 Antibodies In this example, the ability of the anti-CXCR4 human antibodies to inhibit capillary tube formation by human umbilical vein endothelial cells (HuVEC) was examined. Matrigel was diluted 1:1 with RPMI and plated onto the wells of a 96 well plate and allowed to polymerize for 30 minutes at 37° C. HuVEC (from Cambrex, cat. #CC-2519) at 80% confluence were trypsanized and resuspended at $1\times10^6$ cells per ml in RPMI with 0.5% FBS. Antibodies were well mixed with HuVEC at a final concentration of 3 µg/ml and allowed to incubate at room temperature for 30 minutes. An irrelevant antibody of the same isotype or media alone was used as a negative control. As a positive control of inhibition of tube formation, a mouse anti-human αvβ3 (CD51/CD61) antibody (R&D Systems, cat. #MAB3050) was used. HuVEC with or without antibodies were plated onto the matrigel-coated wells and incubated at 37° C. for 18 hours.

The HuVEC incubated with media alone or with the isotype-matched control antibody formed capillary tubes resulting in the appearance of connected cells across the plate with 3-5 points of connection or branch points per cell. The HuVEC incubated with either the anti-CXCR4 human antibodies or the anti-αvβ3 antibody did not form capillary tubes. The cells appeared isolated and with few or no branch points. The anti-CXCR4 antibodies that were most effective in blocking SDF-1 binding, SDF-1-induced calcium flux and SDF-1-induced migration, namely F7 and F9, were also the most effective in inhibiting capillary tube formation. The anti-CXCR4 antibody E2, which binds to CXCR4 but does not block SDF-1 binding or SDF-1-induced effects, did not inhibit capillary tube formation.

Example 8: Inhibition of Tumor Cell Proliferation In Vitro by Anti-CXCR4 Antibodies In this example, the ability of the anti-CXCR4 human antibodies to inhibit proliferation of Ramos tumor cells (a human Burkitt's lymphoma cell line) in vitro was examined. In the assay, $1\times10^4$ cells/well were incubated with increasing doses ($10^{-3}$ to 300 nM) of F7 IgG4 antibody, F9 IgG1 antibody, E2 IgG1 antibody, F9 Fab' antibody or isotype controls. The cells were incubated with antibody for 72 hours, with $^3$H-thymidine being added for the final 24 hours of incubation to allow for monitoring of cell proliferation. Following the incubation, incorporation of $^3$H-thymidine by the cells was measured by standard techniques. The results are shown in the graph of FIG. 14. The results demonstrate that the F7 IgG4, F9 IgG1 and E2 IgG1 antibodies each were able to inhibit Ramos cell proliferation, as indicated by decreased $^3$H-thymidine incorporation when incubated with these antibodies, whereas the F9 Fab' fragment did not inhibit cell proliferation. These results indicate that the anti-CXCR4 human antibodies have a direct anti-proliferative effect on the tumor cells in vitro and thus do not require secondary cross-linking to achieve an anti-proliferative effect.

Example 9: Inhibition of Solid Tumor Cell Proliferation In Vivo by Anti-CXCR4 Antibodies In this example, the ability of the anti-CXCR4 human antibodies to inhibit proliferation of an established solid tumor in vivo was examined using a Ramos subcutaneous tumor cell model. In this assay, $10\times10^6$ Ramos cells/mouse were implanted into the flank region of each mouse and allowed to grow to a mean size of 40 mm$^3$, calculated by length×width×height/2 of the tumors. The mice then received an intraperitoneal (i.p.) injection of a first dose of antibody (designated as day 0 of treatment) and received a second i.p. dose of antibody on day 7. Mice treated with a Fab' fragment antibody also received i.p. antibody doses on day 3 and day 10. Groups of mice (n=8) were treated with either (i) vehicle; (ii) isotype control (15 mg/kg); (iii) F7 IgG4 (15 mg/kg); (iv) F9 IgG1 (15 mg/kg); (v) F9 Fab' (10 mg/kg); or (vi) anti-CD20 positive control (15 mg/kg). Tumor volume and mouse body weight were measured at regular intervals (approximately 2-3 times/week) between day 0 and day 30 post dosing. The results of the experiment are presented in FIGS. 15A, 15B and 15C, which show mean tumor volume (FIG. 15A), median tumor volume (FIG. 15B) and median % body weight change (FIG. 15C). The results demonstrated that, like the positive control, the F7 IgG4 and F9 IgG1 antibodies significantly inhibited tumor cell growth as measured by increased tumor volume, whereas the F9 Fab' fragment did not inhibit tumor cell growth as compared to the isotype control. All treatments were well-tolerated as indicated by no significant body weight change. The differences in body weights between treatments was most likely due to the weights of the tumors. The results indicate that the anti-CXCR4 human antibodies are capable of inhibiting growth of an established solid tumor in vivo.

Example 10: Increased Survival Time in a Mouse Systemic Tumor Cell Model by Treatment with an Anti-CXCR4 Antibody In this example, the ability of an anti-CXCR4 human antibody to increase survival time of mice was examined using a Ramos systemic tumor cell model. In this assay, $1 \times 10^6$ Ramos cells/mouse were injected intravenously (i.v.) into each mouse on day 0. The mice then received an intraperitoneal (i.p.) injection of a first dose of antibody on day 1 (i.e., one day after i.v. administration of tumor cells) and received four more i.p. doses of antibody, on days 5, 8, 15 and 22 (mice treated with the positive control antibody were treated only on day 1). Groups of mice (n=8) were treated with either (i) vehicle; (ii) isotype control (15 mg/kg); (iii) F9 IgG1 (15 mg/kg); or (iv) anti-CD19 positive control (15 mg/kg). Percent survival was measured at regular intervals between day 0 and day 50 post dosing (hind leg paralysis was used as the endpoint of the experiment). The results of the experiment are presented in FIG. 16, which shows percent survival over time. The median # days of survival for the mice treated with either vehicle or the isotype control were 23 and 25.5 days, respectively, whereas the median # days of survival of the mice treated with one dose of the anti-CD19 positive control was 39 days. Significantly, 100% of the mice in the group treated with five doses of the F9 IgG1 antibody survived to the end of the experiment. These results indicate that the anti-CXCR4 human antibody is capable of increasing survival times of mice in a systemic tumor cell model.

Example 11: Induction of Apoptosis by Anti-CXCR4 Monoclonal Antibody F7

In this example, the ability of the anti-CXCR4 mAb F7 to induce apoptosis in different cells was examined. In the apoptosis assay, F7 mAb at 10 μg/ml was incubated with either Ramos cells (500,000 cells), Namalwa cells (500,000 cells) or R1610 cells transfected to express CXCR4 (100,000 cells) Untransfected R1610 cells were used as a negative control. Anti-CXCR4 mAb F7 or isotype control antibody was incubated with cells at 37° C. and 250 μl samples were removed at 24, 48 and 72 hours. To assess apoptosis, the cells from various time points were incubated with Annexin V-FITC-FL1 and Propidium Iodide—FL3, followed by flow cytometry. The combined percentage of cells collected in the FL1, FL3 and FL1-FL3 double positive quadrants were considered apoptotic. To remove background, the percentages of isotype antibody—induced apoptotic cells was subtracted from the percentage of F7 mAb-induced apoptotic cells.

The results are summarized below in Table 2:

TABLE 2

Induction of Apoptosis by Anti-CXCR4 mAb F7

| Cells | Time (Hours) | % Apoptosis |
|---|---|---|
| R1610 | 72 | <1 |
| R1610-CXCR4 | 24 | 39 |

TABLE 2-continued

Induction of Apoptosis by Anti-CXCR4 mAb F7

| Cells | Time (Hours) | % Apoptosis |
|---|---|---|
| R1610-CXCR4 | 48 | 58 |
| R1610-CXCR4 | 72 | 46 |
| Ramos | 24 | 22 |
| Ramos | 48 | 31 |
| Ramos | 72 | 22 |
| Namalwa | 24 | 17 |
| Namalwa | 48 | 24 |
| Namalwa | 72 | 44 |

Total % apoptosis values are corrected for basleine changes induced by isotype control antibodies.

The results demonstrate that the F7 mAb is capable of inducing apoptosis in the Ramos, Namalwa and R1610-CXCR4 cells while F7 had no effect on induction of apoptosis of parental R1610 cells indicating that the response was CXCR4-specific.

Example 12: Additional Studies Showing Inhibition of Solid Tumor Cell Proliferation In Vivo by Anti-CXCR4 Antibodies In this example, the ability of anti-CXCR4 human antibodies to inhibit proliferation or induce apoptosis of established solid tumors in vivo was examined using additional tumor cell models similar to the Ramos model described above in Example 9. A variety of tumor cell lines were examined. Representative experiments and results are as follows.

In one experiment, $7.5 \times 10^6$ MDA-MB231 human breast cancer cells/mouse were implanted into the flank region of each mouse and allowed to grow to a mean size of 100 mm$^3$, calculated by length×width×height/2 of the tumors, which was day 7 post-implantation. The mice were randomized into different treatment groups and received an intraperitoneal (i.p.) injection of a first dose of antibody on day 7 post-implantation, received a second i.p. dose of antibody on day 14 post-implantation and then received a third dose on day 46 post-implantation. Groups of mice (n=9) were treated with either (i) vehicle (PBS); (ii) IgG1 isotype control (15 mg/kg); (iii) IgG4 isotype control (15 mg/kg); (iv) F7 IgG1 (15 mg/kg); or (v) F7 IgG4 (15 mg/kg). Tumor volumes were measured at regular intervals and the mean and median tumor volume determined for each treatment group at each interval. The results of this experiment are summarized below in Table 3, which shows mean tumor volume (in mm$^3$) and % tumor growth inhibition (TGI) at day 52, and median tumor volume (in mm$^3$) and % TGI at day 59 post-implantation:

TABLE 3

Tumor Growth Inhbition of MDA-MB231 Cells In Vivo by mAb F7

| | Day 52 | | Day 59 | |
|---|---|---|---|---|
| Treatment | Mean | TGI (%) | Median | TGI(%) |
| Vehicle | 154 | | 187 | |
| IgG1 Isotype Control | 172 | | 216 | |
| IgG4 Isotype Control | 188 | | 226 | |
| F7 Anti-CXCR4 IgG1 | 86 | 50 | 130 | 40 |
| F7 Anti-CXCR4 IgG4 | 79 | 58 | 108 | 52 |

Additionally, one of the mice in the F7 IgG4 treatment group was tumor free at day 59. The results demonstrate that the F7 mAb is capable of inhibiting growth of MDA-MB231 breast cancer cells in vivo.

In a second experiment, 5×10⁶ DMS79 human small cell lung carcinoma cells/mouse were implanted into the flank region of each mouse and allowed to grow to a mean size of 160 mm³, calculated by length×width×height/2 of the tumors, which was day 7 post-implantation. The mice were randomized into different treatment groups and received intraperitoneal (i.p.) injections of antibody on a dosing schedule of Q3D×5 (every three days for five times). Groups of mice (n=10) were treated with either (i) vehicle (PBS); (ii) IgG4 isotype control (10 mg/kg); or (iii) F7 IgG4 (10 mg/kg). Tumor volumes were measured at regular intervals and the mean and median tumor volume determined for each treatment group at each interval. The results of this experiment are summarized below in Table 4, which shows mean and median tumor volume (in mm³) and % tumor growth inhibition (TGI) at day 34 post-implantation:

TABLE 4

Tumor Growth Inhbition of DMS79 Cells In Vivo by mAb F7

| Treatment | Day 34 | | | |
|---|---|---|---|---|
| | Mean | TGI (%) | Median | TGI(%) |
| Vehicle | 900 | | 882 | |
| IgG4 Isotype Control | 992 | | 903 | |
| F7 Anti-CXCR4 IgG4 | 620 | 38 | 599 | 34 |

The results demonstrate that the F7 mAb is capable of inhibiting growth of DMS79 human small cell lung carcinoma cells in vivo.

Additional subcutaneous xenograft tumor models were tested for the ability of anti-CXCR4 antibodies to inhibit tumor growth, in experiments similar to those described above and in Example 9. In an experiment using SU-DHL-6 B cell lymphoma cells, the results showed that treatment with the F7 IgG4 mAb at 15 mg/kg resulted in approximately 60% tumor growth inhibition. Similarly, in an experiment using Namalwa Burkitt's lymphoma cells, the results showed that treatment with the F7 IgG4 mAb at 3 mg/kg resulted in approximately 70% tumor growth inhibition. In contrast, no tumor growth inhibition by the F7 mAb was observed in experiments using NIH-H226 lung carcinoma cells or HPAC human pancreatic adenocarcinoma cells. However, staining of these cells by the F7 mAb in flow cytometry experiments showed minimal in vitro expression. Although the tumor cells in vivo were stainable by the mAb by immunohistochemistry, it is unclear at what stage of their tumor growth CXCR4 began to be expressed. This suggests that expression of CXCR4 by these two cell lines was insufficient to allow for tumor growth inhibition or induction of apoptosis in vivo by anti-CXCR4 treatment.

Example 13: Inhibition of Lung Metastases In Vivo by Anti-CXCR4 Antibodies

In this example, the ability of the F7 anti-CXCR4 mAb to inhibit lung metastases was examined using a C57 mouse systemic tumor model. More specifically, 0.4×10⁶ B16-CXCR4 cells (B16 cells transfected to express human CXCR4) were injected intravenously into each of 30 mice of the C57 strain. The mice were randomized into three groups of ten mice each, which were then treated with either (i) vehicle (PBS); (ii) IgG4 isotype control (5 mg/kg); or (iii) F7 IgG4 (5 mg/kg). The antibody or vehicle was injected intraperitoneally 30 minutes after the B16-CXCR4 cells were injected intravenously. Lungs were harvested on day 14 and the number of lung metastasis nodules was quantitated. The results are summarized below in Table 5, which shows the mean and median number of lung metastases in each group:

TABLE 5

Inhbition of Lung Metastases In Vivo by mAb F7

| Treatment | Number of Lung Metastases | | % Inhibition of Lung Mets (Mean) |
|---|---|---|---|
| | Mean | Median | |
| Vehicle | 364 | 397 | |
| IgG4 Isotype Control | 309 | 294 | 15% |
| F7 Anti-CXCR4 IgG4 | 157 | 186 | 56% |

The results show that treatment with the F7 mAb led to a reduction in the mean number of lung metastatic nodules of 56%, whereas reduction was only 15% with the isotype control antibody, demonstrating that the F7 mAb is capable of inhibiting lung metastases in a systemic tumor model.

What is claimed is:

1. A method of modulating C-X-C chemokine receptor type 4 (CXCR4) activity in a cell comprising contacting the cell with a monoclonal antibody or an antigen-binding portion thereof such that CXCR4 activity in the cell is modulated, wherein the monoclonal antibody or antigen-binding portion thereof binds to native human CXCR4 expressed on a cell surface and comprises:
   (a) a heavy chain variable region CDR1 comprising amino acids having the sequence set forth in SEQ ID NO: 1; a heavy chain variable region CDR2 comprising amino acids having the sequence set forth in SEQ ID NO: 5; a heavy chain variable region CDR3 comprising amino acids having the sequence set forth in SEQ ID NO: 9; a light chain variable region CDR1 comprising amino acids having the sequence set forth in SEQ ID NO: 13; a light chain variable region CDR2 comprising amino acids having the sequence set forth in SEQ ID NO: 17; and a light chain variable region CDR3 comprising amino acids having the sequence set forth in SEQ ID NO: 21;
   (b) a heavy chain variable region CDR1 comprising amino acids having the sequence set forth in SEQ ID NO: 2; a heavy chain variable region CDR2 comprising amino acids having the sequence set forth in SEQ ID NO: 6; a heavy chain variable region CDR3 comprising amino acids having the sequence set forth in SEQ ID NO: 10; a light chain variable region CDR1 comprising amino acids having the sequence set forth in SEQ ID NO: 14; a light chain variable region CDR2 comprising amino acids having the sequence set forth in SEQ ID NO: 18; and a light chain variable region CDR3 comprising amino acids having the sequence set forth in SEQ ID NO: 22; or
   (c) a heavy chain variable region CDR1 comprising amino acids having the sequence set forth in SEQ ID NO: 3; a heavy chain variable region CDR2 comprising amino acids having the sequence set forth in SEQ ID NO: 7; a heavy chain variable region CDR3 comprising amino acids having the sequence set forth in SEQ ID NO: 11; a light chain variable region CDR1 comprising amino acids having the sequence set forth in SEQ ID NO: 15; a light chain variable region CDR2 comprising amino acids having the sequence set forth in SEQ ID NO: 19; and a light chain variable region CDR3 comprising amino acids having the sequence set forth in SEQ ID NO: 23.

2. The method of claim 1, wherein the monoclonal antibody or antigen-binding portion thereof:
   (a) is of an IgG1 or IgG4 isotype or an antigen-binding portion thereof;
   (b) inhibits binding of stromal cell-derived factor 1 (SDF-1) to human CXCR4;
   (c) inhibits stromal cell-derived factor 1 (SDF-1)-induced calcium flux in cells expressing human CXCR4;
   (d) inhibits SDF-1-induced migration of cells expressing human CXCR4;
   (e) inhibits capillary tube formation by human umbilical vein endothelial cells; and/or
   (f) induces apoptosis in cells expressing human CXCR4, and inhibits growth and/or induces apoptosis of CXCR4$^+$ tumor cells in vivo.

3. The method of claim 1, wherein CXCR4 activity is modulated in vitro by culturing the cell with the monoclonal antibody or antigen-binding portion thereof.

4. The method of claim 1, wherein the cell is a tumor cell expressing CXCR4 and the method results in inhibition of growth of the tumor cell.

5. The method of claim 1, wherein:
(a) the cell is a T cell expressing CXCR4 and the method results in inhibition of entry of HIV into the cell;
(b) the cell is a lymphocyte in an inflammatory disorder and the method results in inhibition of inflammation; or
(c) the cell is involved in vascularization and the method results in modulation of angiogenesis.

6. The method of claim 1, wherein CXCR4 activity is modulated in vivo in a subject by administering to the subject the monoclonal antibody or antigen-binding portion thereof.

7. The method of claim 6, wherein the monoclonal antibody or antigen-binding portion thereof:
(a) is linked to a therapeutic agent to form an immunoconjugate; or
(b) is linked to a second functional moiety having a different binding specificity than the monoclonal antibody or portion thereof to form a bispecific molecule.

8. The method of claim 6, wherein the cell is a tumor cell expressing CXCR4 and the method results in inhibition of growth of the tumor cell, inhibition of metastasis of the tumor cell, and/or an increase in the survival time of the subject.

9. The method of claim 8, wherein the tumor cell is chosen from a cell of a B cell leukemia, a lymphoma, an acute lymphoblastic leukemia, an acute myeloid leukemia, a small-cell lung carcinoma, a non-small-cell lung cancer, a breast cancer, an ovarian cancer, a prostate cancer, a pancreatic cancer, a thyroid cancer, a nasopharyngeal carcinoma, a melanoma, a renal cell carcinoma, a neuroblastoma, a glioblastoma, a rhabdomyosarcoma, a colorectal cancer, a kidney cancer, an osteosarcoma, and a metastatic lung cancer.

10. The method of claim 6, wherein the cell is a T cell expressing CXCR4 and the method results in inhibition of entry of HIV into the cell, wherein the HIV uses CXCR4 as a coreceptor for entry into the T cell.

11. The method of claim 6, wherein the cell is a lymphocyte in an inflammatory disorder and the method results in inhibition of inflammation.

12. The method of claim 6, wherein the cell is involved in vascularization and the method results in modulation of angiogenesis.

13. A method of stimulating mobilization of $CD34^+$ stem cells from bone marrow to peripheral blood in a subject, the method comprising administering to the subject a monoclonal antibody or an antigen-binding portion thereof such that mobilization of $CD34^+$ stem cells from bone marrow to peripheral blood is stimulated, wherein the monoclonal antibody or antigen-binding portion thereof binds to native human C-X-C chemokine receptor type 4 (CXCR4) expressed on a cell surface and comprises:
(a) a heavy chain variable region CDR1 comprising amino acids having the sequence set forth in SEQ ID NO: 1; a heavy chain variable region CDR2 comprising amino acids having the sequence set forth in SEQ ID NO: 5; a heavy chain variable region CDR3 comprising amino acids having the sequence set forth in SEQ ID NO: 9; a light chain variable region CDR1 comprising amino acids having the sequence set forth in SEQ ID NO: 13; a light chain variable region CDR2 comprising amino acids having the sequence set forth in SEQ ID NO: 17; and a light chain variable region CDR3 comprising amino acids having the sequence set forth in SEQ ID NO: 21;
(b) a heavy chain variable region CDR1 comprising amino acids having the sequence set forth in SEQ ID NO: 2; a heavy chain variable region CDR2 comprising amino acids having the sequence set forth in SEQ ID NO: 6; a heavy chain variable region CDR3 comprising amino acids having the sequence set forth in SEQ ID NO: 10; a light chain variable region CDR1 comprising amino acids having the sequence set forth in SEQ ID NO: 14; a light chain variable region CDR2 comprising amino acids having the sequence set forth in SEQ ID NO: 18; and a light chain variable region CDR3 comprising amino acids having the sequence set forth in SEQ ID NO: 22; or
(c) a heavy chain variable region CDR1 comprising amino acids having the sequence set forth in SEQ ID NO: 3; a heavy chain variable region CDR2 comprising amino acids having the sequence set forth in SEQ ID NO: 7; a heavy chain variable region CDR3 comprising amino acids having the sequence set forth in SEQ ID NO: 11; a light chain variable region CDR1 comprising amino acids having the sequence set forth in SEQ ID NO: 15; a light chain variable region CDR2 comprising amino acids having the sequence set forth in SEQ ID NO: 19; and a light chain variable region CDR3 comprising amino acids having the sequence set forth in SEQ ID NO: 23.

14. The method of claim 13, which further comprises collecting the $CD34^+$ stem cells from the peripheral blood.

15. The method of claim 8, which further comprises administering to the subject an additional anti-neoplastic therapeutic agent in combination with the monoclonal antibody or antigen-binding portion thereof.

16. The method of claim 15, wherein the additional anti-neoplastic therapeutic agent is an antibody that binds to CTLA-4, PD-1 or PD-L1.

17. The method of claim 16, wherein the tumor cell is chosen from a cell of a B cell leukemia, a lymphoma, an acute lymphoblastic leukemia, an acute myeloid leukemia, a small-cell lung carcinoma, a non-small-cell lung cancer, a breast cancer, an ovarian cancer, a prostate cancer, a pancreatic cancer, a thyroid cancer, a nasopharyngeal carcinoma, a melanoma, a renal cell carcinoma, a neuroblastoma, a glioblastoma, a rhabdomyosarcoma, a colorectal cancer, a kidney cancer, an osteosarcoma, and a metastatic lung cancer.

18. The method of claim 8, which further comprises administering to the subject an antibody that binds to PD-1, wherein the tumor cell is a cell of a pancreatic cancer or a small-cell lung carcinoma.

19. The method of claim 1, wherein the monoclonal antibody or antigen-binding portion thereof comprises a heavy chain variable region comprising amino acids having the sequence set forth in SEQ ID NO: 25, and a light chain variable region comprising amino acids having the sequence set forth in SEQ ID NO: 29.

20. The method of claim 1, wherein the monoclonal antibody or antigen-binding portion thereof comprises a heavy chain variable region comprising amino acids having the sequence set forth in SEQ ID NO: 41, and a light chain variable region comprising amino acids having the sequence set forth in SEQ ID NO: 45.

21. The method of claim 1, wherein the monoclonal antibody or antigen-binding portion thereof comprises:
(a) a heavy chain variable region comprising amino acids having the sequence set forth in SEQ ID NO: 26 or 42, and a light chain variable region comprising amino acids having the sequence set forth in SEQ ID NO: 30 or 46; or (b) a heavy chain variable region comprising amino acids having the sequence set forth in SEQ ID NO: 27 or 43, and a light chain variable region comprising amino acids having the sequence set forth in SEQ ID NO: 31 or 47.

22. The method of claim 13, wherein the monoclonal antibody or antigen-binding portion thereof comprises a heavy chain variable region comprising amino acids having the sequence set forth in SEQ ID NO: 25, and a light chain variable region comprising amino acids having the sequence set forth in SEQ ID NO: 29.

23. The method of claim 13, wherein the monoclonal antibody or antigen-binding portion thereof comprises a heavy chain variable region comprising amino acids having the sequence set forth in SEQ ID NO: 41, and a light chain variable region comprising amino acids having the sequence set forth in SEQ ID NO: 45.

24. The method of claim 13, wherein the monoclonal antibody or antigen-binding portion thereof comprises:
 (a) a heavy chain variable region comprising amino acids having the sequence set forth in SEQ ID NO: 26 or 42, and a light chain variable region comprising amino acids having the sequence set forth in SEQ ID NO: 30 or 46; or
 (b) a heavy chain variable region comprising amino acids having the sequence set forth in SEQ ID NO: 27 or 43, and a light chain variable region comprising amino acids having the sequence set forth in SEQ ID NO: 31 or 47.

* * * * *